United States Patent [19]
Sakamoto et al.

[11] Patent Number: 4,991,957
[45] Date of Patent: Feb. 12, 1991

[54] BORESCOPE APPARATUS

[75] Inventors: Nobuyuki Sakamoto, Tokyo; Yoshio Shishido, Sagamihara; Masahiro Kumakura, Zama; Morihide Mizumoto, Tokyo; Morihide Tojo, Tokyo; Ryouji Masubuchi, Tokyo; Atsushi Miyazaki, Tokyo; Satoshi Tagami, Tokyo; Hiroshi Hasegawa, Tokyo; Shinichi Nishigaki, Tokyo; Yasuhiro Ueda, Tokyo; toshiaki Nishikiori, Sagamihara; Kunio Kinoshita, Tokyo; Takeaki Nakamura, Tokyo; Eiichi Fuse, Tokyo; Yoshisada Aoki, Tokyo; Kazuhiro Misono, Tokyo, all of Japan

[73] Assignee: Olympus Optical Co., Ltd., Tokyo, Japan

[21] Appl. No.: 241,078

[22] Filed: Sep. 6, 1988

[30] Foreign Application Priority Data

| Sep. 8, 1987 | [JP] | Japan | 62-223170 |
| Sep. 17, 1987 | [JP] | Japan | 62-233458 |
| Sep. 21, 1987 | [JP] | Japan | 62-236851 |
| Sep. 21, 1987 | [JP] | Japan | 62-236852 |
| Sep. 21, 1987 | [JP] | Japan | 62-236854 |
| Sep. 21, 1987 | [JP] | Japan | 62-144098[U] |
| Nov. 16, 1987 | [JP] | Japan | 62-288740 |
| Jan. 11, 1988 | [JP] | Japan | 63-2512 |
| Mar. 8, 1988 | [JP] | Japan | 63-54083 |
| Mar. 8, 1988 | [JP] | Japan | 63-30806[U] |
| Mar. 9, 1988 | [JP] | Japan | 63-55362 |
| Mar. 9, 1988 | [JP] | Japan | 63-537612 |
| Mar. 9, 1988 | [JP] | Japan | 63-53760 |
| Mar. 16, 1988 | [JP] | Japan | 63-62276 |
| Apr. 6, 1988 | [JP] | Japan | 63-83005 |
| Apr. 7, 1988 | [JP] | Japan | 63-85784 |
| Apr. 14, 1988 | [JP] | Japan | 63-50115[U] |

[51] Int. Cl.⁵ .................................. G02B 23/26
[52] U.S. Cl. ........................ 356/241; 350/96.26
[58] Field of Search .............. 356/241; 128/4, 4 A, 128/6; 350/96–126

[56] References Cited

U.S. PATENT DOCUMENTS

| 4,189,944 | 2/1980 | Day et al. |
| 4,485,668 | 12/1984 | Hudson et al. |
| 4,735,501 | 4/1988 | Ginsburgh et al. |
| 4,793,326 | 12/1988 | Shishido |

FOREIGN PATENT DOCUMENTS

| 0242428A2 | 10/1987 | European Pat. Off. |
| DE31114-97A1 | 10/1982 | Fed. Rep. of Germany |
| DE3500544-C1 | 9/1986 | Fed. Rep. of Germany |
| DE35328-85A1 | 3/1987 | Fed. Rep. of Germany |
| 1278965 | 1/1961 | France |
| 189604 | 11/1983 | Japan ................ 350/96.26 |
| 60-177262 | 9/1985 | Japan |
| 62-251639 | 11/1987 | Japan |
| 63-314980 | 12/1988 | Japan |

Primary Examiner—Vincent P. McGraw
Assistant Examiner—Matthew W. Koren
Attorney, Agent, or Firm—Frishauf, Holtz, Goodman & Woodward

[57] ABSTRACT

A borescope apparatus having a borescope and a pressurized fluid supply device. The borescope has an operation unit and an insertion unit. The insertion unit comprises a bending tube portion, a jet port member coupled to a proximal end of the bending tube portion, and a flexible tube portion. The bending tube portion can be bent by operating the operation unit. The jet port member has a jet port. A pressuring fluid is supplied from the fluid supply unit to the jet port member, and is ejected through the jet port. The flexible tube portion can be bent by a jet of the fluid from through the jet port independently of the bending tube portion.

28 Claims, 80 Drawing Sheets

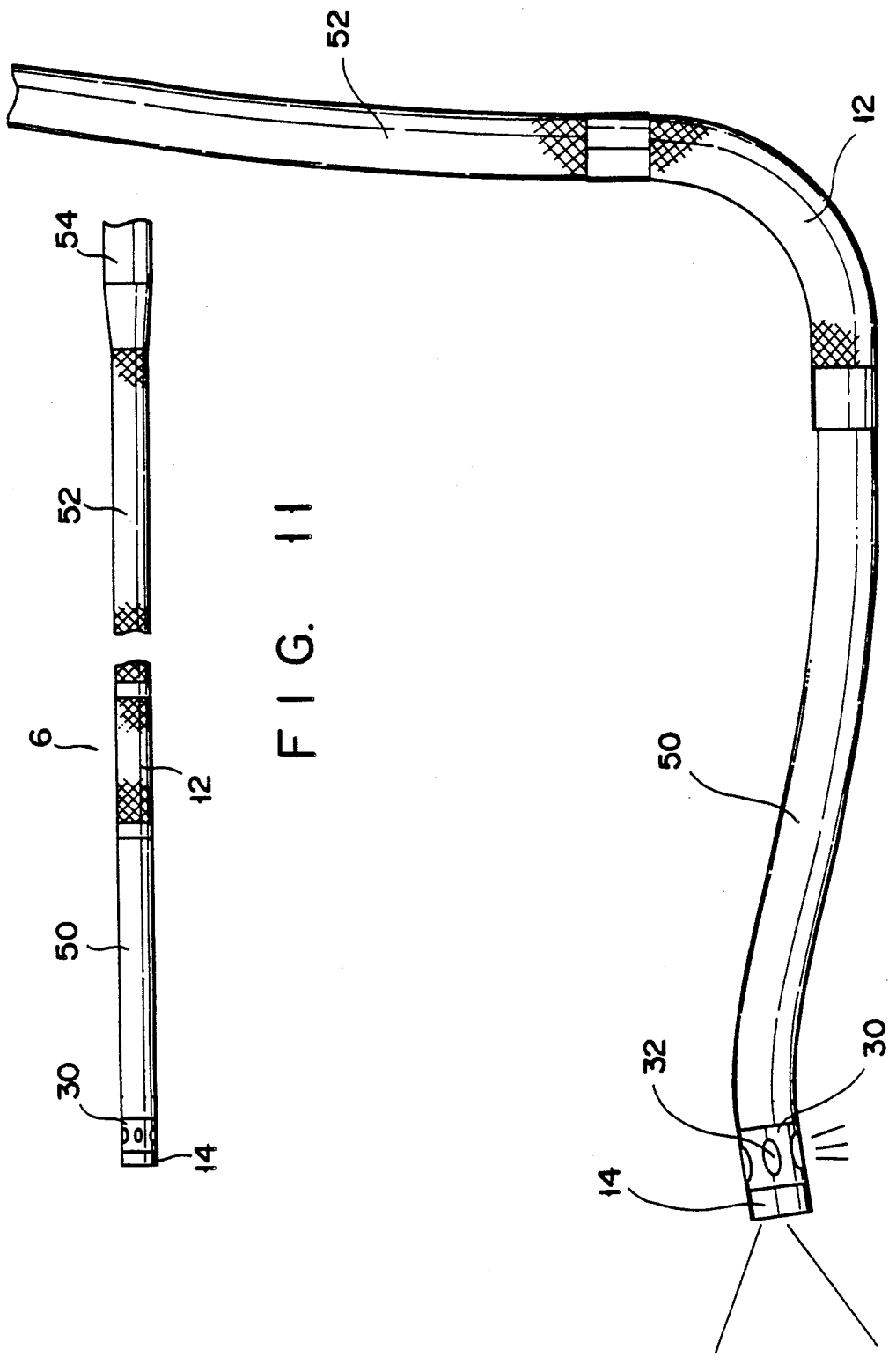

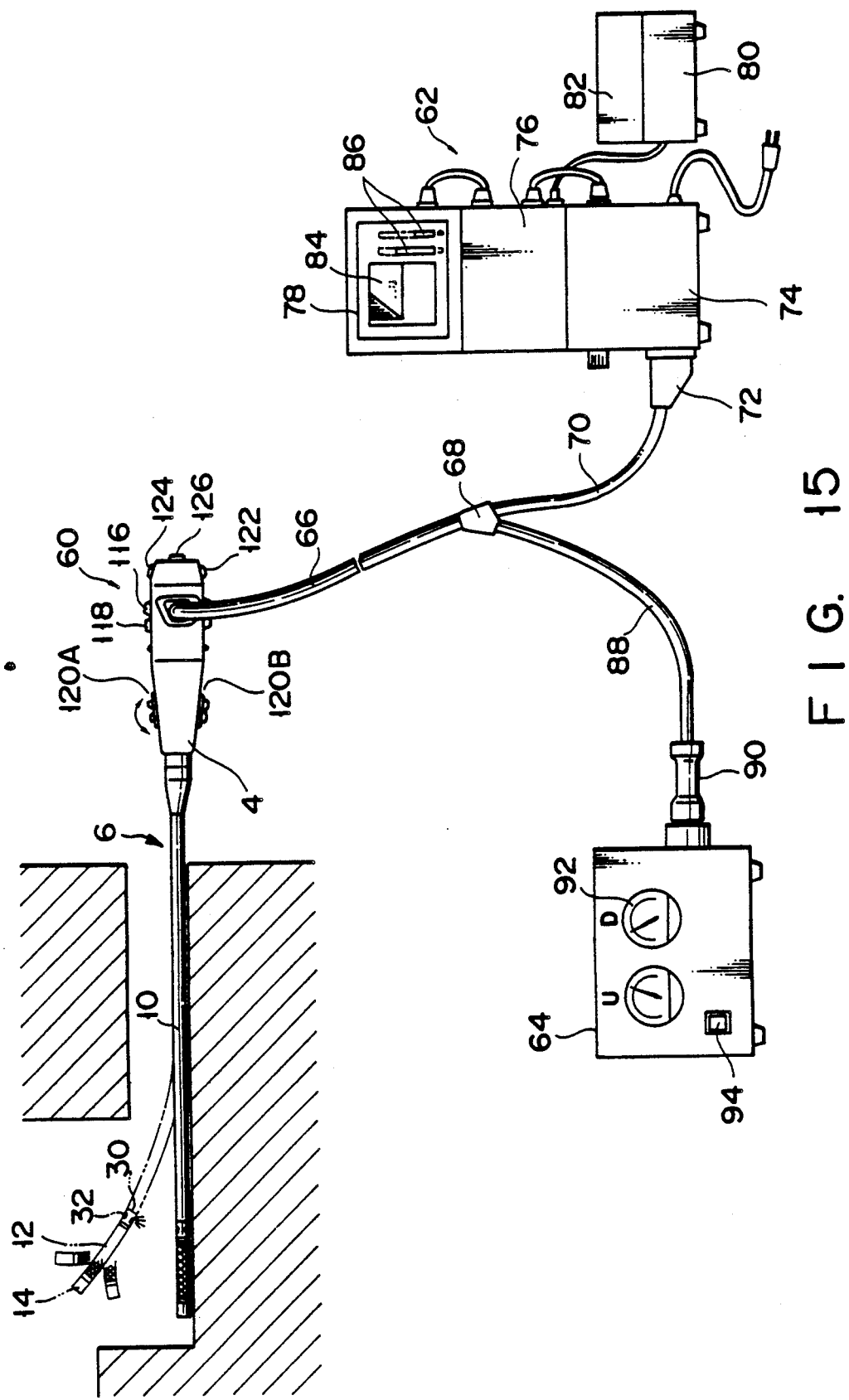

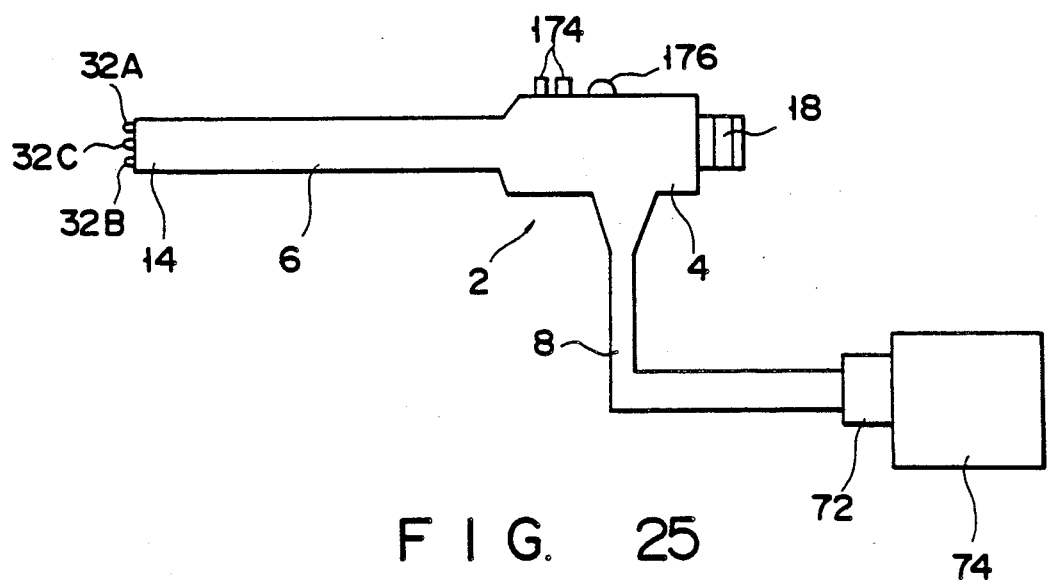
F I G. 25
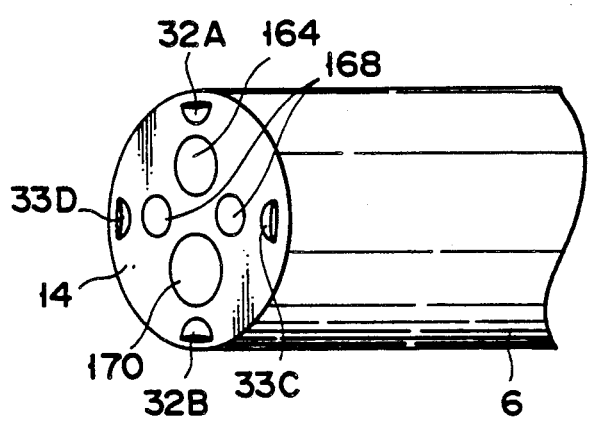
F I G. 26

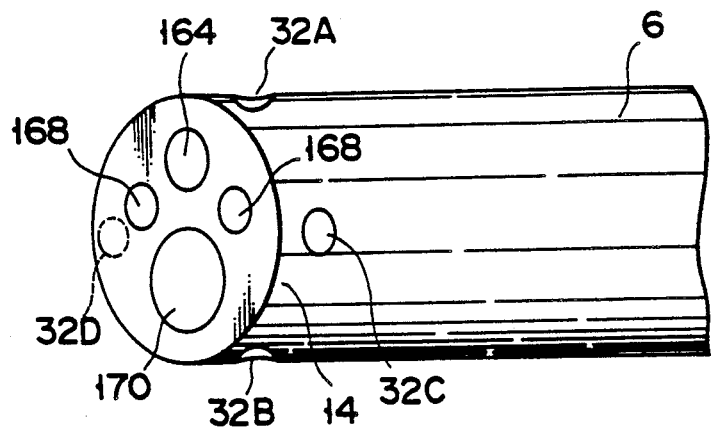
F I G. 32
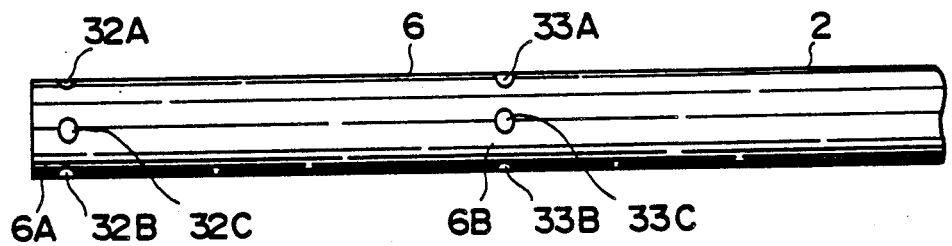
F I G. 33
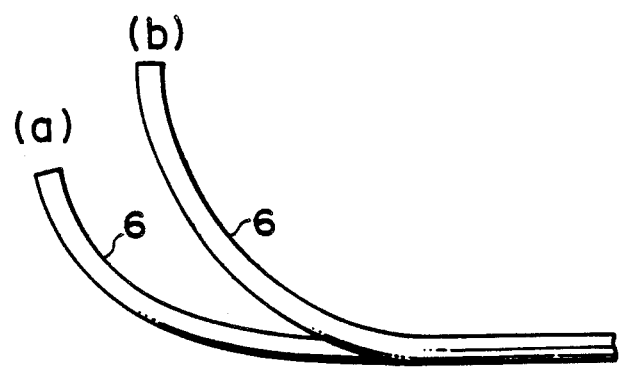
F I G. 34

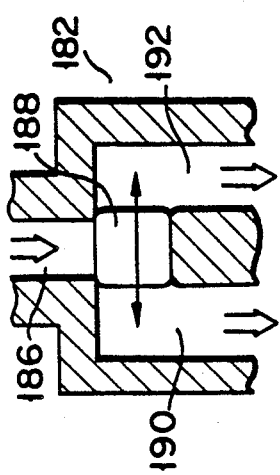
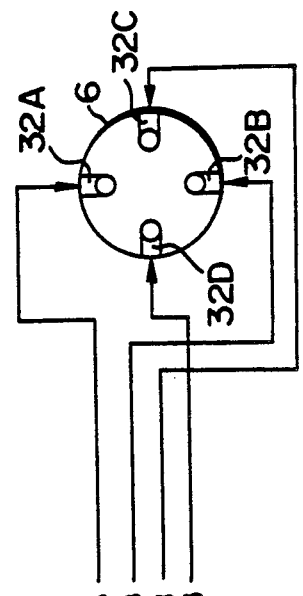
FIG. 38
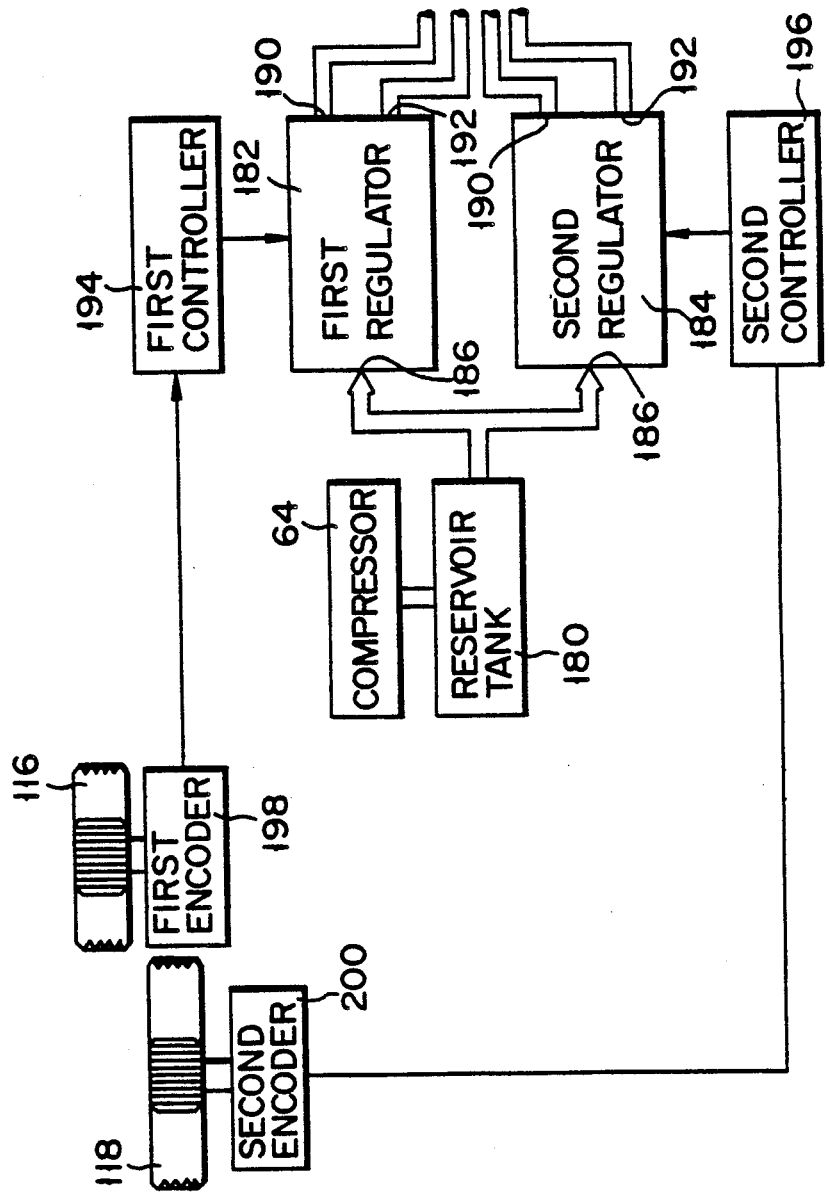
FIG. 37

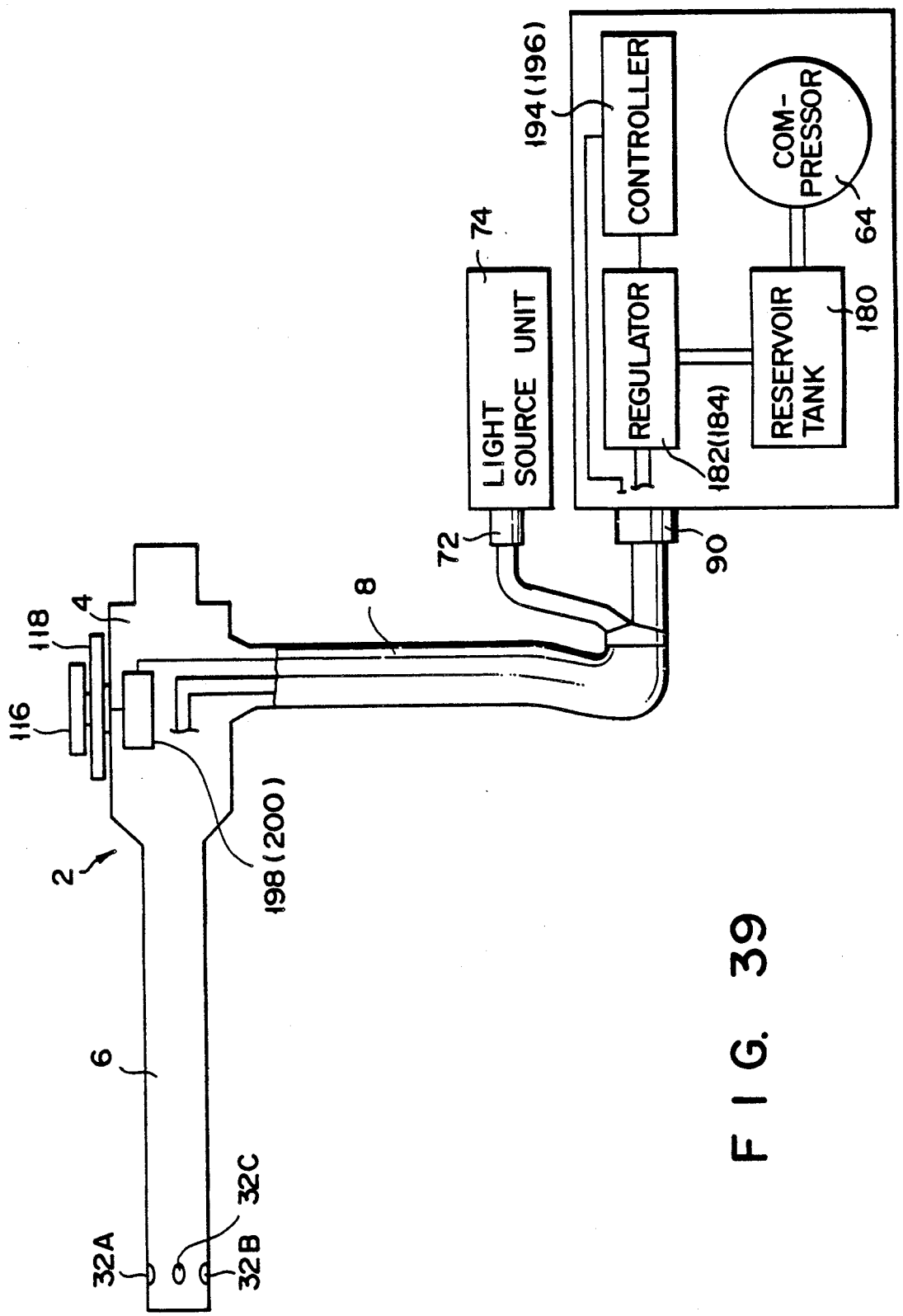
F I G. 39

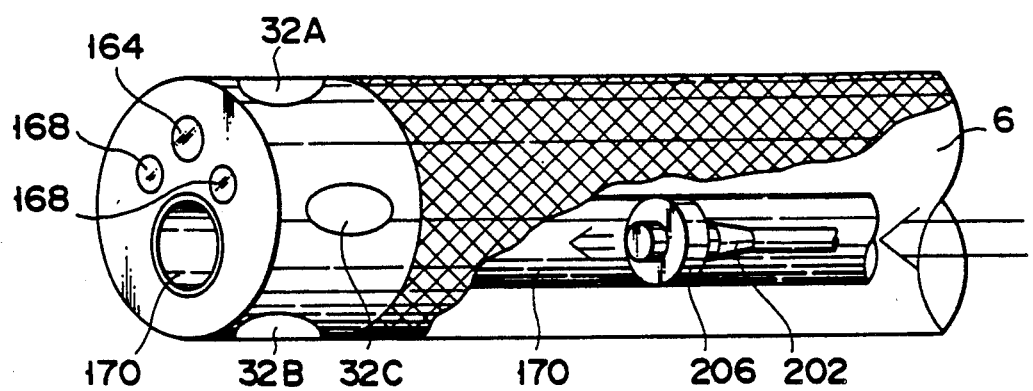
FIG. 40
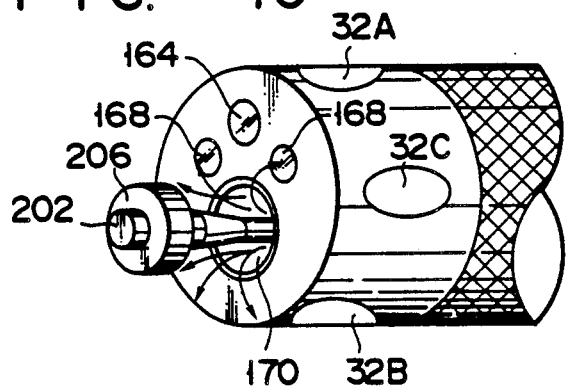
FIG. 41
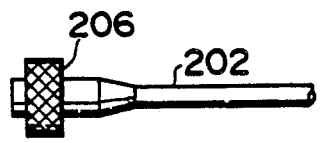
FIG. 42
FIG. 43
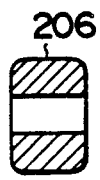 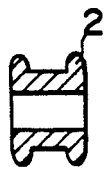 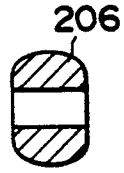 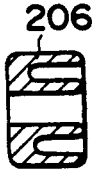
FIG. 44   FIG. 45   FIG. 46   FIG. 47

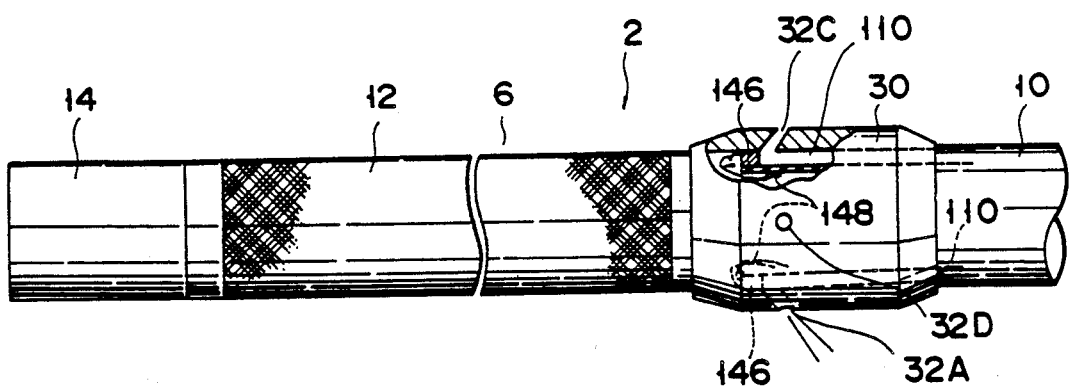
F I G. 52
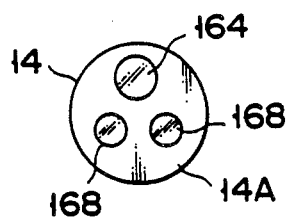
F I G. 53
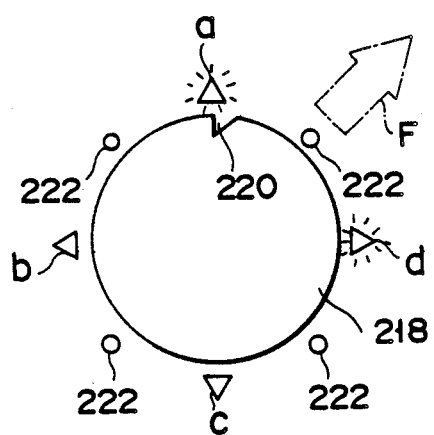
F I G. 54
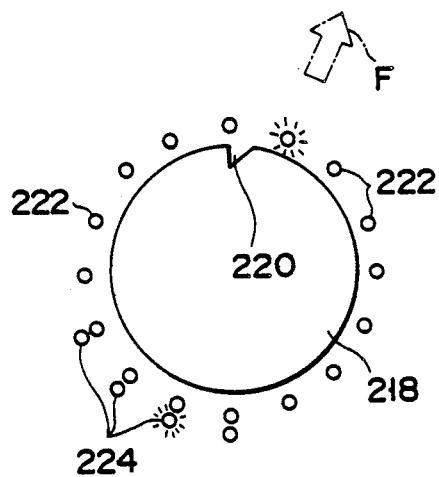
F I G. 55

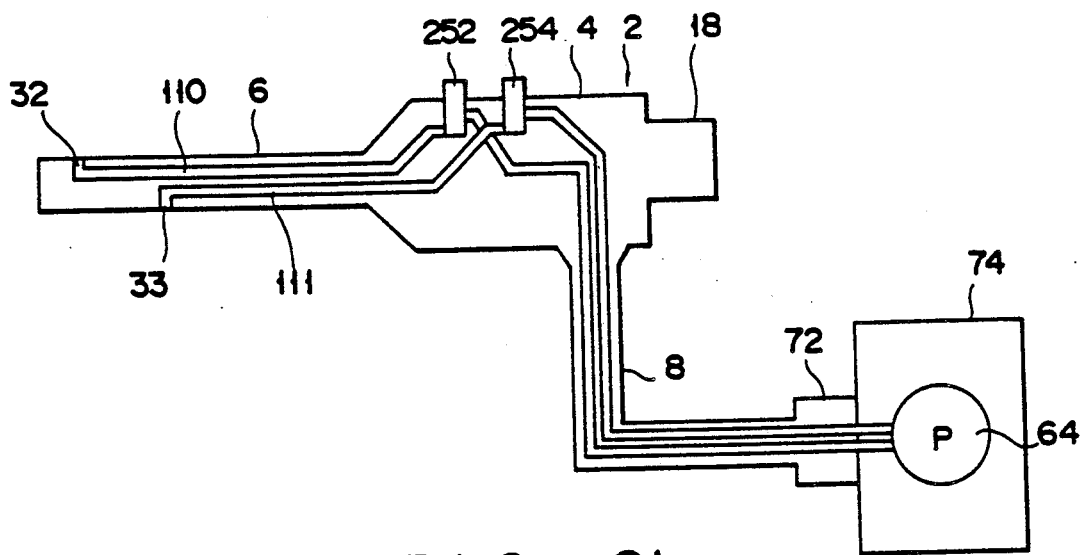
F I G. 61
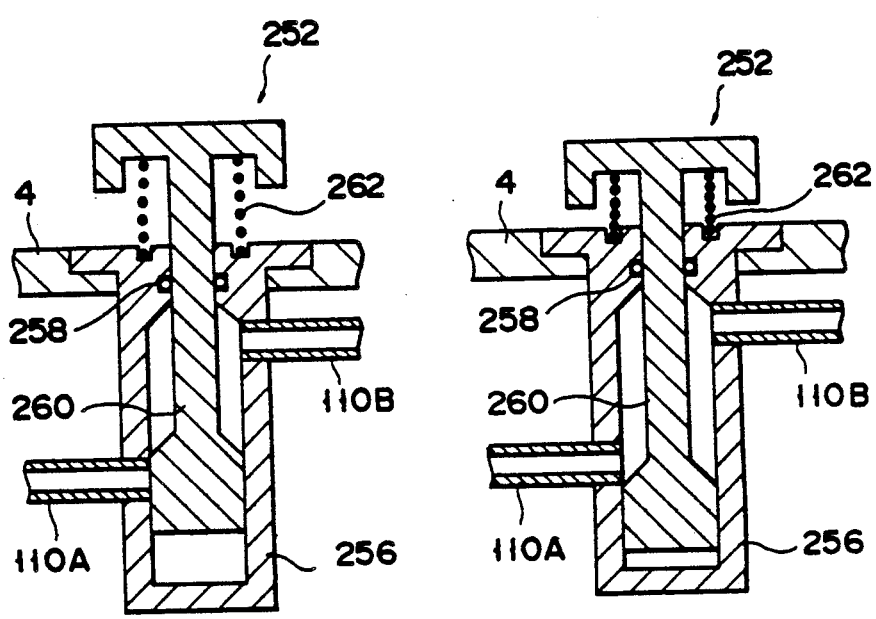
F I G. 62    F I G. 63

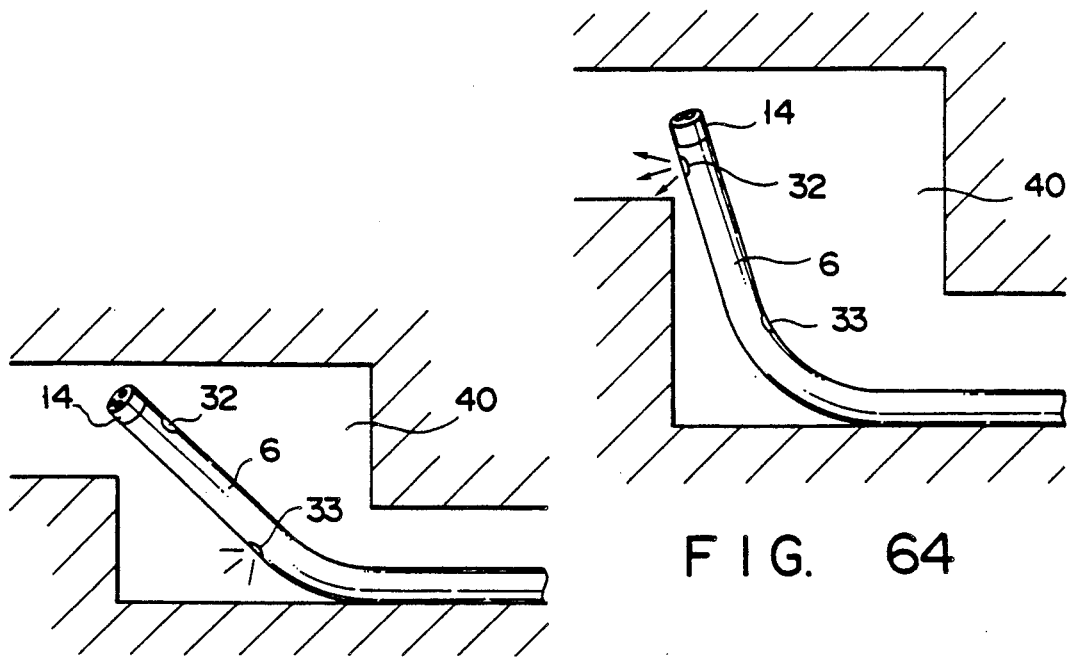
FIG. 64
FIG. 65
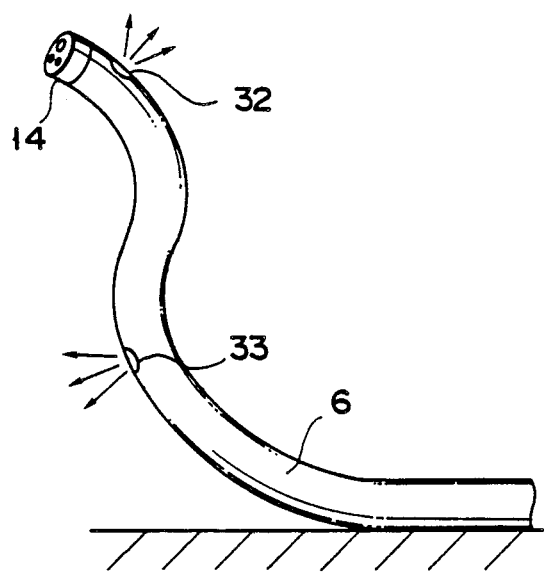
FIG. 66

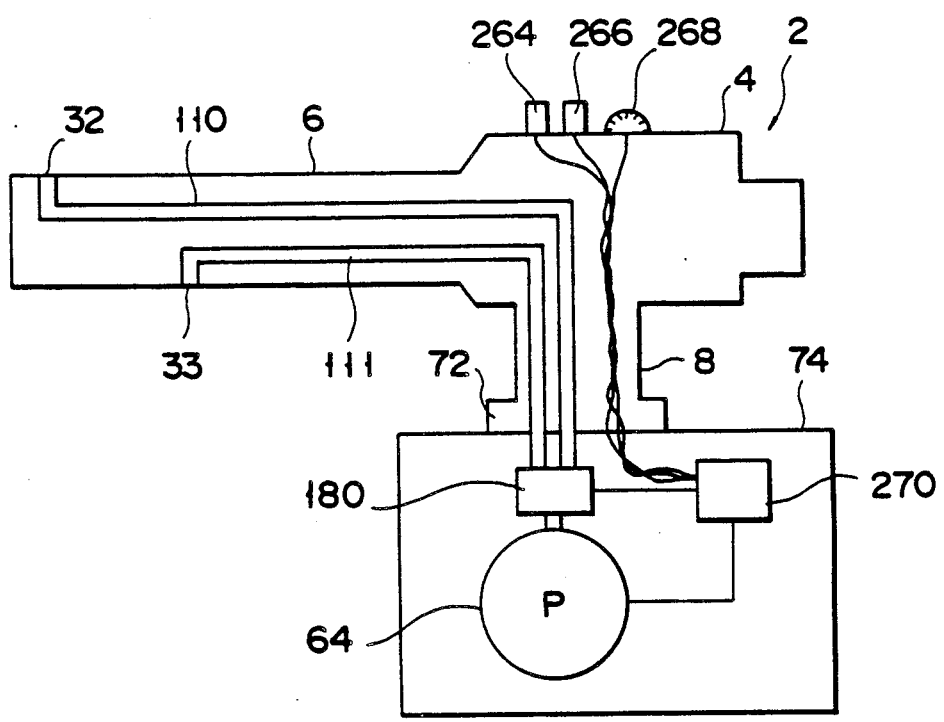
F I G. 71

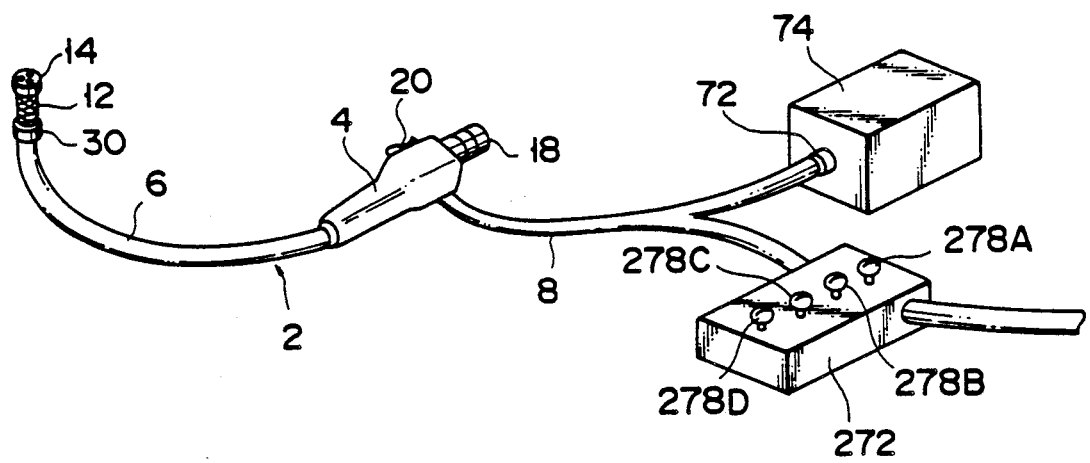
F I G. 72
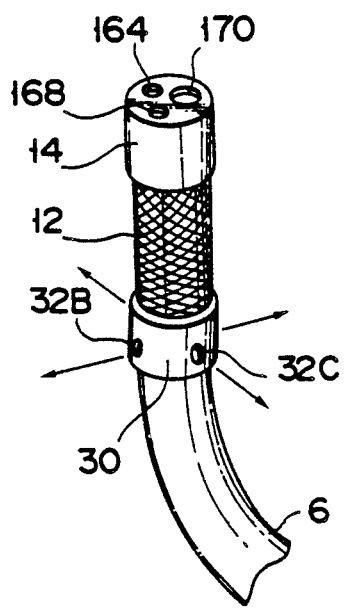
F I G. 73
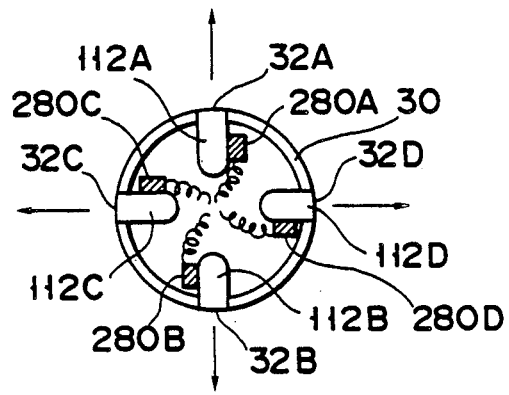
F I G. 74

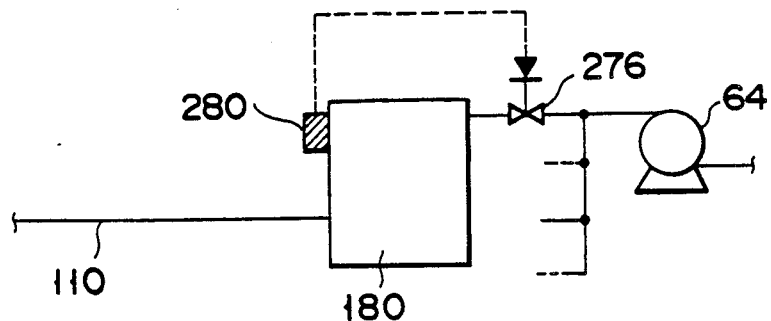
F I G. 75
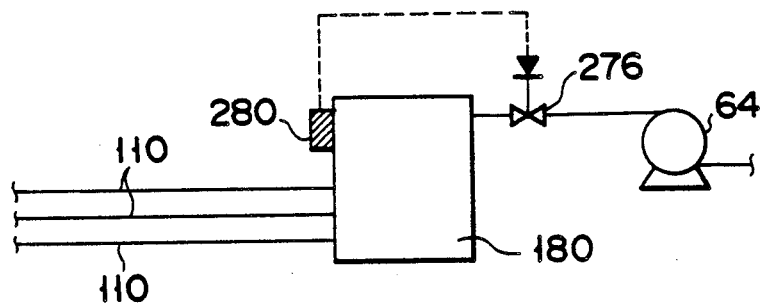
F I G. 76
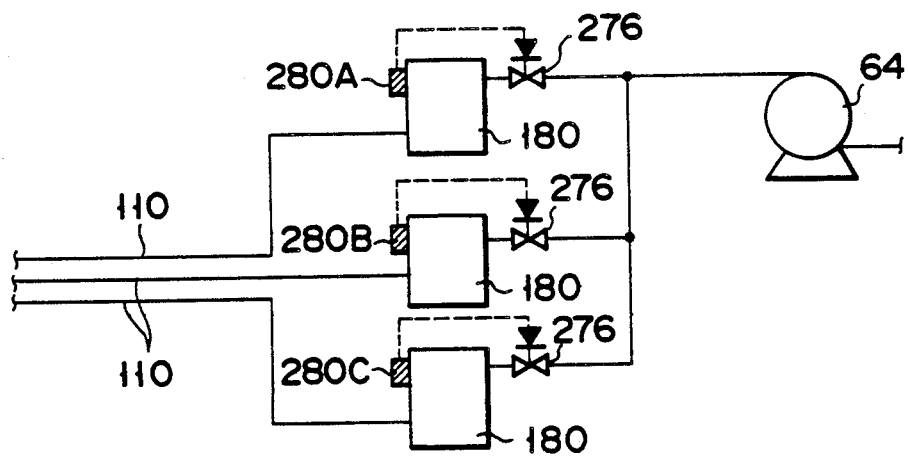
F I G. 77

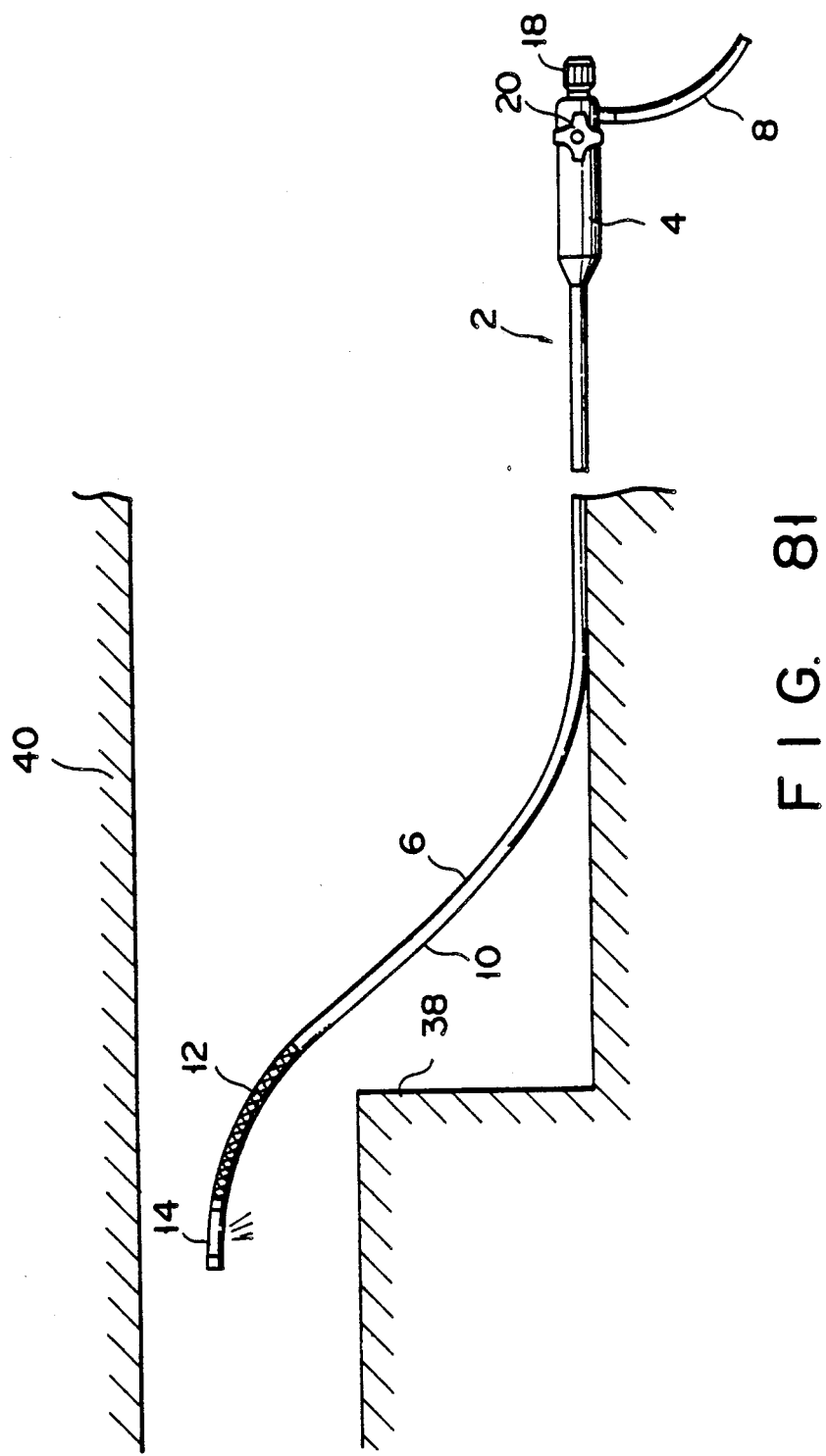

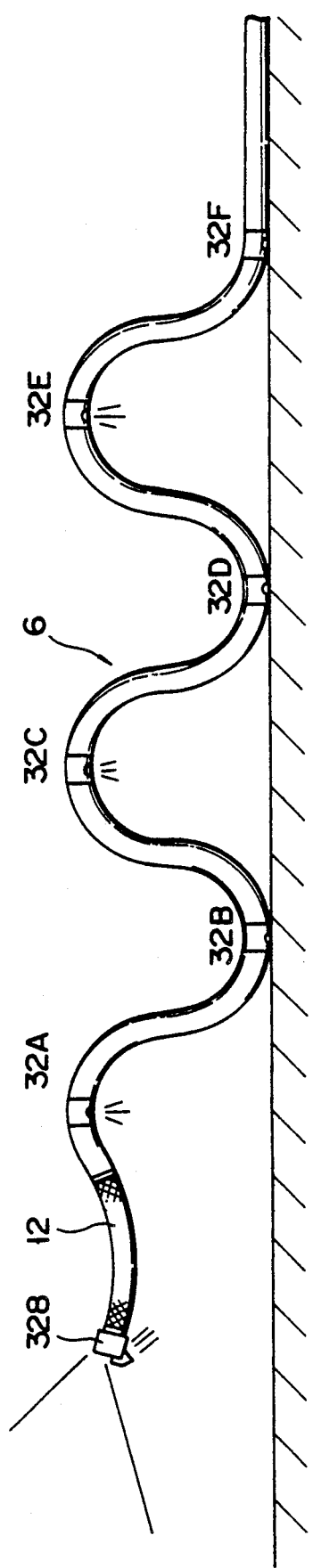
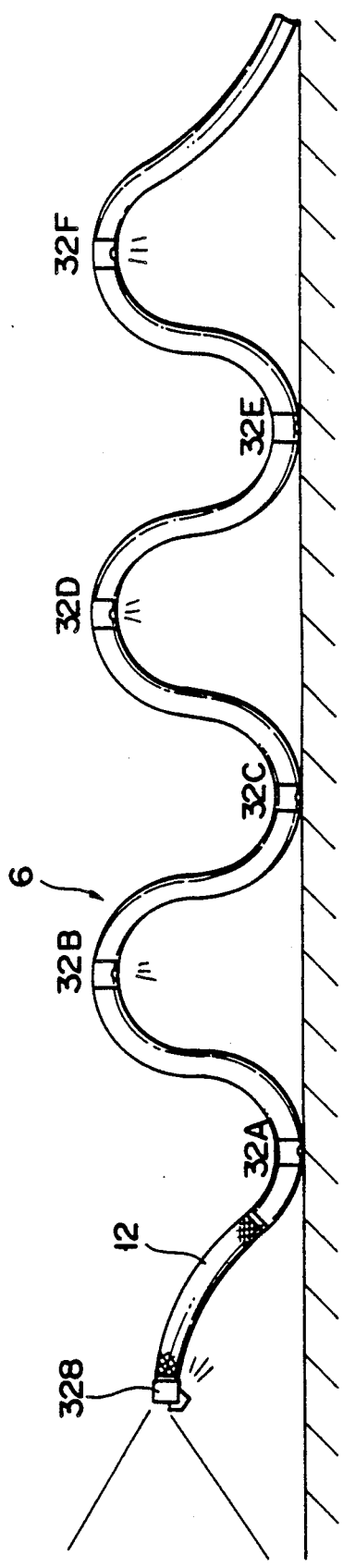
FIG. 93
FIG. 94

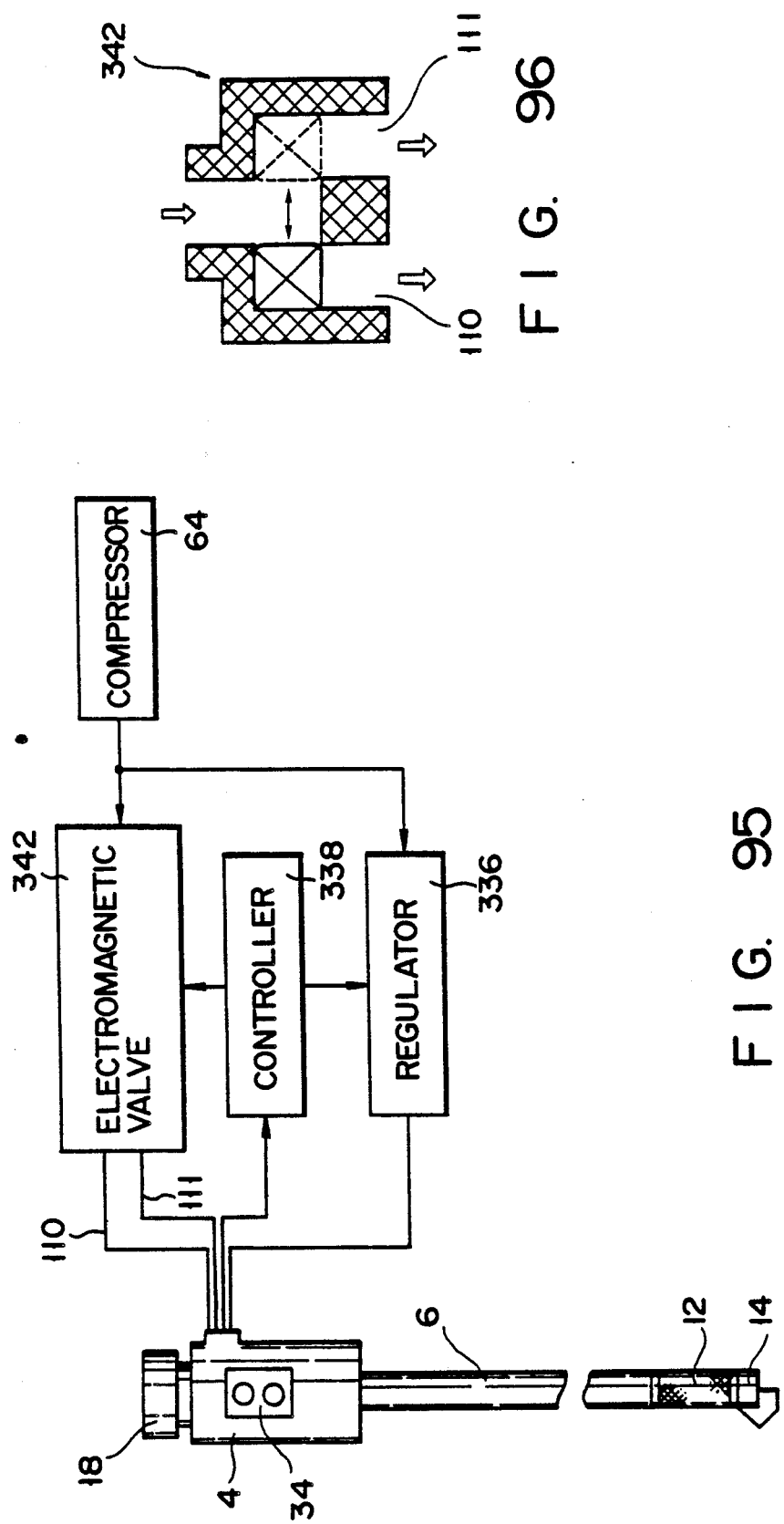

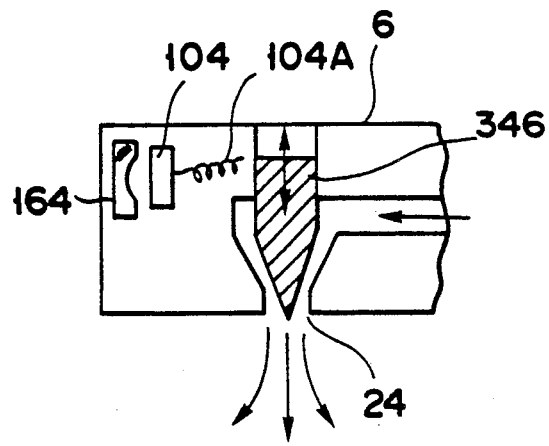
F I G. 97
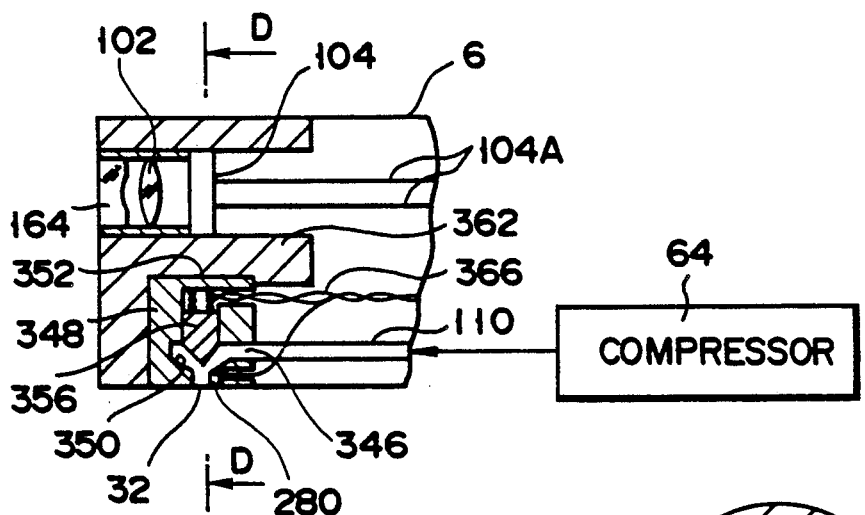
F I G. 98
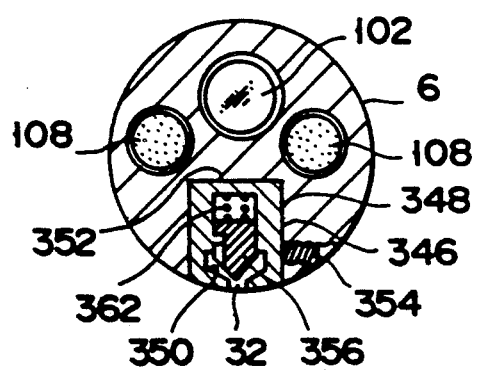
F I G. 99

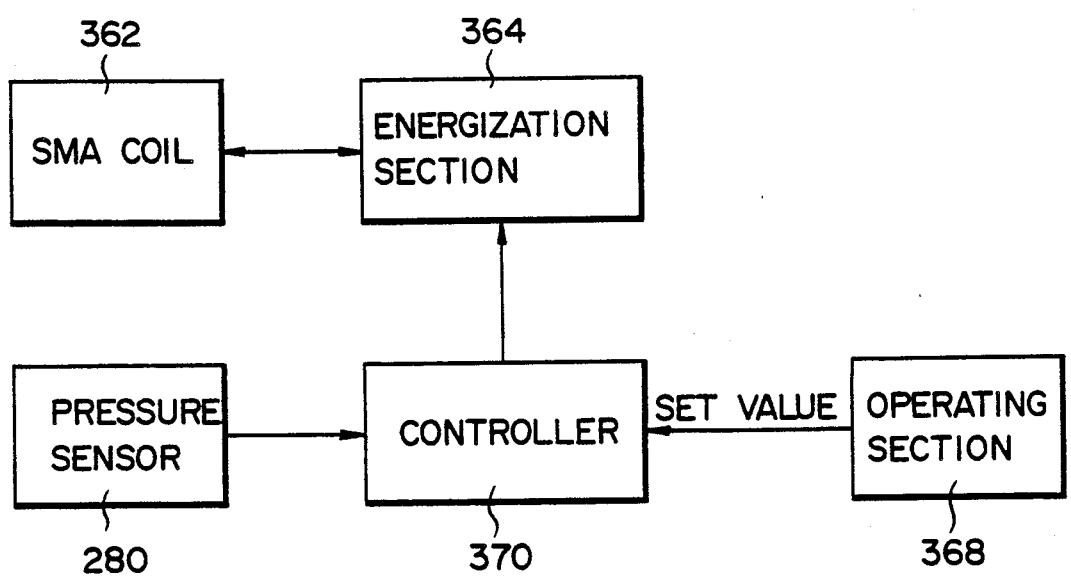
F I G. 100

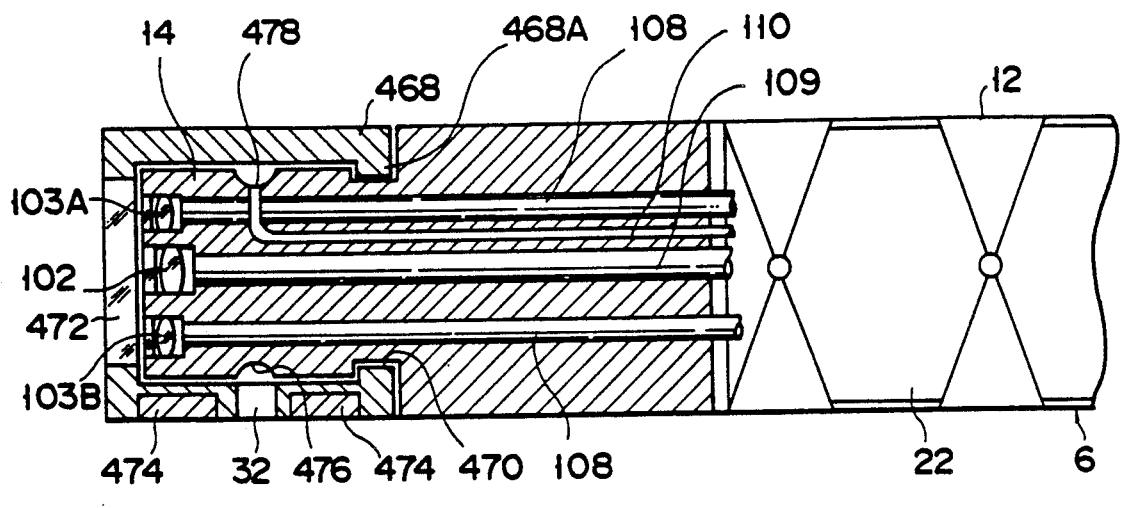
FIG. 140
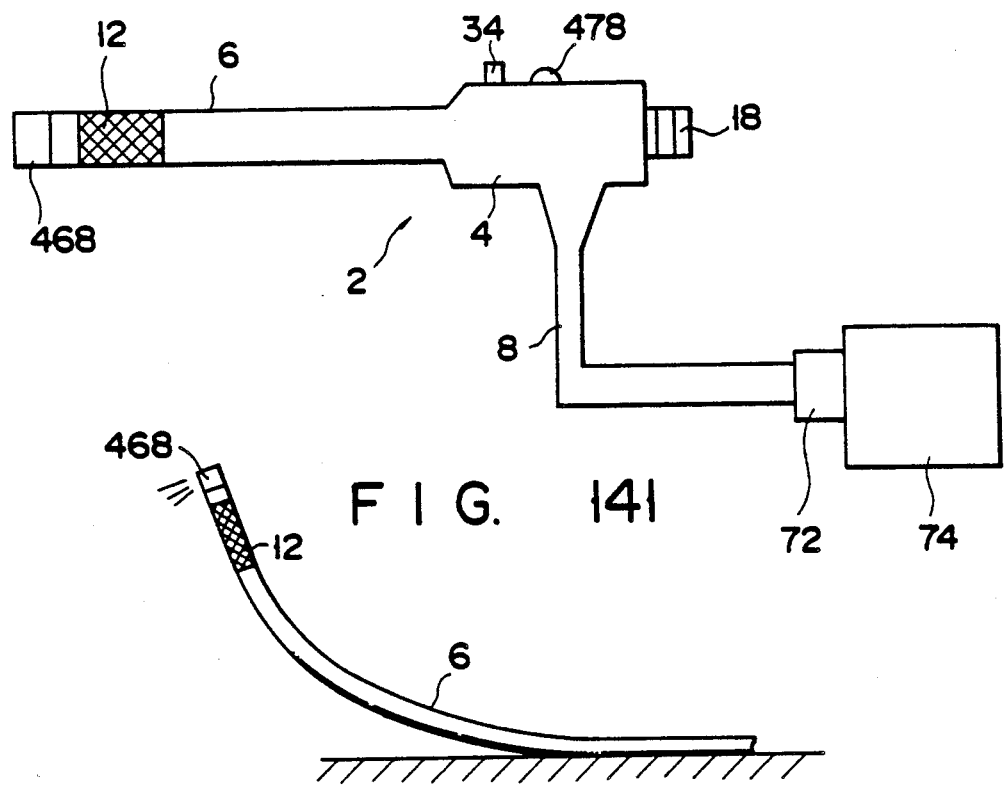
FIG. 141
FIG. 142

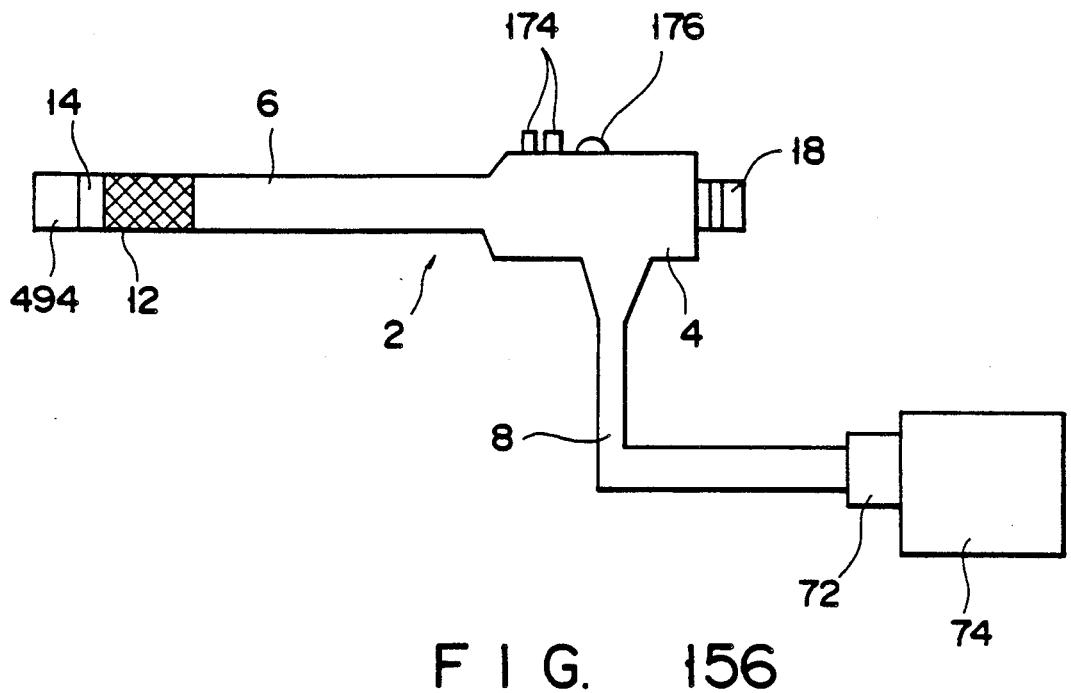
F I G. 156
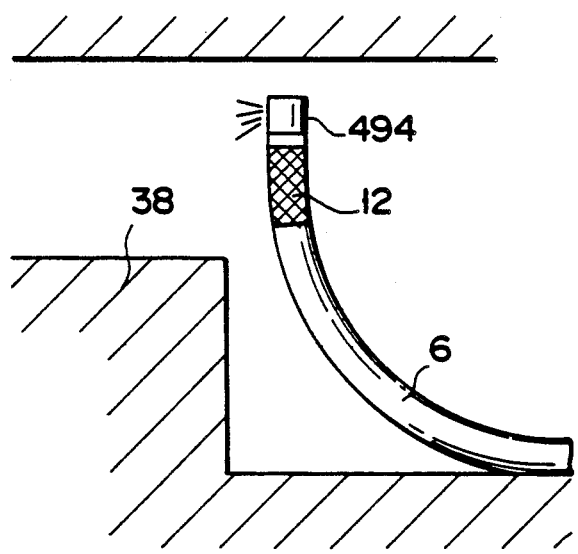
F I G. 157

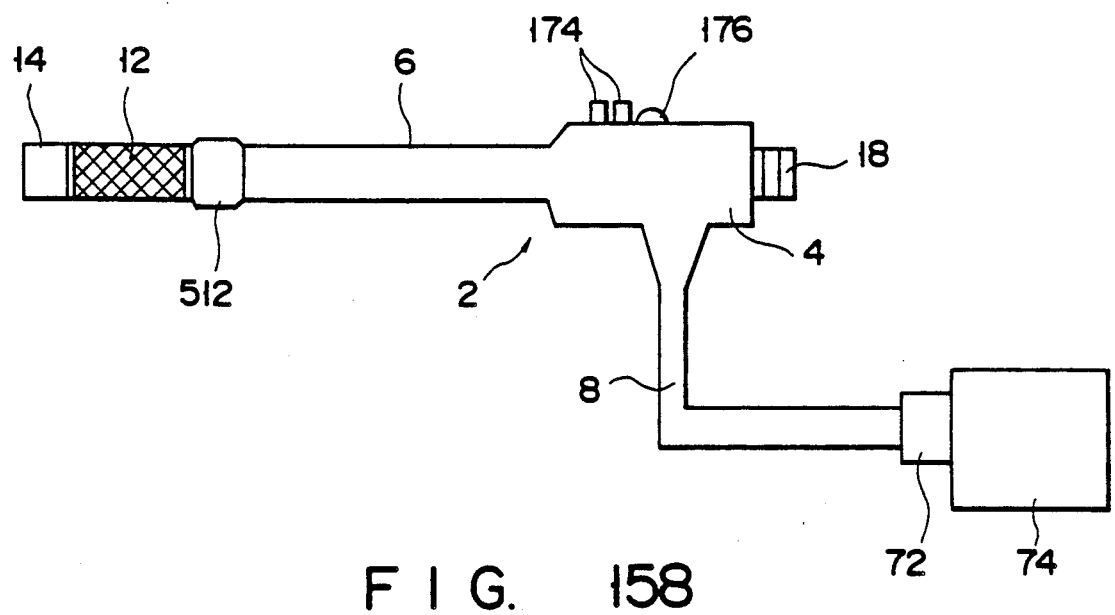
F I G. 158
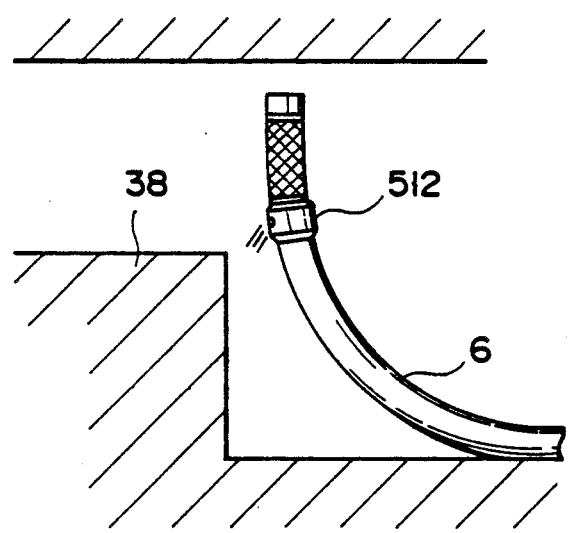
F I G. 159

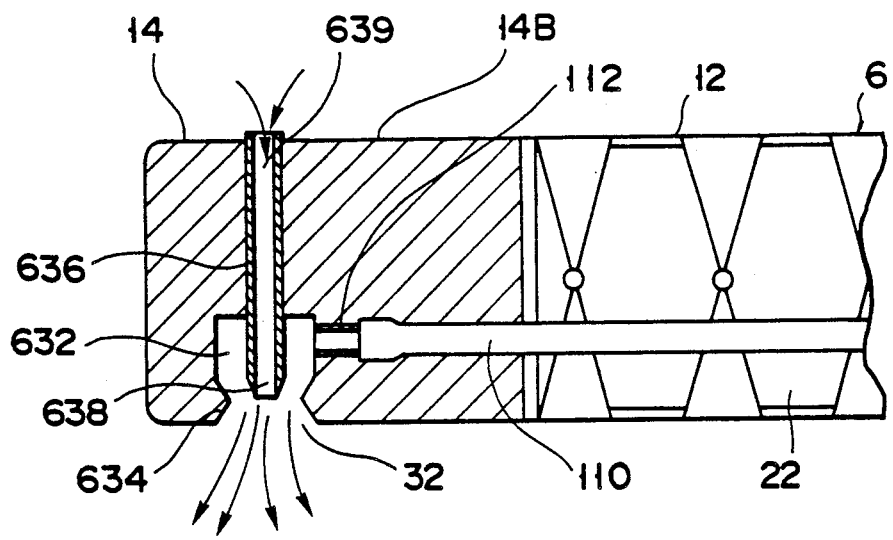
F I G. 173
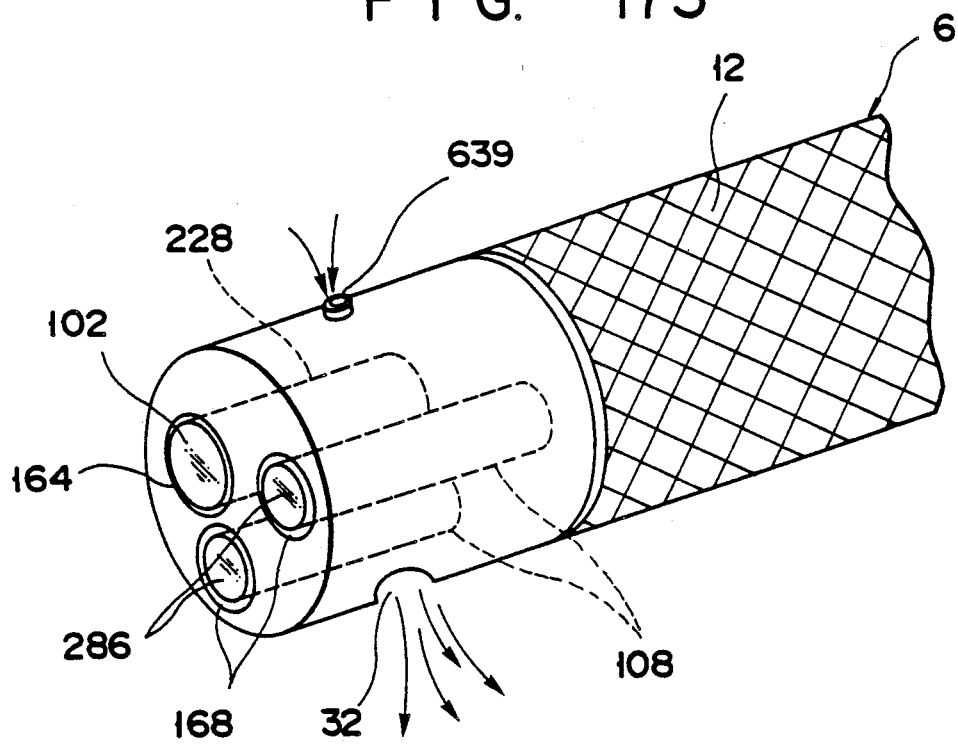
F I G. 174

BORESCOPE APPARATUS

BACKGROUND OF THE INVENTION

1. Field of the Invention

This invention relates to a borescope apparatus comprising a borescope with an insertion unit having fluid jet ports and a pressurized fluid supply unit for supplying pressurized fluid to the jet ports.

2. Description of the Related Art

A conventional endoscope or borescope includes an insertion unit having flexibility. The insertion unit can be inserted into cavities having various shapes by making use of the flexibility of the insertion unit for observation of the inside. However, there is a limitation on the scope of use. More specifically, since the insertion unit is soft, it can not support its own weight, so that it is impossible to observe a ceiling wall or advance it beyond a large stepped wall. Therefore, the prior art borescope is inconvenient for the observation of wall surfaces of a cavity having a narrow inlet and a wide inner space or inside of an air conditioner duct, and it can not be utilized for these fields. In order to insert the insertion unit of the borescope into a cavity having a narrow inlet and a wide inner space, a hard or semi-hard pipe is utilized as an auxiliary tool. However, since different cavities, into which the borescope insertion unit is to be inserted, have different shapes, a variety of different auxiliary tools are necessary.

U.S. Pat. No. 4,735,501 discloses a borescope in which compressed air is jetted obliquely rearward through a jet port provided in the distal end of the insertion unit, thereby to move the entire unit. Since the jet port is made in the distal end of the insertion unit, it is therefore difficult for the operator to orientate the distal end in a desired direction. The borescope has means for controlling the fluid. However, the U.S. Patent specification is silent as to what structure this means has to improve the operability of the borescope.

If the inside of a cavity having a narrow inlet and a wide inner space is to be inspected with such a usual borescope, an auxiliary tool for assisting the insertion is necessary for the borescope does not have any support for itself. Further, the observation and inspection with the borescope are difficult for the inside of a ceiling of a building, into which the insertion unit has to be inserted upwards against the gravitational force, or a place with a large stepped wall to be cleared by the inserted insertion unit such as the inside of an air conditioner duct.

SUMMARY OF THE INVENTION

An object of the invention is to provide a borescope apparatus, with which the insertion unit of the borescope can be inserted readily and reliably into even deep and complicated cavities.

An object of the invention can be attained by a borescope apparatus, which comprises a borescope including an operation unit and an insertion unit, the insertion unit having a bending tube portion capable of being curved by the operation unit, a jet port member connected to a proximal end of the bending tube portion and having a jet port for jetting a fluid and a flexible tube portion connected to the jet port member and curved independently of the bending tube portion by fluid jet from the jet port of the jet port member, pressurized fluid being supplied from the pressurized fluid supply unit to the jet port of the insertion unit to be jet out from the jet port.

According to the invention, there is also provided a borescope apparatus, which comprises an operation unit, an insertion unit having a jet port for jetting fluid, a pressurized fluid supply unit for supplying pressurized fluid to a jet port of the insertion unit to be jet out from the jet port and a control device provided in the operation unit for operating the insertion unit under remote control through regulation of pressurized fluid supplied to the jet port.

With the borescope apparatus according to the invention, the insertion unit of the borescope can be readily inserted into even complicated cavities, which requires auxiliary tools for the insertion of the prior art borescope insertion unit, with a pressurized fluid supply unit. Thus, it is possible to obtain improved operability and extend the scope of use of the borescope.

Further, since the insertion unit can be inserted without need of any auxiliary tool into a complicated cavity, it is possible to make full use of the flexibility of the insertion unit of the borescope.

Further, since the operation unit has a reversible structure, any person can operate the angle knob and the pressure control means at the same time, no matter whether he or she is left-handed or right-handed. A right-handed person operates the angle knob with the right hand, while operating the pressure control means with the left hand. A left-handed person operates the angle knob with the left hand, while operating the pressure control means with the right hand. Thus, the operation time is reduced, and the operator can find the object of examination quickly.

BRIEF DESCRIPTION OF THE DRAWINGS

FIGS. 11 and 12 are side views showing a fourth modification of the insertion unit of the first embodiment of the borescope;

FIG. 15 is a side view showing a second embodiment of the borescope according to the invention;

FIG. 25 is a schematic side view showing a third embodiment of the borescope according to the invention;

FIG. 26 is a perspective view showing an end structure of the insertion unit shown in FIG. 25;

FIG. 32 is a perspective view showing an end portion of a third modification of the insertion unit;

FIG. 33 is a perspective view showing a fourth embodiment of the insertion unit;

FIGS. 34 to 36 are perspective views showing for explaining the use of the third modification of of the borescope;

FIG. 37 is a block diagram showing a fourth embodiment of the borescope according to the invention;

FIG. 38 is a schematic sectional view showing a changeover valve of the borescope shown in FIG. 37;

FIG. 39 is a schematic side view, partly broken away, showing a fourth embodiment of the borescope according to the invention;

FIGS. 40 and 41 are perspective views showing a distal end portion of an insertion unit shown in FIG. 39;

FIGS. 42 and 43 are side views showing an end portion of a process tool;

FIGS. 44 to 47 are sectional views showing modifications of a seal member;

FIG. 52 is a side view showing an insertion unit of a fifth embodiment of the borescope according to the invention;

FIG. 53 is a front view showing the insertion unit shown in FIG. 53;

FIG. 54 is a schematic view showing an observation field section of the fifth embodiment of the borescope;

FIG. 55 is a schematic view showing a first modification of the observation field section;

FIG. 61 is a schematic side view showing a sixth embodiment of the borescope according to the invention;

FIGS. 62 and 63 are sectional views showing a changeover valve in the sixth embodiment of the borescope;

FIGS. 64 to 66 are sectional views for explaining the use of the sixth embodiment of the borescope;

FIG. 71 is a schematic view showing a different modification of the sixth embodiment of the borescope;

FIG. 72 is a perspective view showing a seventh embodiment of the borescope according to the invention;

FIG. 73 is a perspective view showing an end structure of the insertion unit shown in FIG. 72;

FIG. 74 is a transversal sectional view showing a jet port section shown in FIG. 73;

FIG. 75 is a block diagram showing the seventh embodiment of the fluid supply unit;

FIG. 76 is a block diagram showing a first modification of the fluid supply unit;

FIG. 77 is a block diagram showing a second modification of the fluid supply unit;

FIG. 81 is a perspective view for explaining the use of the eighth embodiment of the borescope;

FIGS. 93 and 94 are side views for explaining the use of a second modification of the borescope;

FIG. 95 is block diagram showing a third modification of the ninth embodiment of the borescope;

FIG. 96 is a schematic view showing a changeover valve in a third modification;

FIGS. 97 and 98 are schematic side views showing an end structure of an insertion unit in a tenth embodiment of the invention;

FIG. 99 is a transversal sectional view taken along line D—D in FIG. 98;

FIG. 100 is a block diagram showing a control circuit in the tenth embodiment of the borescope;

FIGS. 140 and 142 are respectively a longitudinal sectional view and a side view showing an insertion unit of a third modification of the borescope;

FIG. 141 is a schematic side view showing a third modification of the borescope;

FIG. 156 is a schematic view showing a second modification of the borescope;

FIG. 157 is a side view showing an operating state of an insertion unit of a second modification of the borescope;

FIG. 158 is a schematic view showing a third modification of the borescope;

FIG. 159 is a side view showing an operating state of an insertion unit of the third modification of the borescope;

FIG. 164 is a side view showing an insertion unit of the fourteenth embodiment of the borescope;

FIGS. 165 and 166 are perspective views showing an operating state of the insertion unit;

FIG. 167 is a side view, partly broken away, showing an operation unit in a modification of the fourteenth embodiment;

FIG. 168 is a fragmentary sectional view showing a modification of an electromagnetic valve;

FIGS. 169 and 170 are a fragmentary sectional view and a perspective view showing an end structure of an insertion unit in a fifteenth embodiment of the borescope;

FIG. 171 is a side view showing an operating state of the fifteenth embodiment of the borescope;

FIG. 172 is a fragmentary sectional view showing an insertion unit in a first modification of the fifteenth embodiment;

FIGS. 173 and 174 are respectively a longitudinal sectional view and a perspective view showing an insertion unit in a second modification of the fifteenth embodiment;

FIG. 175 is a longitudinal sectional view showing an insertion unit in a third modification;

FIG. 176 is a side view showing an operating state of a fourth modification of the borescope;

FIGS. 177 and 178 are respectively a longitudinal sectional view and a perspective view showing an insertion unit of the fourth embodiment;

FIG. 179 is a schematic view showing an insertion unit of a sixteenth embodiment of the borescope according to the invention;

Figure 179:
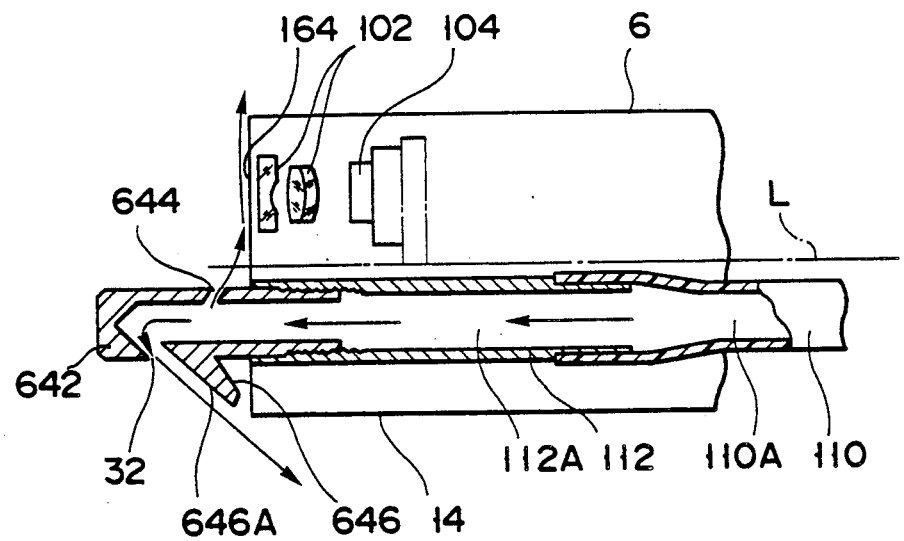
Figure 180:
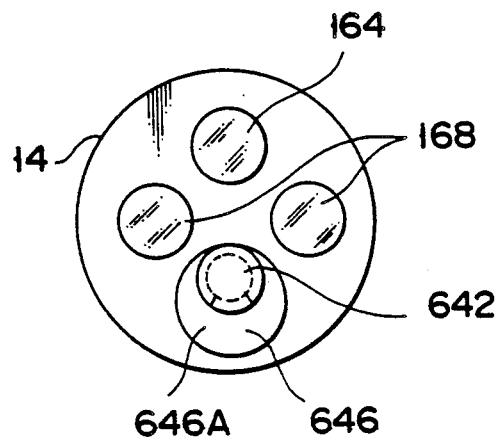
Figure 181:
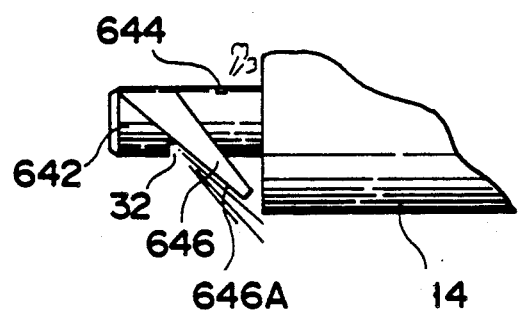
Figure 182:
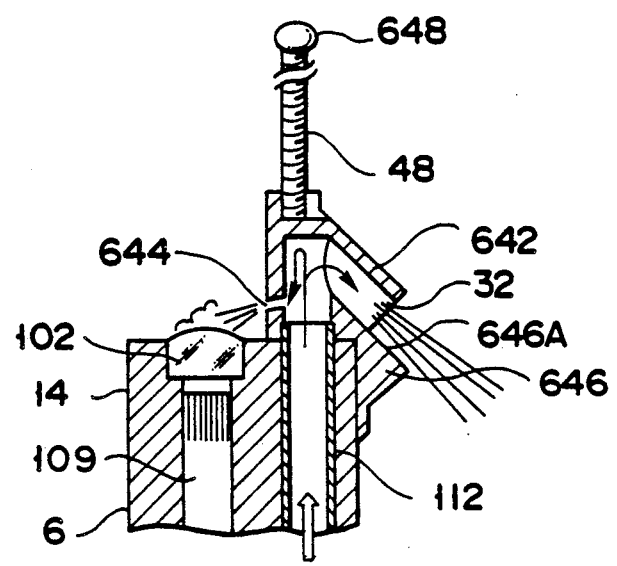
Figure 183:
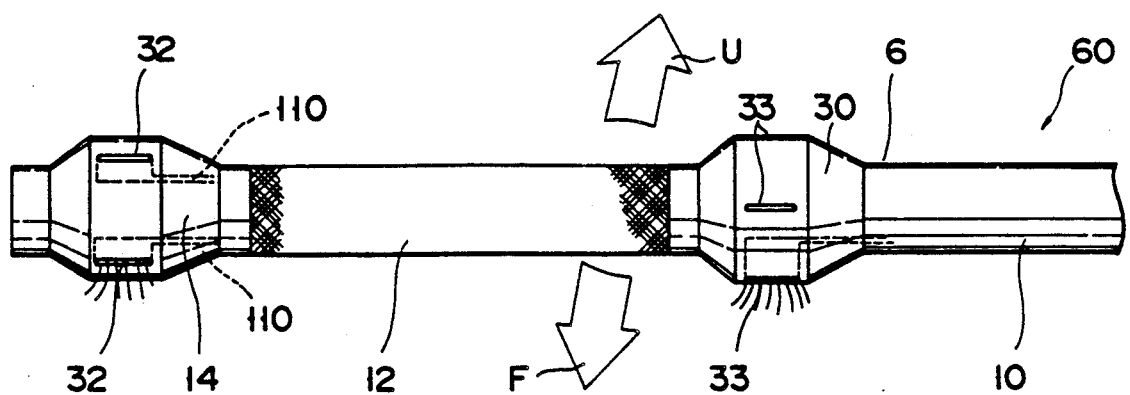
Figure 184:
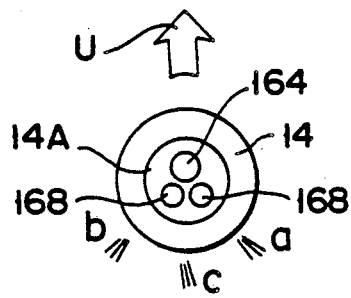

FIG. 180 is a front view showing an insertion unit shown in FIG. 179;

FIG. 181 is a side view showing an end structure of the insertion unit shown in FIG. 179;

FIG. 182 is a longitudinal sectional view showing an insertion unit in a modification of the sixteenth embodiment;

FIG. 183 is a side view showing an insertion unit of a seventeenth embodiment of the borescope according to the invention; and FIG. 184 is a front view showing the insertion unit shown in FIG. 183.

DETAILED DESCRIPTION OF THE PREFERRED EMBODIMENTS

Figure 1:
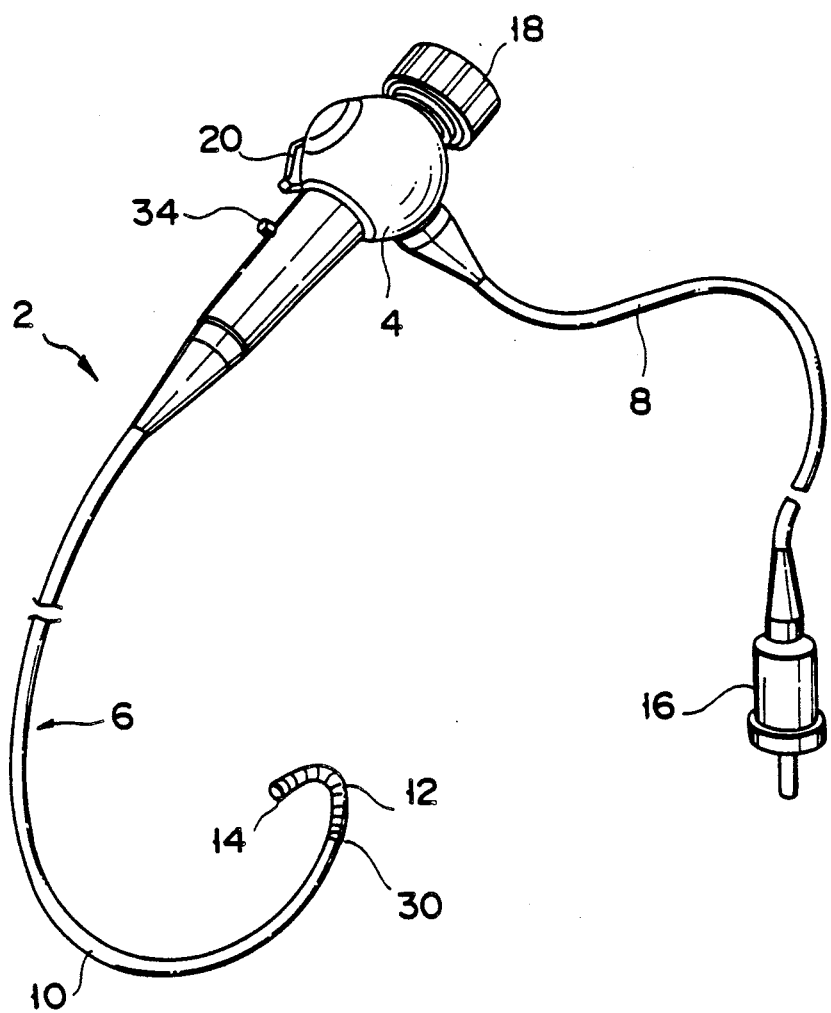
FIG. 1 is a side view showing a first embodiment of the borescope apparatus according to the invention.
Figure 2:
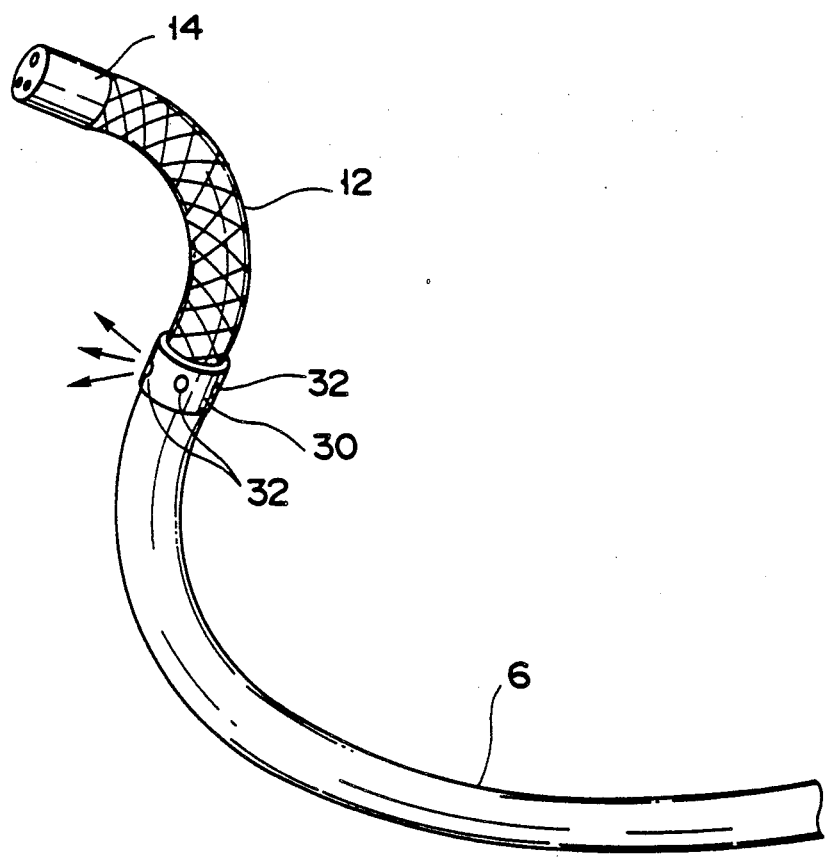
FIG. 2 is a perspective view showing an insertion unit of the borescope shown in FIG. 1.
Figure 3:
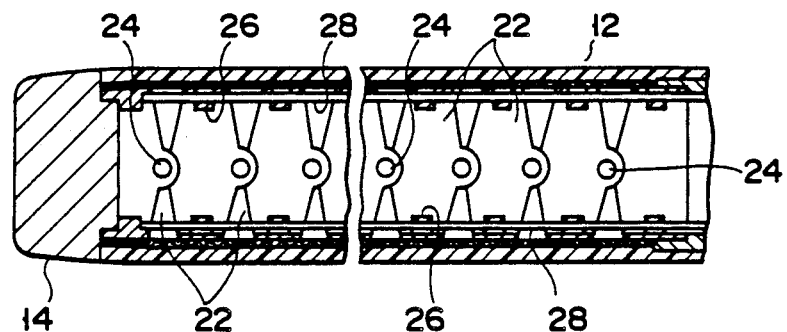
FIG. 3 is a sectional view showing a flexible end portion of the borescope shown in FIG. 1.

A first embodiment of the invention will now be described with reference to FIGS. 1 to 3. FIG. 1 shows borescope or endoscope 2 having operation unit 4. Insertion unit 6 and universal cord 8 are connected to operation unit 4. Insertion unit 6 consists of flexible tube 10. Flexible tube 10 has bending portion or flexible end portion 12, which serves as a first curving mechanism and has end structure 14 provided at the distal end. Connector 16 is provided at the other end of universal cord 8. Connector 16 is to be connected to a light source unit (not shown).

Operation unit 4 is provided with eyepiece unit 18 and knob 20, and bending portion 12 can be operated under remote control by knob 20. Bending portion 12, as shown in FIG. 3, includes a train of elements 22 rotatably coupled to one another by shafts 24. The inner surface of each element 22 is provided with short guide tubes 26 circumferentially spaced apart by 180 degrees. Operation wires 28 are passed through guide tubes 26. Operation wires 28 have their ends coupled to element 22 at the distal end, and they are led to operation unit 4 and coupled to knob 20. Operation wires 28 can be pushed and pulled by knob 20. Bending portion 12 can be curved with operation wires 28 pushed or pulled by knob 20.

At the stem of bending portion 12 of insertion unit 6 a jet port member 30 constituting a second curving mechanism is provided. Jet port member 30 has four jet ports 32 formed at an interval of 90 degrees in the circumferential direction. To each jet port 32 an end of an air supply tube (not shown) is connected. These air supply tubes are led through operation unit 4 and universal cord 8 to be connected to connector 16. When connector 16 is connected to the light source unit, the air supply tubes are connected to an air supply pump (not shown) provided in the light source unit. Thus, air under high pressure can be forced out from the air supply pump through the air supply tubes to be jet out from jet ports 32 of jet port member 30. Operation unit 4 has control switch 34 for controlling the start and stop of the air supply pump and also the direction of jetting of the high pressure air.

Figure 4:
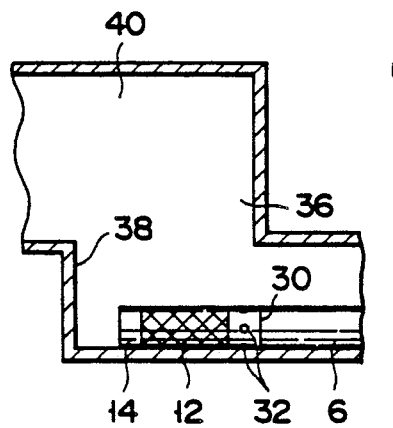
FIGS. 4 to 6 show side views showing the insertion unit of the borescope inserted into a piping.
Figure 5:
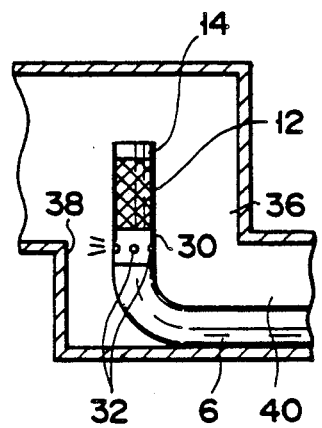
Figure 6:
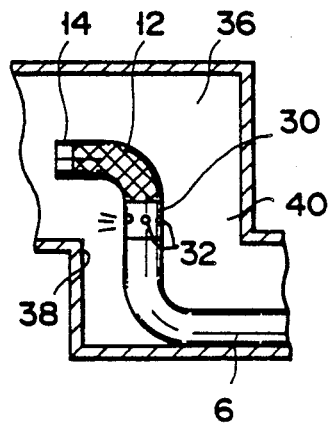

The endoscope as described above may be used for the inspection or observation of plant piping having large diameter portion 36 and stepped portion 38, as shown in FIGS. 4 and 6. More specifically, if it is desired to observe the top of the inside of large diameter portion 36 of piping 40, insertion unit 6 is inserted up to the bottom of large diameter portion 36. Then, the air supply pump provided in the light source unit (not shown) is operated by operating control switch 34 provided in operation unit 4, thus causing high pressure air generated from the air supply pump to be jet from jet port 32 corresponding to the lower inner wall surface of large diameter portion 36. Thus, reaction force produced by the high pressure air jet from jet port 32 acts on jet port member 30 of insertion unit 6, so that a portion of insertion unit 6 on the side of jet port member 30 opposite bending portion 12 is curved as shown in FIG. 5. Thus, a portion of insertion unit 6 sufficiently longer than bending portion 12 becomes upright, so that end structure 14 can be brought to a position close to the top inner surface of large diameter portion 46 of piping 40. The piping inside thus can be observed satisfactorily.

If it is desired to observe a portion of piping 40 ahead of stepped wall 38 of large diameter portion 36, bending portion 12 is curved from the state shown in FIG. 5 to the state shown in FIG. 6, thus bringing end structure 14 to be ahead of stepped wall 38. This is done by operating knob 20. Now, the portion of piping ahead of stepped wall 38 can be observed.

It is to be appreciated that with endoscope 2 having the above construction insertion unit 6 can be curved with a large radius of curvature by the jet from the jet port for its portion on the side of jet port member 30 opposite bending portion 12, and also bending portion 12 itself can be curved in stable condition. It is thus possible to bring the distal end of insertion unit 6 to be close to the top inner wall surface of large diameter piping 40 so as to obtain satisfactory observation. Also, a portion of the piping inside ahead of stepped wall 38 can be satisfactorily observed.

Figure 7:
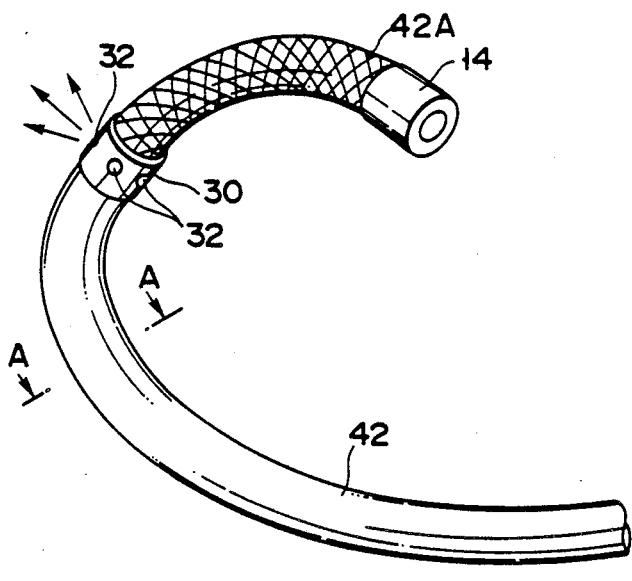
FIG. 7 is a perspective view showing a first modification of the insertion unit of the first embodiment.
Figure 8:
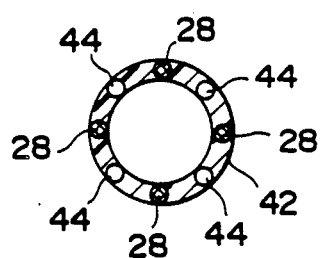
FIG. 8 is a sectional view taken along line A—A in FIG. 7.

FIGS. 7 and 8 show a first modification of the first embodiment. In this instance, insertion unit 6 is guided by guide tube 42 as flexible tube of the endoscope. Like the preceding first embodiment, guide tube 42 has bending portion 42A, at the stem of which jet port member 30 with jet ports 32 is provided. In the peripheral wall of guide tube 42, as shown in FIG. 8, four operation wires 28 for curving bending portion 42A are provided slidably in the axial direction and disposed at a circumferential interval of 90 degrees, and likewise air supply passages 44 for supplying high pressure air to four jet ports 32 of jet port member 30 are provided.

With this structure, guide tube 42 can be curved with a large radius of curvature and also in two stages. Thus, by inserting insertion unit 6 of the endoscope in guide tube 42, it can be inserted into a complex piping by guide tube 42.

Figure 9:
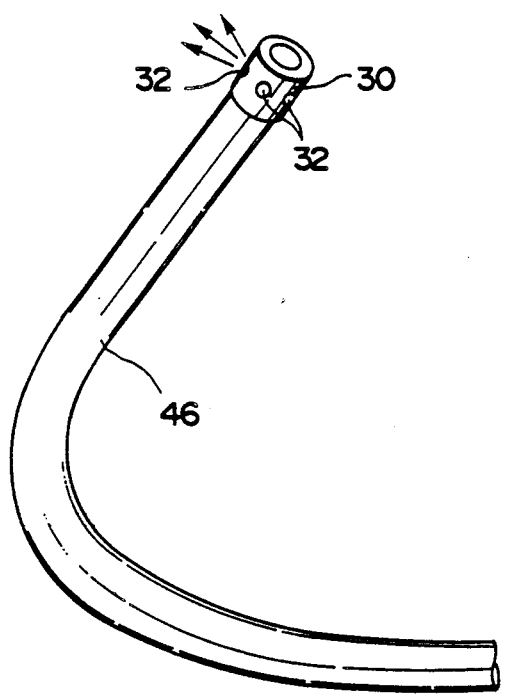
FIG. 9 is a perspective view showing a second modification of the insertion unit of the first embodiment of the borescope.

FIG. 9 shows a second modification of the first embodiment. This instance concerns guide tube 46, which is provided at the distal end solely with jet port member 30 with jet ports 32. By inserting typical endoscope insertion unit 6 including bending portion 12 alone, unit 6 may be curved with a large radius of curvature and also in two stages as in the case of the first embodiment with the curving function of insertion unit 6 and that of guide tube 46.

It is possible to use a liquid or such gas as CO gas in lieu of the compressed air depending on the place where the insertion unit is inserted.

Figure 10:
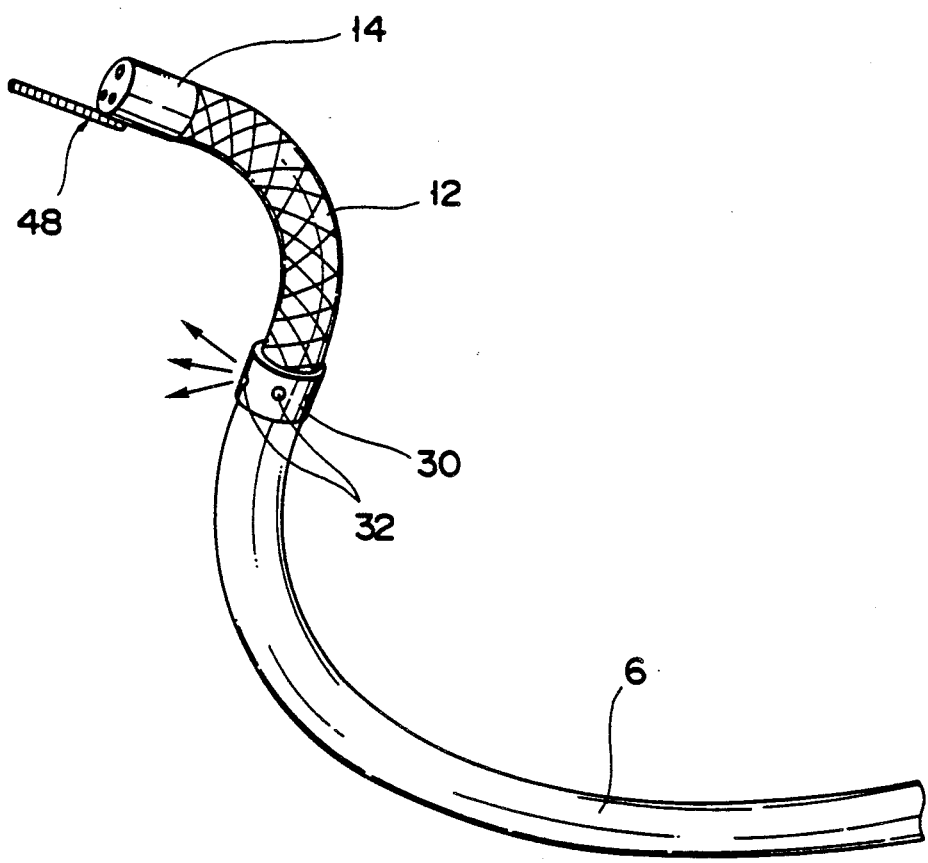
FIG. 10 is a perspective view showing a third modification of the insertion unit of the first embodiment of the borescope.

FIG. 10 shows a third modification. In this modification, antenna guide 48 extends forwardly from end structure 14 so as to be able to maintain a constant distance between the subject of observation and end structure 14, and obtain a stable observation image. Antenna guide 48 has a suitable flexibility, and it can facilitate the insertion of insertion unit 6.

FIGS. 11 and 12 show a fourth modification. In this instance, jet port member 30 is provided at the distal end of insertion unit 6 of the endoscope. Further, flexible end portion 12 is provided as an intermediate portion of insertion unit 6. First flexible tube 50 without any outer blade is provided between jet port member 30 and flexible end portion 12. On the side of flexible end portion 12 opposite first flexible tube 50, there is provided second flexible tube 52 with fluorine-contained rubber impregnated outer blade. Bend stop section 54 is connected to the stem of second flexible tube 52.

Figures 13, 14:
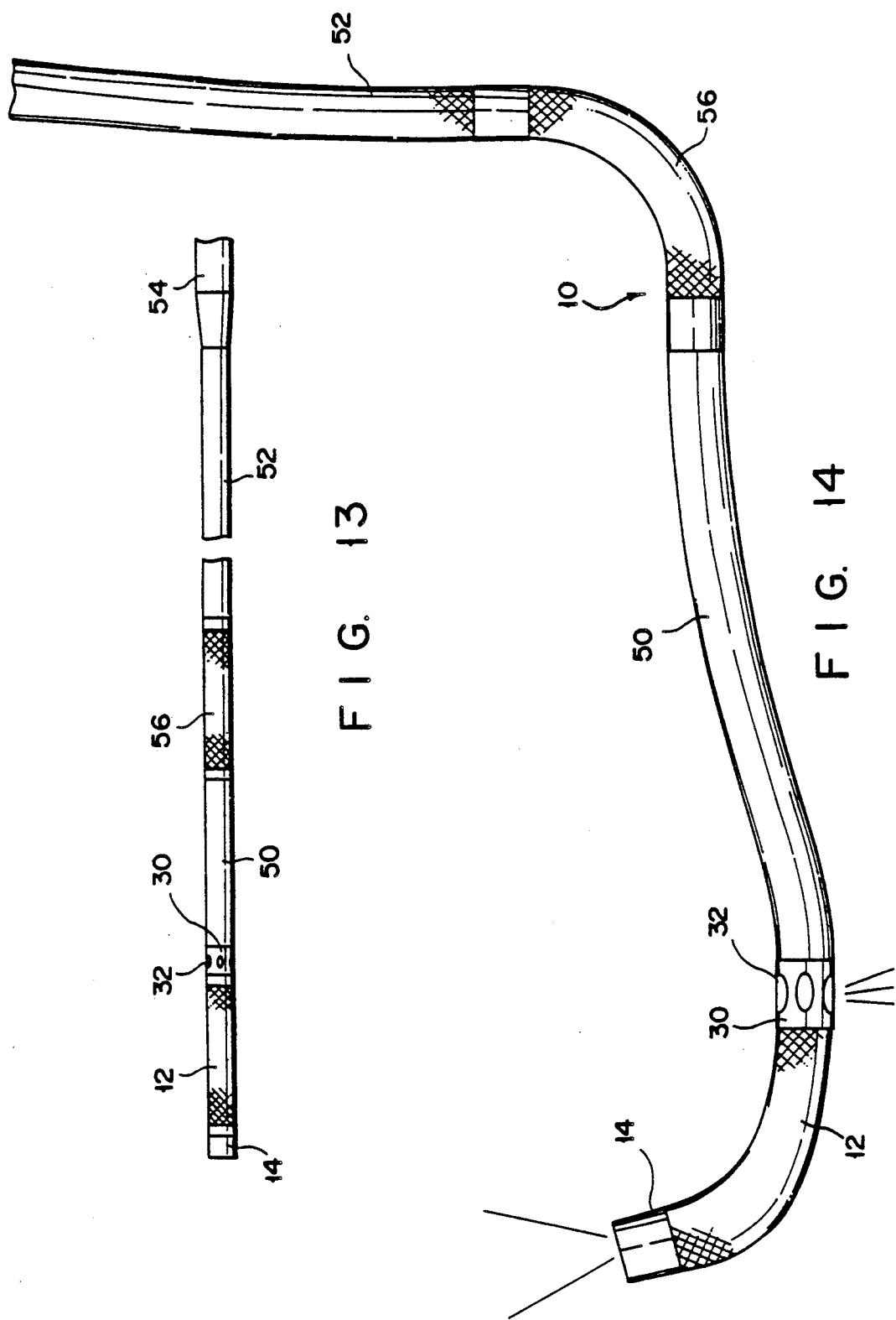
FIGS. 13 and 14 are side views showing a fifth modification of the insertion unit of the first embodiment of the borescope.

FIGS. 13 and 14 show a fifth modification. In this instance, second flexible end portion 56 is provided as an intermediate portion of flexible tube 10 of insertion unit 6 of the first embodiment of the endoscope. Flexible tube 10 thus is divided into first and second flexible tube sections 50 and 52. In this modification, the freedom of insertion unit 6 is further improved by the provision of the second flexible end portion.

A second embodiment of the endoscope will now be described with reference to FIGS. 15 to 19. FIG. 15 shows the entire endoscope system as the second embodiment of the invention. This endoscope system comprises electronic endoscope 60, image processing unit 62 and compressor 64. Electronic endoscope 60 includes operation unit 4 and insertion unit 6 with flexible end portion 12. To operation unit 4 is connected one end of cable 66 connecting image processing unit 62 and compressor 64 to electronic endoscope 60. Cable 66 has branching point 68, from which cable branch 70 for the light source is connected via plug 72 to image processing unit 62. Image processing unit 62 includes light source unit 74 and camera control unit (CCU) 76. To CCU 76 are connected TV monitor 78, video cassette recorder (VCR) 80 and video printer 82. TV monitor 78 includes image display section 84 and pressure display section 86.

Figure 16:
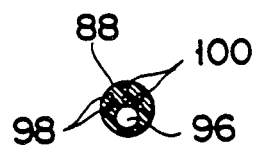
FIG. 16 is a front view showing a connector shown in FIG. 15.

Compressor cable 88 branching from cable 66 is connected via compressor connector 90 to compressor 64. Compressor 64 has two pressure gauges 92 for indicating the pressure of fluid supplied to endoscope 60 and power source switch 94 for on/off operating the power source for compressor 64. Compressor cable 88, as shown in FIG. 16, includes air/water supply ductline 96, compressor control signal lines 98 and pressure signal transmission signal lines 100. Gas or liquid forced out under pressure from compressor 64 is supplied through air/water supply ductline 96 to endoscope 60. Control signals from operation unit 4 of endoscope 60 are transmitted through signal lines 98 to compressor 64. A signal representing the actual detected pressure of compressor 64 is transmitted through signal lines 100 to TV monitor 78. Signal representing the detected pressure of compressor 64 may either be first transmitted to operation unit 4 of endoscope 60 through branching point 68 so that it may be transmitted together with an image signal of the endoscope to CCU 6, or it may be transmitted directly to CCU 76 and then combined with the endoscope image signal in image display section 84.

In the endoscope system as the second embodiment of the invention, the peripheral components such as TV monitor 78, VCR 80 and video printer 82 may be either separate units, which are assembled together, or constituted by a single unit assembled in a casing. Further, TV monitor 78 may display the image signal from endoscope 60 on image display section 84, or may display the pressure of compressor 64 in the form of a bar graph on part of it. The pressure of compressor 64 is simultaneously displayed on pressure gauges 92, and it may be displayed in any desired form on the TV monitor.

Figure 17:
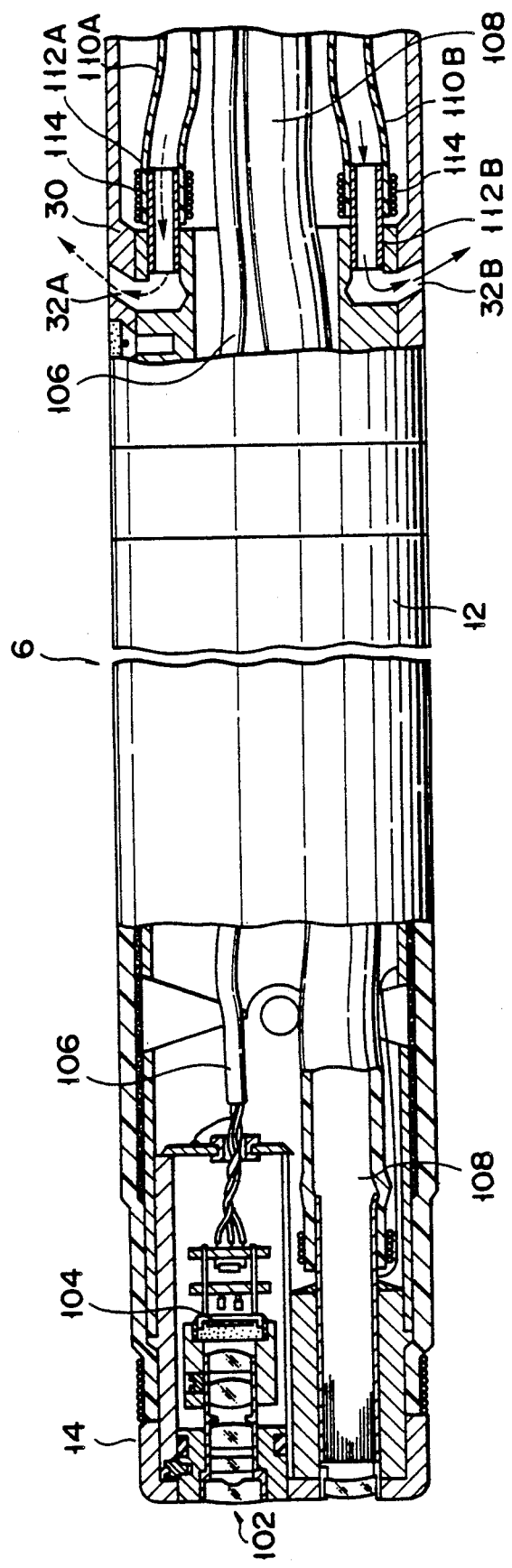
FIG. 17 is a fragmentary sectional view showing an insertion unit of the borescope shown in FIG. 15.
Figure 20:
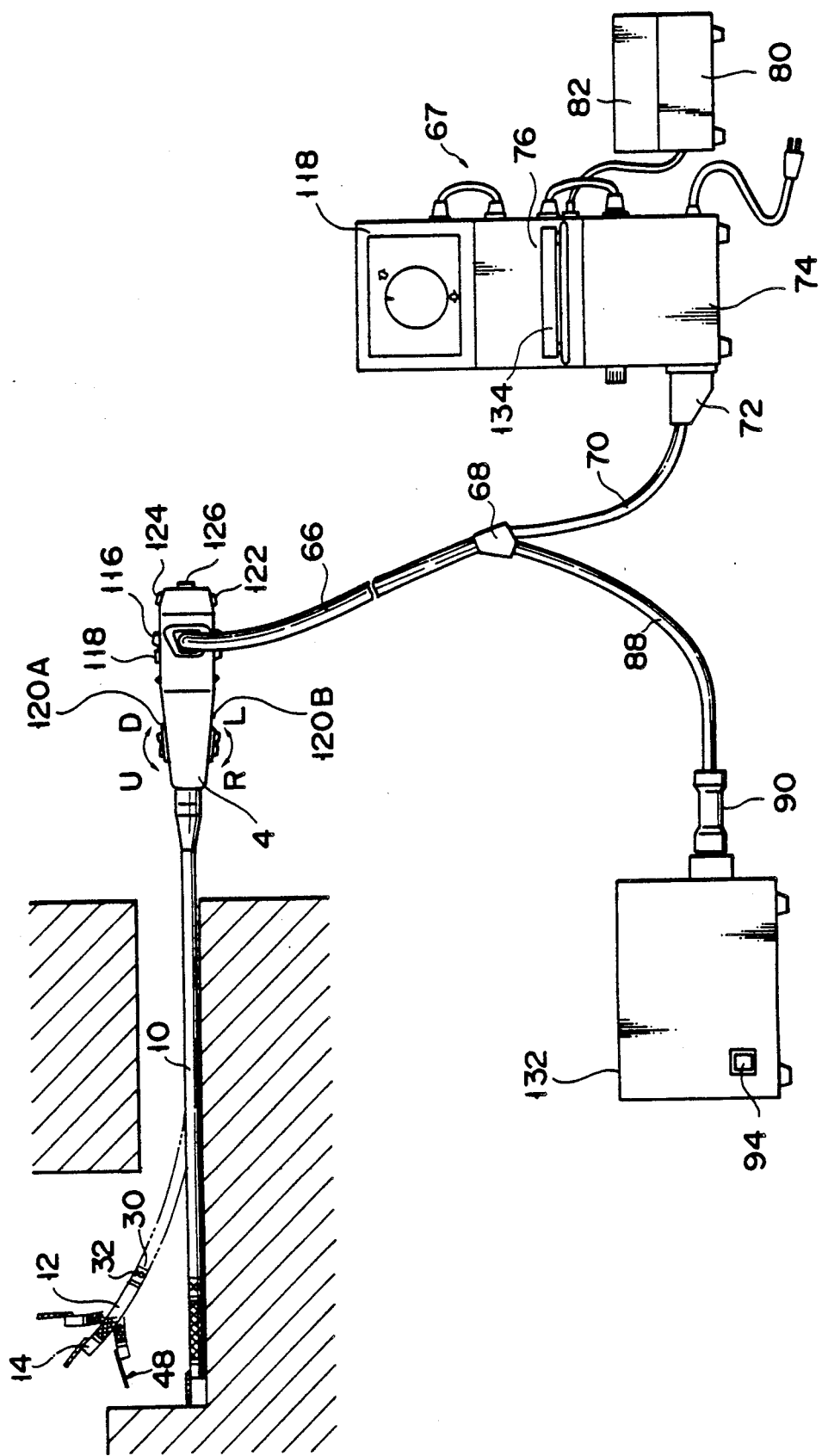
FIG. 20 is a side view showing a first modification of the second embodiment of the borescope.

Now, insertion unit 6 of electronic endoscope 60 will be described with reference to FIG. 17. Insertion unit 6 includes flexible end portion 12 operable for curving by an angle knob provided on operation unit 4, end structure 14 connected to the distal end of flexible end portion 12 and flexible tube portion 10 connected between operation unit 4 and flexible end portion 12. Optical objective lens system 102 is mounted at the distal end of end structure 14, and solid-state image sensor element 104 is disposed behind optical objective lens system 102. Solid-state image sensor element 104 converts a light image incident through optical objective lens system 106 into an electric signal which is transmitted through electric cable 106 to CCU 76. Lightguide 108 extending in parallel to objective lens system 102 in end structure 14 is led through cable 66 and light source side branch cable 70 to be connected to light source unit 74.

Jet port member 30 having first and second fluid jet ports 32A and 32B is provided between flexible end portion 12 and flexible tube portion 10 of insertion unit 6. Flexible tubes 110A and 110B extending through insertion unit 6 are respectively connected by thread windings 114 to connector tubes 112A and 112B provided at jet ports 32A and 32B. They are led through air/water supply ductline 96 in compressor cable 88 and connected to compressor 64. Fluid under pressure thus can be supplied from compressor 64 to jet ports 32A and 32B.

Operation unit 4 of endoscope 60, as shown in FIG. 15, has its central portion provided with UD and RL knobs 116 and 118 for curving flexible end portion 12 in up/down and left/right directions respectively and its front portion provided with pressure control switches 120A and 120B for controlling the output of compressor 64 to control the pressure, under which fluid is jet from jet ports 32A and 32B. Pressure control switches 120A and 120B are provided in the same number as the jet ports of jet port member 30, and each of them is provided on the same side as the corresponding jet port. Operation unit 14 further has its rear portion provided with VCR switch 122 for starting and stopping the video recording by VCR 80, switch 124 for providing still image display on TV monitor 78 for observation and switch 126 for photographing a TV monitor display image as color image. The TV monitor display image can be printed by video printer 82.

Now, the operation of the endoscope system as the second embodiment of the invention will be described with reference to FIG. 15.

When inserting electronic endoscope 60 into a cavity having a narrow inlet, a stepped wall at an intermediate position of the passage and a comparatively large space over the stepped wall as shown in FIG. 15, a portion of the cavity deeper than the stepped wall can not be seen from the outside because it has a dead angle. With a usual endoscope, the insertion unit is gradually inserted into the inlet passage until its distal end strikes the stepped wall, and then flexible end portion 12 is bent upwards by turning UD knob 116 in the U direction, while at the same time insertion unit 6 is pushed forwards, thereby clearing the stepped wall. However, the distal end of the insertion unit is liable to slip down sidewise before it strikes the stepped wall, thus deteriorating the operation efficiency.

With the second embodiment of the endoscope according to the invention, insertion unit 6 is entirely float up by causing compressed air to be jet from appropriately selected one or ones of jet ports 32A and 32B provided at its distal end. Then, while observing the cavity inside, it is advanced with its height adjusted by controlling the pressure of compressed air. In this way, the stepped wall can be cleared. For the operation of floating up insertion unit 6 pressure control switch 120A or 120B provided on operation unit 4 is operated. Further, end structure 14 of insertion unit 6 can be floated up to a desired height with compressed air jet suitably from jet port 32A or 32B through operation of each pressure control switch.

Pressure control switches 120A and 120B are see-saw switches sealed by a rubber cover or the like. By continuously pushing each switch to the reduction side, the output of compressor 64 is reduced continuously, so that the jetting of air is eventually stopped. On the other hand, by continuously pushing the switch to the increase side, the output of compressor 64 eventually, i.e., air jet rate, becomes maximum.

Thus, the operator may adjust the height of floating up of insertion unit 6 by appropriately selecting a pressure control switch and adjusting the air pressure to a suitable value and at the same time bend flexible end portion 12 by operating angle knobs (i.e., UD and RL knobs 116 and 118). In this way, the status of the cavity inside can be observed in detail.

Further, with this endoscope system the insertion unit can be inserted alone into a portion, into which a prior art endoscope insertion unit can not be inserted unless a hard or semi-hard tube like a guide tube is used together. It is thus possible to improve the operability of inspection or the like greatly.

Figure 18:
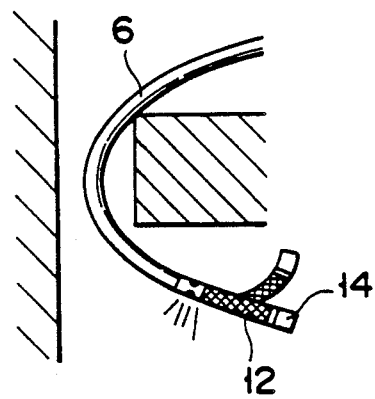
FIGS. 18 and 19 are side views for explaining the use of the second embodiment of the borescope.

For example, for the inspection of a space as shown in FIG. 18, with a prior art endoscope it is the distal end has to be lowered along the vertical wall while curving the flexible end portion as it is inserted and observing portions of the space near the wall. With the endoscope according to the invention, the distal end of insertion unit 6 can be held floated at a suitable distance from the wall by causing the jetting of compressed air as shown in FIG. 18. Thus, it is possible to ready observe the top inner wall surface, which has heretofore been incapable of observation or inspection, that it, it is possible to substantially eliminate the dead angle of a cavity or the like.

Figure 19:
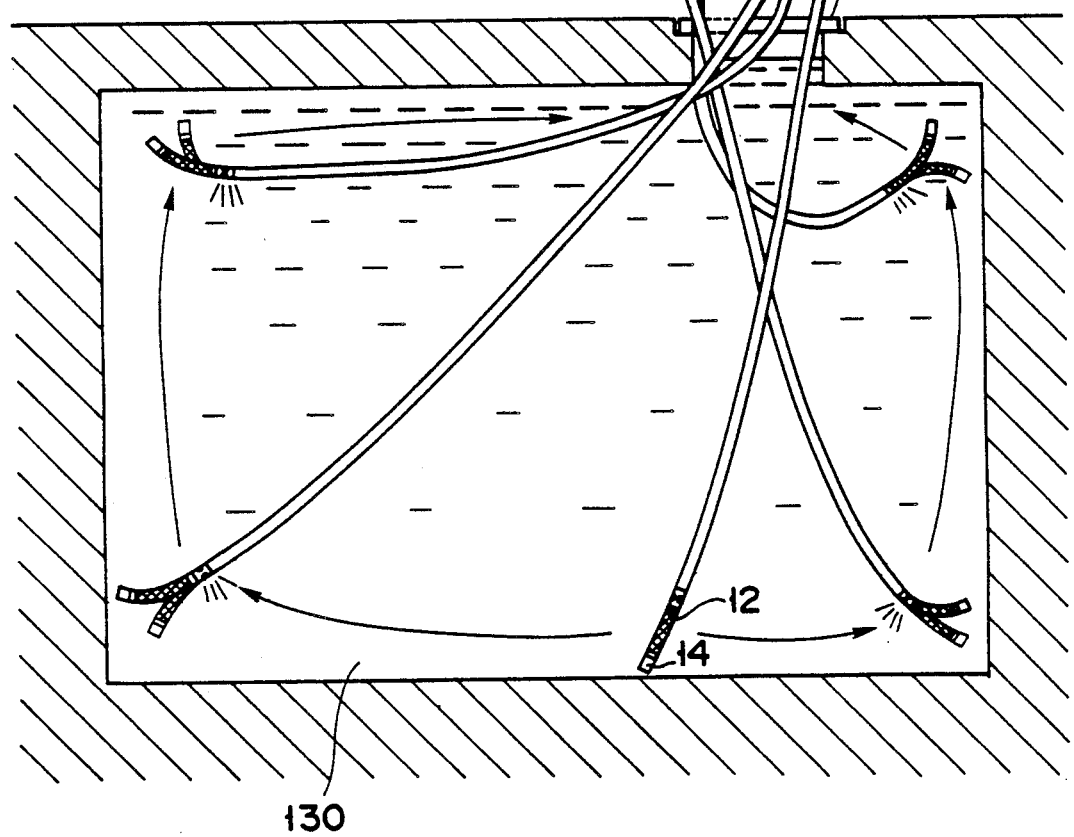

The endoscope of the second embodiment of the endoscope system may be used for the observation of the entire inner wall surfaces of water tank 130 closed by lid 128 as shown in FIG. 19.

More specifically, insertion unit 6 of endoscope 60 is first inserted into water tank 130. However, with insertion unit 6 in a state labeled a, only the bottom surface of water tank 130 can be observed. End structure 14 of insertion unit 6 can be easily moved up to a corner of water tank 130 as shown at b by causing air jet from a jet port. Further, insertion unit 6 may be entirely floated up to a state labeled c for observation of the side and top inner wall surfaces of water tank 130. Further, insertion unit 6 may be moved to states labeled d and e.

While in the above case insertion unit 6 of endoscope 60 is moved in water contained in water tank 130, the same movement may also be obtained when water tank 130 is empty. Further, the endoscope according to the invention may be used not only in water but also in other transparent liquids, for which it can be used for observation.

Although the pressure of the supplied fluid can be controlled through output control with compressor 64 and pressure control switches 120A and 120B, it is also possible to provide such control means as a reducing valve (not shown) in operation unit 4 to maintain constant the output of compressor 64 and pressure of the supplied fluid. Alternatively, the flow rate of the supplied fluid from compressor 64 may be regulated by a proportional control valve (not shown).

Electronic endoscope 60 of the endoscope system may use an image sensor element of a plane sequential system or color mosaic system and a camera controller of the same system. Further, it may use a fiberscope. In this case, an external attachment camera may be mounted on an objective lens section of the fiberscope.

A first modification of the second embodiment of the endoscope according to the invention will now be described with reference to FIGS. 20 to 23.

Figure 21:
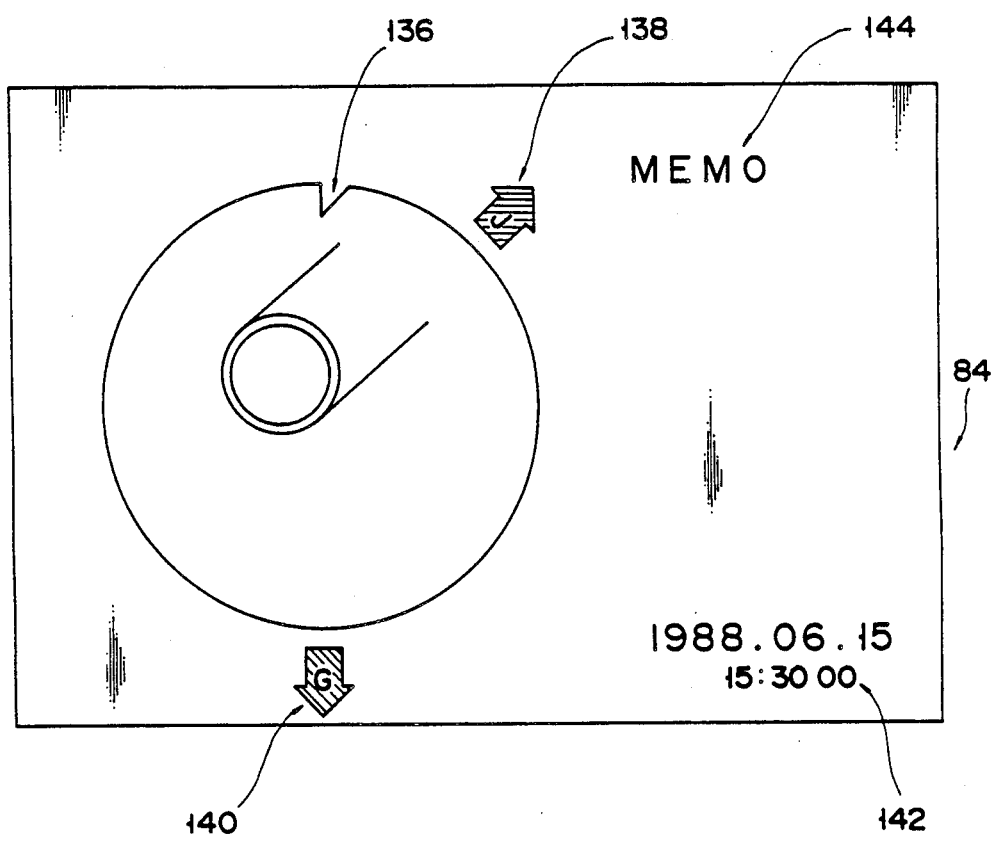
FIG. 21 is a front view showing the screen of a TV monitor shown in FIG. 20.

In this instance, insertion unit 6 is provided with four jet ports 32. Operation unit 4 has control switch 120A for controlling fluid jet from upper and lower jet ports 32 and control switch 120B for controlling fluid jet from left and right jet ports 32. In this modification, pressurized source unit 132 for supplying pressure to each jet port is provided in lieu of compressor 64. Image processing unit 62 has keyboard 134, and it can co-operate with the CPU of CCU 76 to display upward direction mark 136, advancement direction mark 138, gravidy direction mark 140, date 142 and comments 144 on the screen of TV monitor 78 as shown in FIG. 21.

Figure 22:
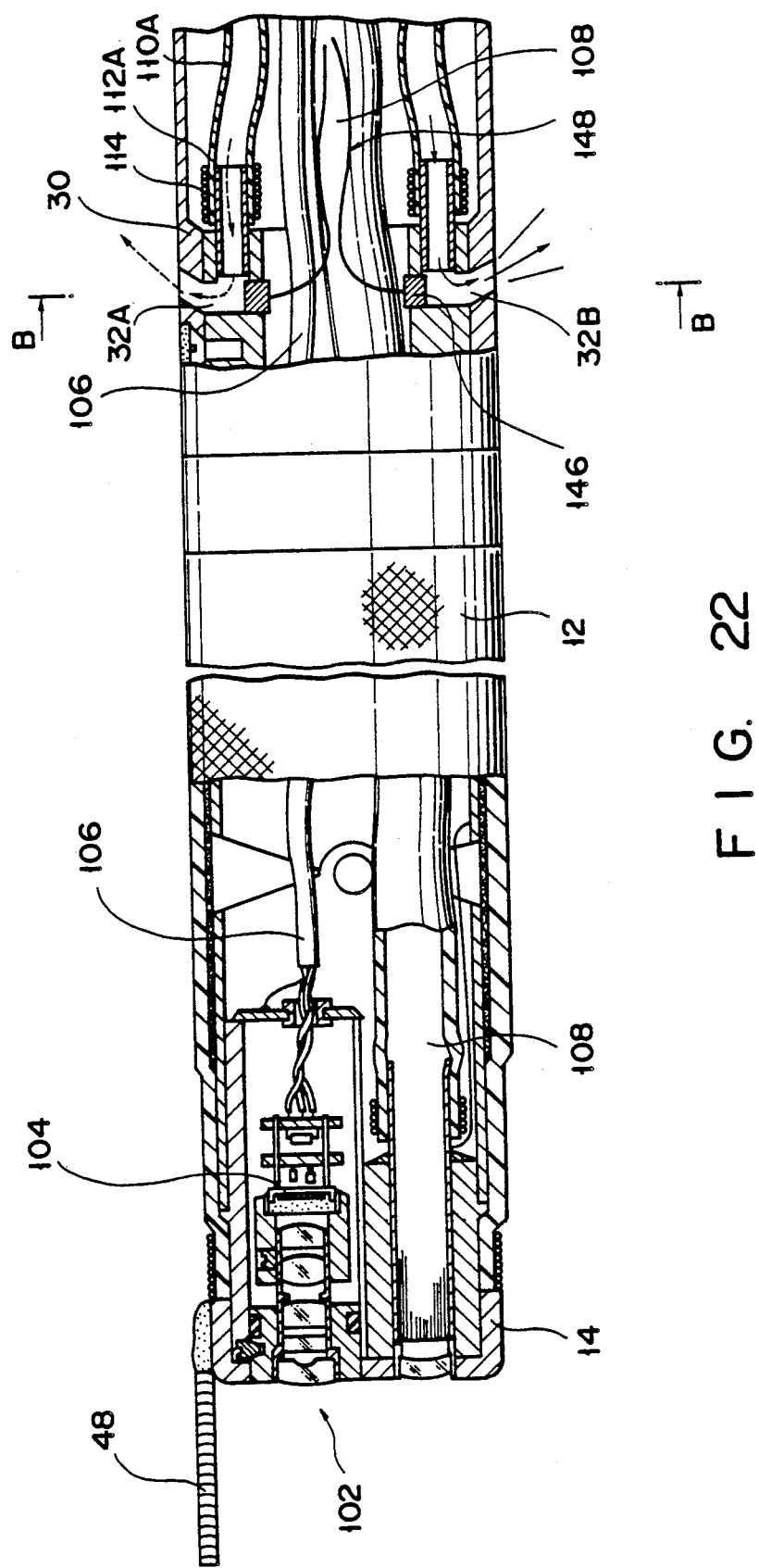
FIG. 22 is a fragmentary sectional view showing an insertion section shown in FIG. 20.
Figure 23:
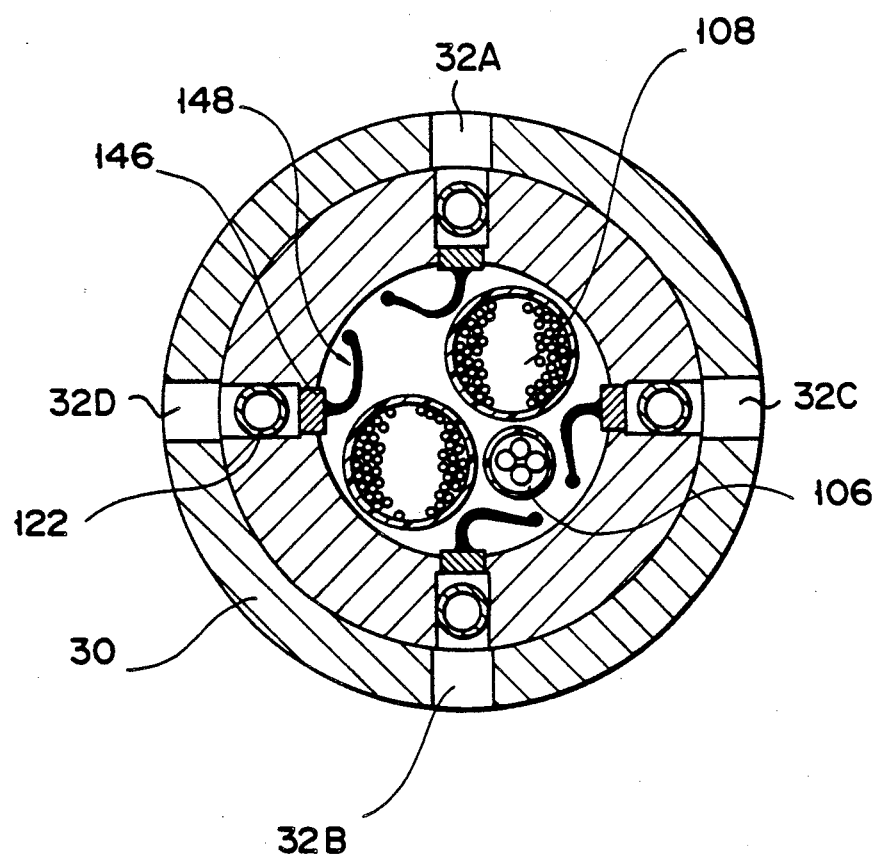
FIG. 23 is a sectional view taken along line B—B in FIG. 22.

In this modification, as shown in FIGS. 22 and 23, pressure sensors 146 are each provided at each jet port 32 of jet port member 30, and signal cables 148 are connected to pressure sensors 146. Pressure signals from pressure sensors 146 are transmitted through signal cables 148 to CCU 76 to be displayed on TV monitor 78, and the pressure signals are also fed back to pressurized source unit 132, so that the jet pressure can be controlled to maintain the predetermined pressure rate. In this modification, flow rate sensors can be used instead of pressure sensors 146.

Figure 24:
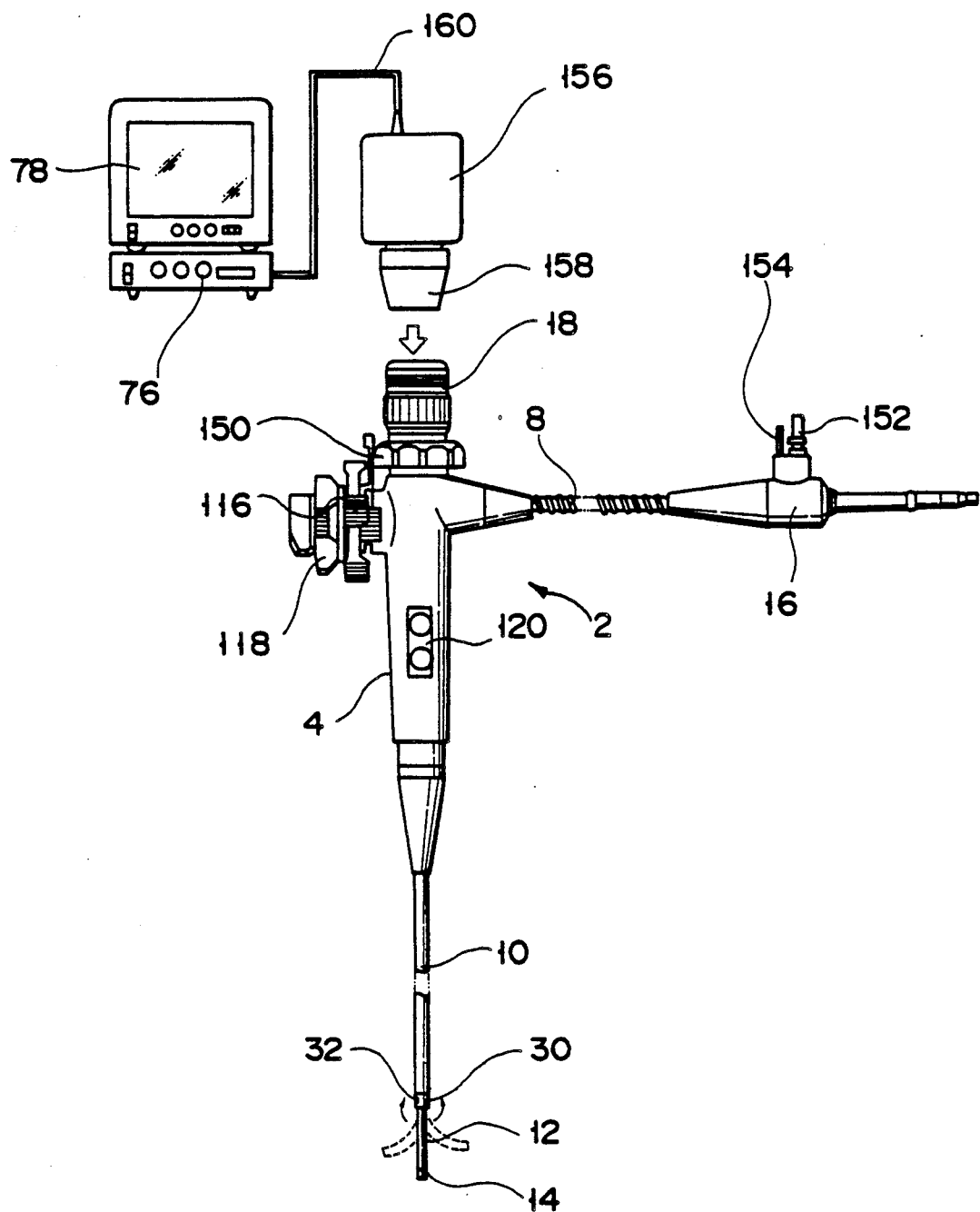
FIG. 24 is a side view showing a second modification of the second embodiment of the borescope.

FIG. 24 shows a second modification. In this instance, endoscope 2 of the system is a fiberscope. Operation unit 4 of this endoscope UD and RL knobs 116 and 118 for control in up/down and right/left directions respectively. Further, it has focus control knob 150 provided between operation unit 4 and objective lens section 18. Universal cord 8 leading from operation unit 4 is connected to a connector 16, which has air supply tube connector 152 and signal line connector 154. On objective lens section 18, adopter 158 of TV camera 156 is mounted, and TV camera 156 is connected through TV signal cable 160 to CCU 76 and TV monitor 78.

A third embodiment of the invention will now be described with reference to FIGS. 25 to 28. FIG. 25 shows endoscope 2 and light source unit 74. Endoscope 2 includes operation unit 4. Elongate flexible insertion unit 6 and universal cord 8 are connected to operation unit 4. Universal cord 8 is connected to connector 72 detachably coupled to light source unit 74.

End structure 14 of insertion unit 6, as shown in FIG. 26, has observation window 164, two illumination windows 168 and clamp channel opening 170. Observation window 164 is optically coupled through an image guide to objective lens section 18 of operation unit 4. Illumination windows 168 are coupled to light-guides (not shown) which are led through insertion unit 6, operation unit 4 and universal cord 8 to connector 72 and optically coupled through connector 72 to a light source in light source unit 74.

Figure 27:
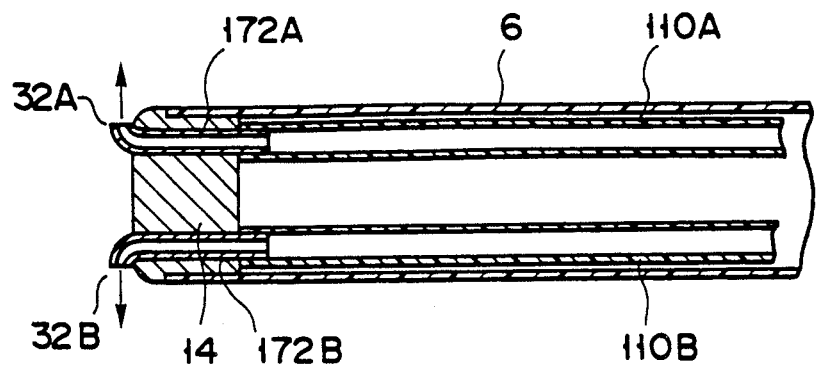
FIG. 27 is a schematic sectional view showing an insertion unit shown in FIG. 25.

End structure 14 of insertion unit 6 has four jet ports 32A to 32D formed along its front face edge, as shown in FIG. 26. As shown in FIG. 27, jet ports 32A to 32D are formed by respective nozzle tubes 172 penetrating end structure 14. Ends of nozzle tubes 172 projecting from end structure 14 bent outwardly, i.e., away from one another, thus forming jet ports 32A to 32D. To nozzle tubes 172 are connected respective flexible tubes 110 for supplying high pressure fluid to corresponding jet ports 32A to 32D. Flexible tubes 110 are connected through insertion unit 6, operation unit 4 and universal cord 8 to connector 72 and connected through connector 72 to high pressure fluid source unit 132 provided in light source unit 74. High pressure fluid source unit 132 consists of a common pump or individual pumps. Where a common pump is utilized, the supply pressure is suitably controlled through individual variable aperture valves.

As is shown, this embodiment of endoscope has a high pressure fluid source, which supplies high pressure fluid, e.g, air, individually to jet ports 32A to 32D through respective flexible tubes 110. The pressure and rate of flow of high pressure fluid jet from jet ports 32A to 32D can be controlled individually through individual control of the pump outputs or variable aperture valves. Each pump is suitably provided with a reservoir tank for alleviating the discharge pressure pulsation. The control of the pressure and rate of supply is effected by control means which will be described hereinunder. That is, operation unit 4 has jet port selection switch 174 and flow rate control switch 176. Signals from these switches are transmitted through signal lines (not shown) led through universal cord 8 to a control circuit provided in light source unit 74. The control circuit can control the high pressure fluid source according to instructions given to it for individually controlling the pressure and flow rate of high pressure fluid supplied to jet ports 32A to 32D.

Now, the use of the third embodiment of endoscope 2 will be described. Insertion unit 6 is inserted into, for instance, a piping while observing the field of the endoscope. If high pressure air is caused to jet slightly from each of jet ports 32A to 32D at this time, as end structure 14 of insertion unit 6 approaches an inner wall of the piping, a strong reaction force produced by high pressure fluid jet from a jet port near the wall acts on the end structure to reduce the frictional force produced thereat. Thus, the insertion of insertion unit 6 is facilitated.

Figure 28:
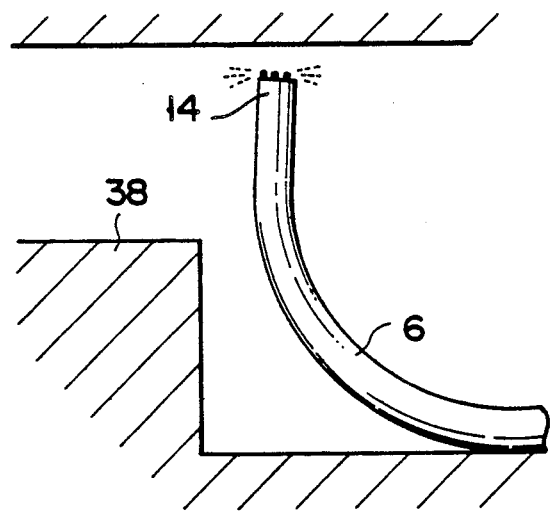
FIG. 28 is a side view for explaining the use of the third embodiment of the borescope.

Then, by selecting a desired jet port by operating jet port selection switch 174 and causing a jet of high pressure fluid through the selected jet port, a reaction force of the jet fluid can cause curving of flexible insertion unit 6 in the opposite direction to the jetting direction. Further, by increasing the rate of flow by operating flow rate control switch 176, end structure 14 can be raised up to a considerable height level as shown in FIG. 28. Insertion unit 6 thus can be inserted by clearing stepped wall 38 as shown in FIG. 28, if any.

By causing fluid to be jet from left and right jet ports 32C and 32D as well at controlled jetting rates, insertion unit 6 may not only be curved upwards but also be tilted to the left or right. Air purging from the cavity is suitably done in case when jetting high pressure fluid continuously for long time, although it is unnecessary in case of tentatively jetting high pressure fluid.

Figure 29:
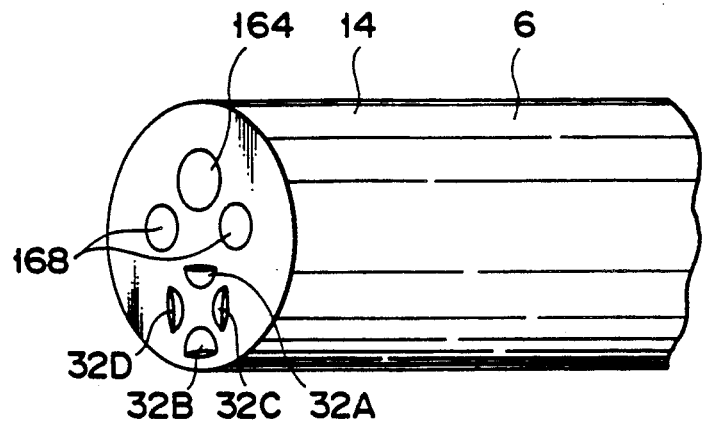
FIG. 29 is a perspective view showing a first modification of the third embodiment of the borescope.

FIG. 29 shows a first modification of the third embodiment of the invention. In this instance, upper, lower, left and right jet ports 32A to 32D are formed on the front surface of end structure 14 of insertion unit 6 not along the edges of the front surface but in a confined portion thereof. For the rest, this modification is the same as the third embodiment.

Figure 30:
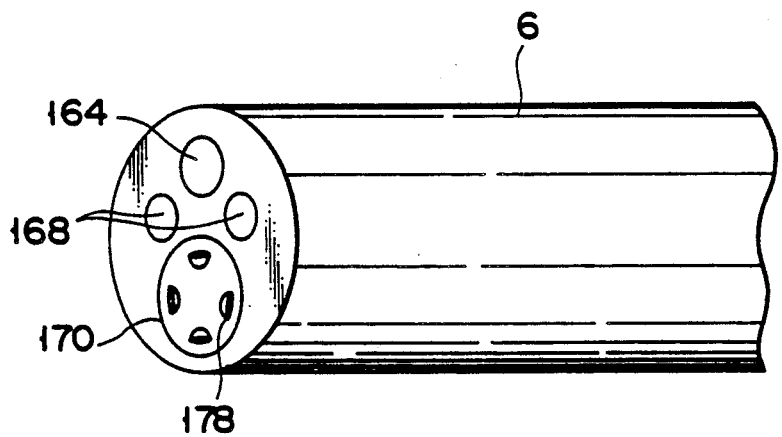
FIG. 30 is a perspective view showing a second modification of the insertion unit.
Figure 31:
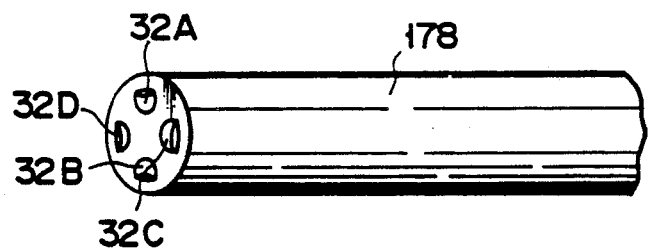
FIG. 31 is a perspective view showing a tube in the second modification.

FIGS. 30 and 31 show a second modification. This modification includes flexible insertion member 178 as shown in FIG. 31, which can be inserted through clamp channel 170 of typical endoscope 2 as shown in FIG. 30. The front end surface of insertion member 178 has four, i.e., upper, lower, left and right, jet ports 32A to 32B. By inserting insertion member 178 through clamp channel 170 of endoscope 2 such that the former projects from the latter, this modification can be used in the same way as the first modification.

FIG. 32 shows a third modification. In this instance, the outer periphery of end structure 14 of insertion unit 6 is provided with upper, lower, left and right jet ports 32A to 32D. Jet ports 32A and 32D are directed outwardly along normals to the outer periphery of end structure 14.

FIGS. 33 to 36 show a fourth modification. In this instance, a plurality of jet ports 32 and 33 are provided at two positions, i.e., position 6A adjacent to the distal end and position 6B rearwardly therefrom of flexible elongate insertion unit 6. As in the preceding third modification, jet ports 32 and 33 are directed normally with respect to the outer periphery of insertion unit 6. They are circumferentially uniformly spaced apart. They are connected to respective high pressure fluid sources. The pressure and rate of flow of high pressure fluid supplied from the high pressure fluid sources are controlled by control means.

Figure 35:
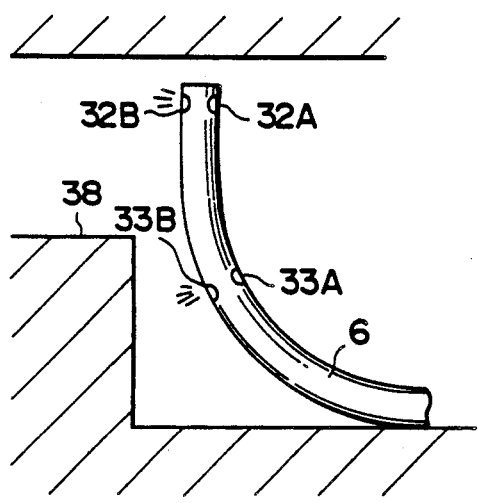
Figure 36:
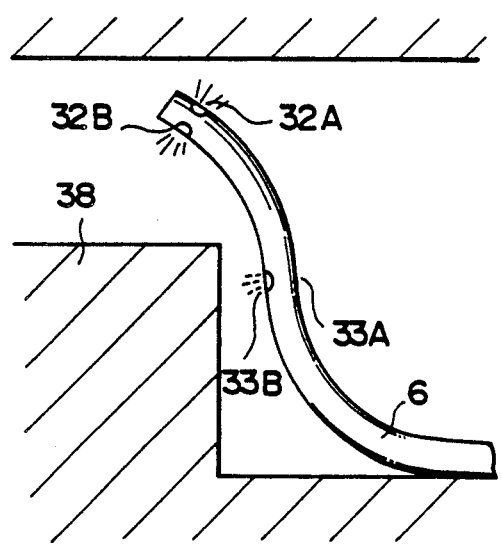

In the use of this fourth modification of endoscope 2, by causing high pressure fluid to be jet from only the downwardly directed one of forward jet ports 32, a forward end portion of insertion unit 6 can be curved to a more or less upright state as shown at (a) in FIG. 34. Further, by concurrently causing high pressure fluid to be jet from the down-wardly directed one of rearward jet ports 33 as well, the end of insertion unit 6 may be raised to a greater height as shown at (b) in FIG. 34. By utilizing the function described above, insertion unit 6 may be inserted deeply into a cavity having stepped wall 38 at an intermediate position as shown in FIG. 35. More specifically, insertion unit 6 is inserted with its distal end raised to a height beyond stepped wall 38. Then by causing a jet from initially upper one 32A of forward jet ports 32, an end portion of insertion unit 6 is curved to a shape of figure S with its distal end directed toward a deeper space ahead of stepped wall 38. At this time, the rate of jetting from forward jet port 32 is suitably set to be double the rate of jetting from rearward jet port 33. Insertion unit 6 may be advanced in this form, whereby it can be inserted into a deeper space than stepped wall 38. If stepped wall 38 has a small height, high pressure fluid may not be jet from rearward jet port 33.

A fourth embodiment of the invention will be described with reference to FIGS. 37 to 41. FIG. 39 shows endoscope 2 including operation unit 4. Flexible insertion unit 6 capable of being curved and universal cord 8 are connected to operation unit 4. Universal cord 8 is connected to light source connector 72, which is connected to light source unit 74, and also to compressor connector 90, which is connected to pressurised soruce unit 132 for controlling the curving of insertion unit 6.

Insertion unit 6 has four, i.e., upper, lower, left and right, jet ports 32A to 32D formed adjacent to its distal end and circumferentially spaced apart at an interval of 90 degrees. UD and LR knobs 116 and 118 are provided rotatably on operation unit 4. The rate of jet of compressed air from the individual jet ports can be controlled by appropriately turning knobs 116 and 118.

Pressurised source unit 132, as shown in FIG. 39, includes compressor 64. Compressed air discharged from compressor 64 is supplied through reservoir tank 180 to first and second regulators 182 and 184. Regulators 182 and 184, as shown in FIG. 37, each have first port 186, to which compressor 64 is connected, and second and third ports 192, which can be communicated with first port 186 by valve 188 as shown in FIG. 38.

Second and third ports 190 and 192 of first regulator 182 are connected to upper and lower jet ports 32A and 32B, respectively. Second and third ports 190 and 192 of second regulator 184 are connected to right and left jet ports 32C and 32D, respectively. Valve 188 in first regulator 182 is driven to the right or left as shown by arrows in FIG. 38 according to a signal from first controller 194, whereby either second or third port 190 or 192 is communicated with first port 186 to control the rate of flow of compressed air from first port 186 to second or third port 190 or 192.

Valve 188 in second regulator 184, like that in first regulator 182, is driven to the right or left according to a signal from second controller 196 to control the rate of flow of compressed air from first port 186 to second or third port 190 or 192.

First controller 194 receives a signal from first encoder 198. First encoder 198 is operable according to the direction and angle of rotation of UD knob 116 to provide a signal to first controller 194. Second controller 96 receives a signal from second encoder 200. Second encoder 200 is operable according to the direction and angle of rotation of RL knob 118 to provide a signal to second controller 196.

Insertion unit 6, as shown in FIG. 40, has channel 170. Ultrasonic probe 202 as shown in FIG. 42 or clamp 204 as shown in FIG. 43 may be introduced into a subject of observation, e.g., a body cavity, through channel 170. Ultrasonic probe 202 and clamp 204 both have seal member 206 having an outer diameter equal to or slightly smaller than the diameter of channel 170. When compressed air is supplied as compressed fluid into channel 170 with ultrasonic probe 202 inserted in channel 170, the pressure of compressed air is exerted to seal member 206 and provides a propulsion force to feed ultrasonic prove 202. When the end of ultrasonic probe 202 projects from channel 170 as shown in FIG. 41, compressed air no longer acts as propulsion force on seal member 206, so that probe 202 is stopped at that position. That is, probe 202 will never violently strike the subject of observation. As shown in FIGS. 40 and 41, the distal end surface of insertion unit 6 is provided with observation window 164 and a pair of illumination windows 168. Seal member 206 may have various sectional profiles as shown in FIGS. 44 to 47.

Now, an operation of curving insertion unit 6 of the endoscope having the above construction will be described. To cause downward curving of insertion unit 6, UD knob 116 is turned to the left, for instance. The direction and angle of the turning are detected by first encoder 198, which thus supplies a corresponding signal to first controller 194. As a result, valve 188 in first regulator 182 is moved to the right in FIG. 38, thus communicating first port 186 with second port 190. Compressed air from compressor 64 thus is led through second port 190 to be jet from upper jet port 32A of insertion unit 6. Thus, with the reaction force insertion unit 6 is curved downwards. The angle of downward curving of insertion unit 6 can be varied according to the rate of jetting of compressed air from upper jet port 32A. The rate of jetting can be varied according to the rotational angle of UD knob 116, so that the angle of downward curving of insertion unit 6 can be varied freely in a predetermined range.

To cause upward curving of insertion unit 6, UD knob 116 is turned to the right. As a result, valve 188 in first regulator 182 is moved to the left in FIG. 38, thus communicating first port 186 with third port 192. Compressed air thus is jet from lower jet port 32B of insertion unit 6, so that insertion unit 6 is curved upwards. Again in this case, the rate of jetting of compressed air from lower jet port 32B is controlled according to the rotational angle of UD knob 116, thus permitting control of the angle of upward curving of insertion unit 6.

Now, an operation of curving insertion unit 6 to the left and right will be described. To cause leftward curving of insertion unit 6, RL knob 118 is turned to the left. As a result, a signal corresponding to the direction and angle of rotation is supplied form second encoder 200 to second controller 196. Valve 188 in second regulator 184 thus is moved to the right in FIG. 38 to communicate first port 186 of first regulator 184 with second port 190. As a result, compressed air from compressor 164 is led through second port 190 to be jet from right jet port 32C, so that insertion unit 6 is curved leftwards by the reaction force. In this case, the angle of curving of insertion unit 6 can be varied according to the rate of jetting of compressed air from insertion unit 6. The rate of jetting can be controlled according to the rotational angle of RL knob 118.

To cause rightward curving of insertion unit 6, RL knob 118 is turned to the right. In this case, valve 188 in second regulator 184 is moved to the left in FIG. 38 to communicate first port 186 with third port 192. Compressed air thus is jet from left jet port 32D, so that insertion unit 6 is curved left-wards by the reaction force. Again in this case, variation of the rightward rotational angle of RL knob 118 varies the rate of jetting of compressed air from left jet port 32D to vary the angle of right-ward curving of insertion unit 6.

Figure 49:
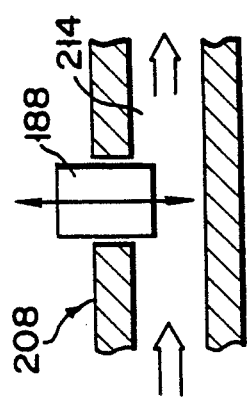
FIG. 49 is a schematic view showing a valve in a first modification.
Figure 48:
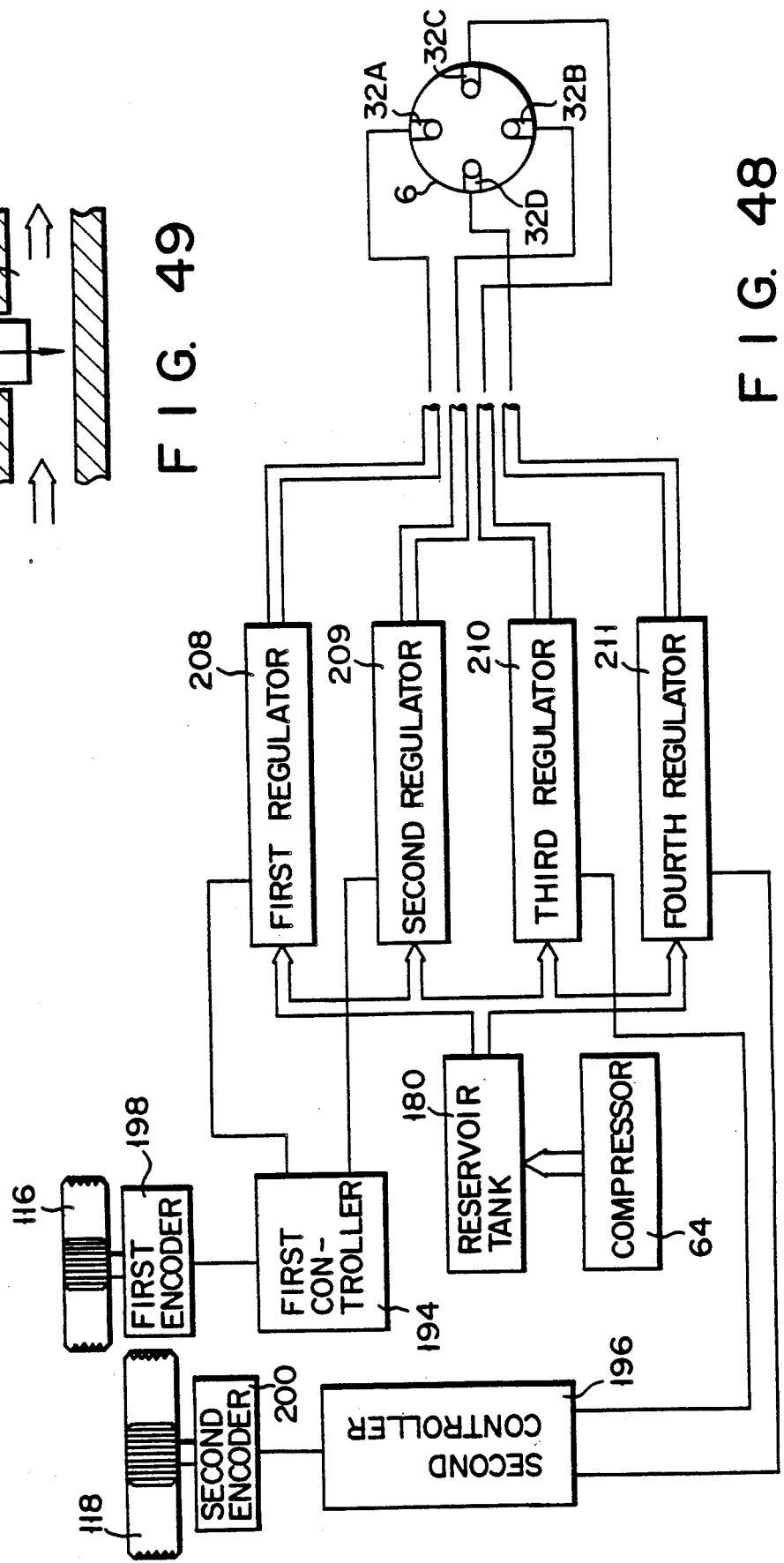
FIG. 48 is a block diagram showing a first modification of the fourth embodiment of the borescope.

FIGS. 48 and 49 show a first modification of the fourth embodiment. In this instance, four, i.e., first to fourth, 2-port regulators 208 to 211 are used in lieu of two 3-port regulators 182 and 184. In each two-port regulator, as shown in FIG. 48, its passage 214 has one end communicated with compressor 64 and the other end communicated with an associated one of jet ports 32A to 32D. Valve 188 is movably provided in an intermediate portion of passage 214. As in the fourth embodiment, valve 188 can be driven by first or second controller 194 or 196 to control the aperture of passage 214.

First controller 194 selectively provides a drive signal to either first or second regulator 208 or 209, and second controller 196 selectively provides a drive signal to either third or fourth regulator 210 or 211.

Thus, in this modification, like the previous fourth embodiment, the angle and direction of curving of insertion unit 6 can be controlled.

Figure 50:
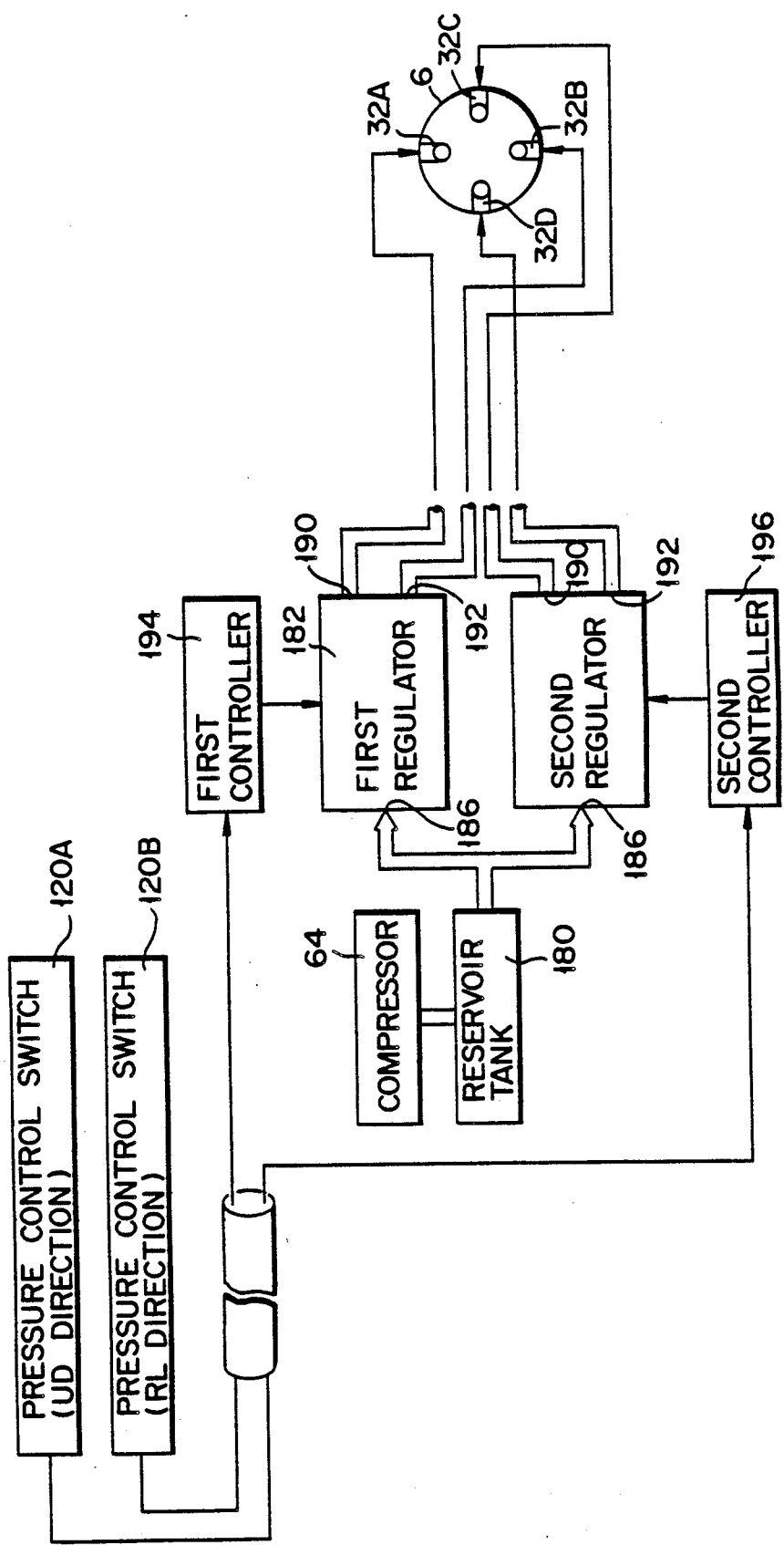
FIG. 50 is a block diagram showing a second modification of the fourth embodiment of the borescope.

FIG. 50 shows a second modification. In this instance, UD and RL pressure control switches 120A and 120B are used in lieu of first and second encoders 198 and 200 in the fourth embodiment.

Figure 51:
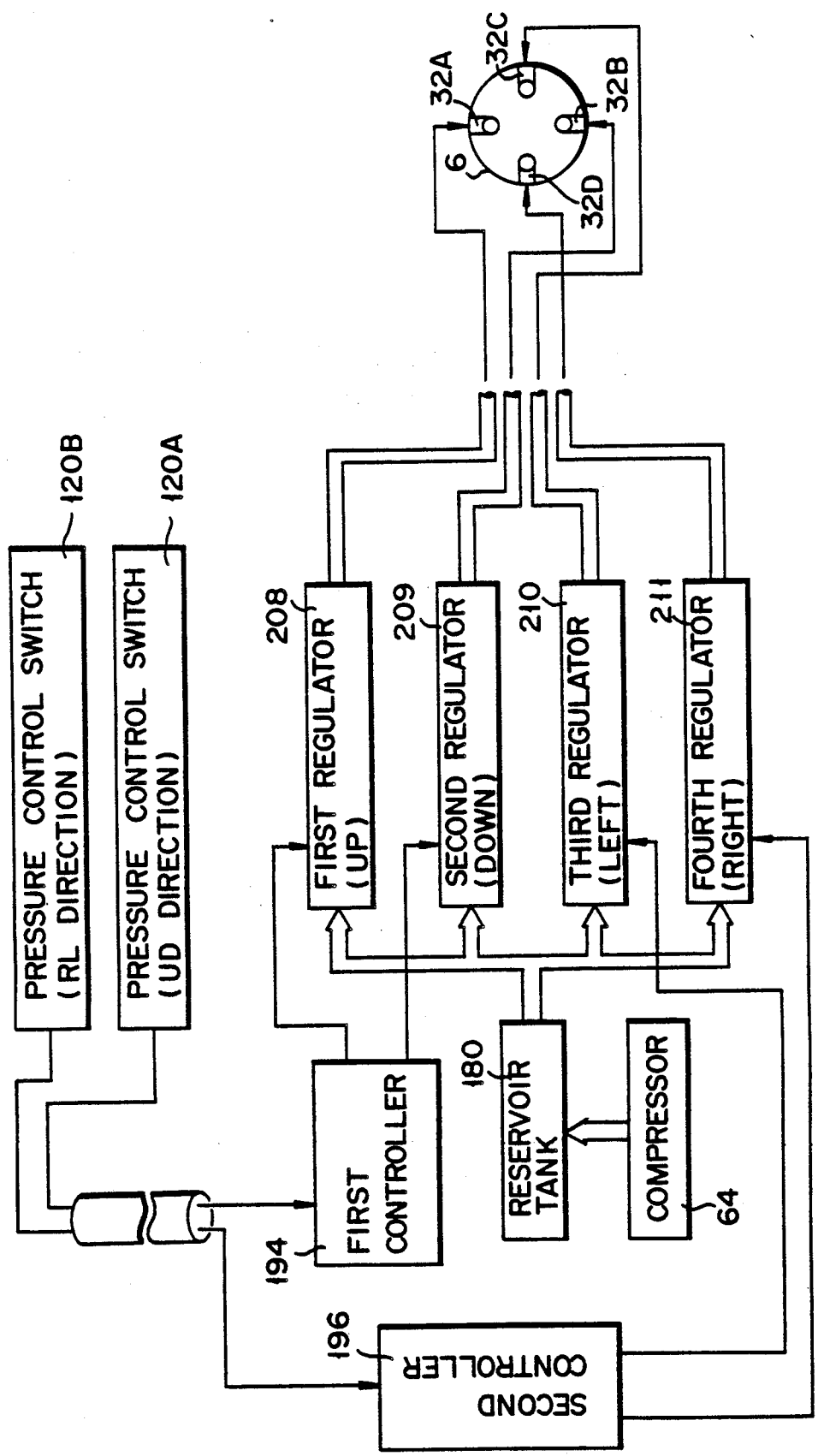
FIG. 51 is a block diagram showing a third modification of the fourth embodiment of the borescope.

FIG. 51 shows a third modification. In this instance, UD and RL pressure control switches 120A and 120B are used in lieu of first and second encoders 198 and 200 in the first modification.

With the second and third modifications, the same effects as the fourth embodiment can be obtained.

The control system of the fourth embodiment can be used to that of the first modification of the second embodiment shown in FIGS. 20 to 23.

FIGS. 52 to 54 show a fifth embodiment of the invention. FIG. 52 shows endoscope 2 with insertion unit 6. Insertion unit 6 has flexible tube portion 10, bending portion 12 and end structure 14. Flexible tube portion 10 can be bent by applying a external force. Bending portion 12 consists of a train of articulation elements coupled to one another, and it can be forcively curved by pulling wires (not shown) inserted through it with a wire-pulling mechanism provided in operation unit. Front end surface 14A of end structure, as shown in FIG. 53, has observation window 164 of an optical observation system and a pair of illumination windows 168 of an optical illumination system. The optical illumination system uses a lamp or a lamp guide, and the field of observation can be illuminated from illumination window 168. The optical observation system uses a solid-state image sensor element, and the field that can be seen through observation window 164 can be observed through an objective lens section provided in the operation unit or observed as image display on a TV monitor.

Jet port member 30 is provided between flexible tube portion 10 and flexible end portion 12 of insertion unit 6. The outer periphery of jet port member has a plurality of, e.g., four, i.e., upper, lower, left and right, jet ports 32A to 32D. Jet ports 32A to 32D are provided rearwardly obliquely with respect to the axis direction of insertion unit 6. Inner pressure sensors 146 are each provided near each of jet ports 32A to 32D. Pressure sensors 146 can detect the pressure of high pressure fluid jet from respective jet ports 32A to 32D. Pressure signals from pressure sensors 146 are transmitted through signal lines 148 led through insertion unit 6 to control means.

Different fluid supply channels or flexible tubes 110 are connected independently to jet ports 32A to 32D. Individual flexible tubes 110 are led through insertion unit 6 to be connected to fluid sources provided outside endoscope and can supply high pressure fluid independently to jet ports 32A to 32D. Control means for controlling fluid supplied to jet ports 32A to 32D utilizes on-off valves or throttle valves and can be operated by operation knobs provided o operation unit of endoscope 2. The control unit of the fourth embodiment can be used to the fluid control means of this embodiment. As shown in FIG. 54, in observation field 218 defined by a field mask, upward direction mark 220 is provided. Around observation field 218, triangular marks a to d are provided at upper, lower, left and right positions as means for indicating the propelling direction. Triangular marks a to d may be selectively turned on by light-emitting diodes or like drive means. Further, in the fifth embodiment auxiliary circle marks 222 are provided between adjacent ones of marks a to d. These marks 222 may also be selectively turned on by light-emitting diodes or like drive means.

Now, the use of this embodiment of endoscope 2 will be described. By inserting insertion unit 6 of endoscope 2 into a pipeline or the like and supplying high pressure fluid to lower jet port 32A through corresponding flexible tube 110 to be jet from jet port 32A, a thrust is produced by the jetting of fluid so that insertion unit 6 is floated upwards.

Then, by causing fluid to be jet from either one of other jet ports 32B to 32D, insertion unit 6 can be moved in a direction opposite to the direction of the jet. When fluid is jet from two adjacent ones of jet ports 32A to 32D at a time, a resultant of the individual thrusts may be acted on insertion unit 6.

In actual circumstances of use, the operator observes observation field 218 of endoscope 2 by looking through objective lens section or watching the TV monitor screen. Therefore, the direction of thrust produced by the jet of fluid can not be accurately grasped from the sole image of observation field 218. Particularly, when elongate insertion unit 6 is being inserted deeply while bending it, it is twisted, so that it is difficult to accurately grasp the direction of thrust produced by the jet.

In this embodiment of the endoscope, however, pressure sensors 146 mounted at jet ports 32A to 32D detect the pressure of fluid jet from these jet ports. Detected pressure signals from pressure sensors 146 are transmitted through signal cable 148 to an operational processing circuit in a controller (not shown) for calculation of the direction of the thrust. For example, when fluid is being jet from jet port 32A alone, detected pressure signal is obtained only from pressure sensor 146 at jet port 32A. In this case, only mark a around observation field 218 shown in FIG. 54 is turned on to indicate the direction of the thrust. When fluid is jet also from jet port 32D adjacent to jet port 32A, mark d is also turned on, indicating that the thrust is in direction F intermediate between "on" marks a and d. In this case, it is possible to turn on auxiliary mark 222 between marks a and d as the vector sum of thrust directions instead of turning on marks a and d.

In this fifth embodiment the direction of the thrust produced by the jet can be grasped while observing observation field 218, so that it is possible to guide insertion unit 6 readily and accurately. That is, it is possible to improve the operability of the endoscope.

FIG. 55 shows a first modification of the second embodiment of the invention. In this modification, a greater number of marks 222 are provided around observation field 218. Meanwhile, individual pressure sensors 146 are coupled together by a comparator circuit for comparison of their signal levels. Thus, the thrust direction is detected as a vector sum of the individual thrust directions, and only one mark 222 is turned on to indicate the thrust direction.

Since a greater number of marks 222 are provided, the direction can be indicated more accurately.

Further, in this fifth embodiment on/off type gravitational direction indication marks 224 are provided around observation field 218 to indicate a gravitational direction detected by graviational direction sensor means. Thus, the gravitational direction can be indicated at the same time. Gravitational direction indication marks 224 may have a different color from that of thrust direction indication marks 222 so that they can be readily discriminated.

Figure 56:
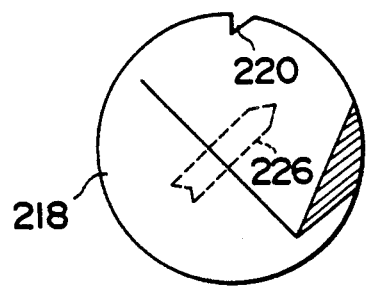
FIGS. 56 and 57 are respectively a front view and a side view schematically showing a second modification of the observation field section.
Figure 57:
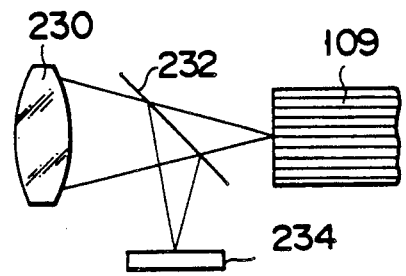

FIGS. 56 and 57 show a second modification. In this instance, thrust direction indication mark 226 is shown in observation field 218, as shown in FIG. 56. FIG. 57 shows means for showing the thrust direction in observation field 218. As is shown, half-mirror 223 is provided between image guide 109 and objective lens 230 in the objective lens section of endoscope 2, and mark 226 from liquid crystal display unit 234, for instance, is reflected by half-mirror 232 to be taken along the optical axis.

In this modification, the thrust direction is shown in superim position on the observation image of observation field 218. Thus, observation can be made without need of deviation of the point of view, so that the observation image can be readily observed.

Figure 58:
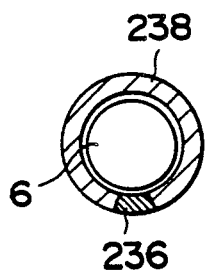
FIGS. 58 and 59 are respectively transversal and longitudinal sectional views schematically showing graditational direction detection means.
Figure 59:
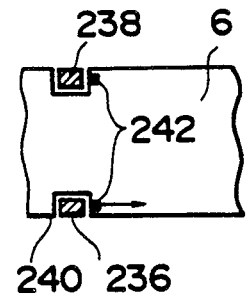

FIGS. 58 and 59 show means for detecting the gravitational direction of insertion unit 6. The gravitational direction detected by this detection means can be displayed in or near observation field 218. More specifically, in the display means of the first modification gravitational direction marks 224 are selectively turned on, and in the display means of the second modification this gravitational direction can be taken along the axis of the objective lens through half-mirror 232 by making use of liquid crystal display unit 234. FIGS. 58 and 59 show means for detecting the gravitational direction. As is shown, rotary ring 238 having weight 236 is provided on a intermediate portion of insertion unit 6, and sensors 242 for detecting weight 236 are provided along guide groove 240, along which rotary ring 238 can be rotated. Thus, the gravitational direction with respect to observation field 218 can be detected by detecting the position of weight 236.

Figure 60:
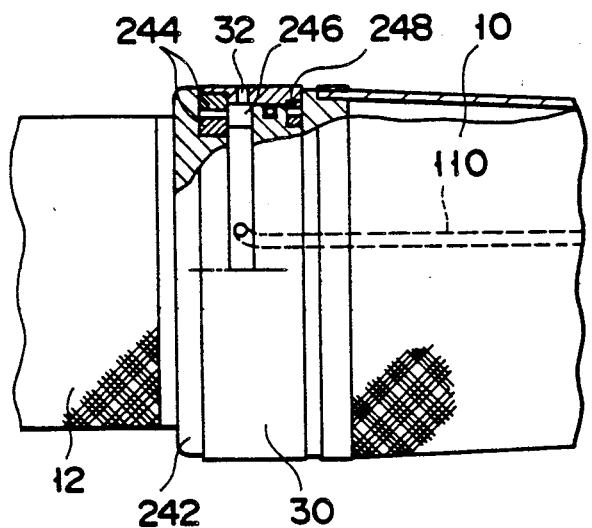
FIG. 60 is a fragmentary sectional view schematically showing a modification of the insertion section.

FIG. 60 shows a modification of the insertion unit. In this instance, jet port member 30 is provided rotatably on the outer periphery of connector member 242. Jet port member 30 has a single jet port 32, and it is driven from ultrasonic motor 244. With rotation of jet port member 30 caused by ultrasonic motor 244 the position or jet port 32 can be varied to vary the thrust direction.

High pressure fluid is supplied to jet port 32 from flexible tube 110 through peripheral groove 246.

Further, the sense of jet port 32, i.e., sense of the thrust direction, can be detected by encoder 248 for detecting the rotation of jet port member 30. Position data of jet port 32 provided from encoder 248 is displayed on display means as in the previous embodiment.

In this modification, only a single flexible tube 110 is sufficient, so that it is possible to reduce the diameter of insertion unit 6.

It is possible to provide means for detecting the direction of the thrust produced by the jet at a position different from pressure sensor so as to detect the thrust direction according to the aperture of pressure regulation valve.

FIGS. 61 to 66 show a sixth embodiment. FIG. 61 shows endoscope 2, which comprises operation unit 4, objective lens unit 18 provided on a rear part of operation unit 4, flexible insertion unit 6 coupled to a front part of operation unit 4 and universal cord 8 having light source connector 72 capable of being connected to external light source unit 74.

The distal end of insertion unit 6 is provided with end structure 14 having an observation window and a pair of illumination windows. Insertion unit 6 has first jet port 32 provided rearwardly of end structure 14 and second jet port 33 rearwardly spaced apart from first jet port 32 toward operation unit 4. First and second flexible tube 110 and 111 communicating with jet ports 32 and 33 are led from insertion unit 6 through operation unit 4 to light source connector 72 of universal cord 8.

On flexible tube 110 and 111 switching control valves 252 and 254 are provided as control means in operation unit 4. Each of switching control valves 252 and 254, as shown in FIG. 62, includes cylinder 256 mounted in operation unit 4 and piston 260 slidably inserted in cylinder 256 and sealed from the outside by O-ring 258. To cylinder 256 are connected insertion unit side and connector side flexible tube 110A and 110B. Piston 260 is upwardly biased by spring 262 to close insertion unit side flexible tube 110A. As shown in FIG. 63, when piston 260 is pushed against the biasing force of spring 262 insertion unit side flexible tube 110A having been closed by piston 260 is opened to be communicated with connector side flexible tube 110B. Further, although not shown, a fiber image guide extends from the observation window to objective lens unit 18, and a fiber lightguide extends from the illumination window to light source connector 72. Light source unit 74 accommodates a light source (not shown) and compressor 64 for supplying compressed air.

Now, the function of this embodiment of the endoscope will be described. When light soruce connector 72 of endoscope 2 is connected to light source unit 74 as shown in FIG. 61, the fiber lightguide is connected to the light source, thus enabling the illumination. Further, flexible tubes 110 and 111 are communicated with compressor 64 to permit supply of compressed air.

Now, compressor 64 is operated by turning on an operation switch (not shown) provided on light source unit 74 or endoscope 2. Compressed air generated from compressor 64 is supplied to flexible tubes 110 and 111.

As shown in FIG. 62, in each of switching control valves 252 and 254 each of insertion side flexible tubes 110A and 111A is closed by piston 260 biased by spring 262 to be at an upper position, so that no compressed air is supplied to jet ports 32 and 33. When piston 260 is pushed down against the biasing force of spring 262, insertion side flexible tube 110A or 111A having been closed by piston 260 is opened so that compressed air is supplied to jet port 32 or 33.

FIG. 64 shows insertion unit 6 with compressed air jet from first jet port 32 at its distal end by operating switching control valve 252. Insertion unit 6 is greatly curved upwardly with compressed air jet from jet port 32 directed downwards. Thus, insertion unit 6 can be readily inserted into piping 40 even having a stepped wall having a large height. Also, it is possible to observe a ceiling at a high level.

FIG. 65 shows insertion unit 6 with compressed air jet from second jet port by operating switching control valve 254. Again in this case, insertion unit 6 can be curbed upwards with compressed air jet from jet port 33 directed downwards. When compressed air is jet from first jet port 32, insertion unit 6 is curved to a small extent. This operation, therefore, is suited for inserting insertion unit 6 into ductline 40 having a stepped wall having a small height.

When compressed air is jet from both first and second jet ports 32 and 33 as shown in FIG. 66, insertion unit 6 can be curved into a form of figure S for the two jet ports are provided at diametrically opposite positions.

Further, by controlling the extent of pushing of pistons 260 in switching control valves 252 and 254 the apertures of insertion side flexible tubes 110A and 111A can be controlled to control the rate of jetting of compressed air. The shape of curving of insertion unit 6 and radius of curvature of the curving can be freely varied through control of the rate of jetting of compressed air even from the same jet port.

With the sixth embodiment, in which jet ports 32 and 33 are provided at a distance from each other in the axial direction of insertion unit 6, it is possible to insert insertion unit 6 to or observe a place where there is a stepped wall having a small or large height. Further, with the method of curving the insertion unit with operation wires, with long insertion unit 6 the curving response is inferior due to looseness or sagging of operation wires. With this embodiment, satisfactory curving response can be obtained for the insertion unit is curved with compressed air.

Figure 67:
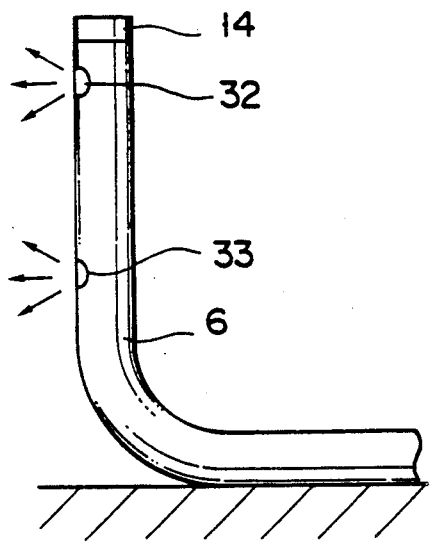
FIG. 67 is a side view showing a first modification of the sixth embodiment of the borescope.

FIG. 67 shows a first modification. In this instance, insertion unit 6 has jet ports 32 and 33 formed on the same side and at a distance from each other. Thus, with compressed air jet from both jet ports 32 and 33, insertion unit 6 can be curved to a greater extent than the case of jetting compressed air from only jet port 32 at the distal end. Further, since jet ports 32 and 33 are provided are provided on the same side, i.e., they are directed in the same direction, when switching first and second jet ports 32 and 33, there is no need of twisting insertion unit 6 for directing the jet ports downwards. Thus, the operability can be improved. Further, by increasing the rate of jetting of compressed air from first jet port 32, insertion unit 6 is warped rearwardly to permit observation of a backward place.

Figure 68:
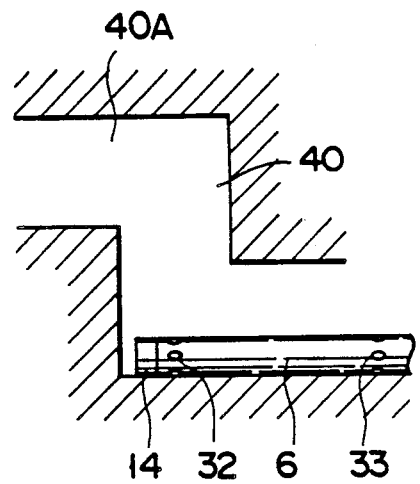
FIGS. 68 to 70 are side views showing a second modification of the insertion unit.
Figure 69:
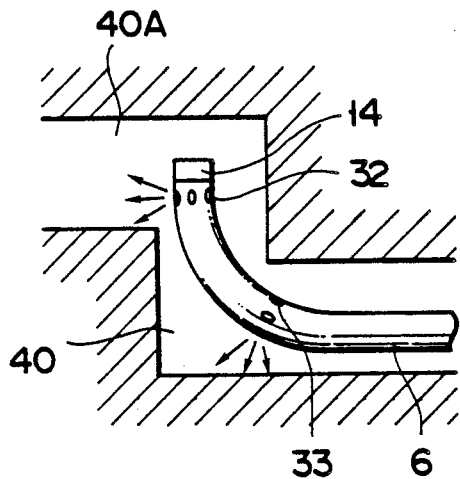
Figure 70:
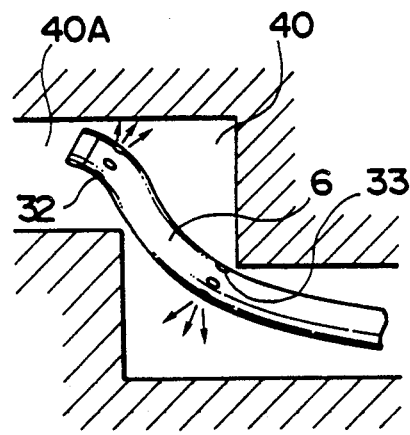

FIGS. 68 to 70 show a second modification. In this instance, four first jet ports 32 and four second jet ports 33 are provided at a uniform circumferential spacing.

Now, a method of inserting insertion unit 6 into piping 40 will be described. As shown in FIG. 68, insertion unit 6 is pushedly inserted to bring end structure 14 to be in ductline 40. Then, compressed air is jet from the lower one of first jet ports 32 to cause curving of insertion unit 6. In this state, insertion unit 6 is pushed forwards until end structure 14 appears in piping 40A. Then, as shown in FIG. 69, compressed air is jet from the lower one of second jet ports 33 to facilitate the insertion. By causing compressed air to be jet from first jet port 32 which is positioned on the opposit side of second jet poart 33, when end structure 14 reaches the inlet of inside ductline 40A, insertion unit 6 can be curved into a form of figure S. By further pushing forwards, insertion unit 6 may be inserted into inside ductline 40A.

It will be understood that with the provision of jet ports at a circumferential interval around the periphery of insertion unit 6, it is possible to omit the operation of redirecting the jet port to a downward direction. Further, since insertion unit 6 can be freely curved by selecting the jet port for use, it is possible to curve insertion unit 6 to suit various shapes of pipelines. It is possible to provide jet ports at three or more positions spaced apart in the axial direction of the insertion unit.

FIG. 71 shows a modification of a sixth embodiment. In this modification, operation unit 4 has jet port selection switches 264 and 266 and pressure control switch 268. Jet port selection switches 264 and 266 operate electromagnetic valves (not shown) provided in reservoir tank 180 through control circuit 270. As a result, compressed air is supplied to the selected jet port, e.g., jet port 32, through flexible tube 110 communicating with jet port 32. Further, by operating pressure control switch 268 the pressure of compressor 64 is controlled through control circuit 270. The extent of curving of insertion unit 6 can be varied through control of the extent of jetting of compressed air.

FIGS. 72 to 75 show a seventh embodiment of the invention. FIG. 72 shows endoscope 2 and light source unit 74 therefor. Endoscope 2 has operation unit 4, to which elongate insertion unit 6 and universal cord 8 are connected. Universal cord 8 branches into two branches. One of the branches has its end provided with light source connector 72 which is detachably coupled to light source unit 74. The other branch has its end detachably connected to reservoir tank unit 272 to be connected to compressor 64 shown in FIG. 75 via reservoir tank unit 272.

Insertion unit 6, as shown in FIG. 73, has flexible end portion 12, at the distal end of which end structure 14 is provided. The front end surface of end structure 14 has observation window 164, illumination window 168 and channel inlet 170. Observation window 164 is optically coupled to objective lens unit 18 of operation unit 4 via an image guide (not shown). Illumination window 168 is coupled to a light-guide (not shown). The light-guide is led through insertion unit 6, operation unit 4 and universal cord 8 to connector 2 and optically coupled to an illumination light source in light source unit 74 via light source connector 72.

Flexible end portion 12 of insertion unit 6 can be forcibly curved under remote control by operating angle knob 20 provided on operation unit 4, thus changing the direction of end structure 14.

Jet port member 30 is provided on the stem of flexible end portion 12. Jet port member 30, as shown in FIG. 7, is a cylindrical member having four, i.e., upper, lower, left and right, jet ports 32A to 32B formed on the outer periphery. Connector tubes 112A to 112D are connected to jet ports 32A to 32D. Flexible tubes 110 consisting of high pressure fluid supply tubes are connected to respective connector tubes 112A to 112D. They are led through insertion unit 6, operation unit 4 and universal cord 8 to be connected to reservoir tanks 273 in reservoir tank unit 272 connected to the end of one branch of universal cord 8. Each reservoir tank 180, as shown in FIG. 75, is connected to compressor 64 as high pressure fluid source.

Pressure regulator 276 is provided on ductline connecting each reservoir tank 180 and compressor 64. Each pressure regulator 276 has a variable setting point. These setting points are adjusted by setting point control knobs 278A to 278D provided on the outer surface of the body of reservoir tank unit 272. In this endoscope, control switches for controlling the rate of flow from jet ports 32A to 32D and jet port selection switch are assembled in external units such as light source unit 74 or reservoir tank unit 272 or operation unit 4 of endoscope 2.

As shown in FIG. 74, connector tubes 112A to 112D for jet ports 32A to 32D in jet port member 30 are provided with pressure sensors 280A to 280D for detecting the pressure of high pressure fluid. Pressure sensors 280A to 280D detect the pressure of high pressure fluid jetting from jet ports 32A to 32 through connector tubes 112A to 112D. It is possible to provide individual reservoir tanks 180 in reservoir tank unit 272 with respective pressure sensors 280A to 280D to detect the pressure in reservoir tanks 180. Pressure detection signals from pressure sensors 280A to 280D are used to automatically control pressure regulators 276 through a control circuit (not shown) to set pressure to predetermined setting points.

Now, the function of this embodiment of the endoscope will be described. Insertion unit 6 is gradually inserted into a piping while observing observation field. If high pressure air is being jet slightly form jet ports 32A to 32D, when end structure 14 of insertion unit 6 approaches the inner wall, it experiences a strong reaction force of high pressure fluid jetting from a jet port near the wall, so that it is separated from the wall surface. Thus, it is possible to reduce the frictional force o the end structure.

Then, by causing jet of high pressure fluid from a particular jet port selected by the jet port selection switch, flexible insertion unit 6 may be curved in the direction opposite to the jetting direction by the reaction force of the jet. Further, insertion unit 6 can be curved by controlling the rate of jetting from jet ports 32A to 32D; for instance, insertion unit 6 can be greatly curved by causing a strong jet from lower jet port 32A.

In this embodiment of the endoscope, the pressure of high pressure fluid from jet ports 32A to 32D is detected by pressure sensors 280A to 280D near jet ports 32A to 32D or near reservoir tanks 180. If the jet pressure is pulsating, pressure regulators 276 are automatically controlled by a control circuit (not shown), to which the detected pressure signals are supplied, so that the pressure is adjusted to predetermined setting points. That is, it is possible to remove pulsations of the pressure of light pressure fluid jetting form jet ports 32A to 32D and automatically adjust the pressure to preset pressures. Thus, since fluid is jet under preset pressures from jet ports 32A to 32D, it is possible to hold insertion unit 6 stably in a curved and floated state, prevent swinging of insertion unit 6 due to jet pressure pulsations and maintain a satisfactory observation state.

By causing jet from left and right jet ports 32C and 32D at controlled jet rates as well, insertion unit 6 may not only be curved upwards but also be tilted to the left or right.

In the seventh embodiment, flexible end portion 12 is provided at the distal end of insertion unit 6. Therefore, it is possible to vary the orientation of end structure 14 of insertion unit 6 by forcibly curving flexible end portion 12.

FIG. 76 shows a first modification of the seventh embodiment of the invention. In this modification, flexible tubes 110 communicating with jet ports 32A to 32D are provided, and a single reservoir tank 180 is connected to each flexible tube 110. Compressor 64 is connected as a high pressure source to reservoir tank. In other words, in this modification reservoir tank 180 and compressor 64 constitute high pressure fluid supply unit for supplying high pressure fluid to jet ports 32A to 32D.

Reservoir tank 180 is provided with pressure sensor 280 to detect the pressure of reservoir tank 180. Pressure regulator 276 is provided on ductline connecting reservoir tank 180 and compressor 64. Pressure regulator 276 is controlled by the control circuit according to a signal from pressure sensor 280 to hold a fixed pressure in reservoir tank 180.

FIG. 77 shows a second modification. In this instance, like the first modification, supply ductlines 110 are connected to respective jet ports 32A to 32D. Like the seventh embodiment, flexible tubes 110 are connected to reservoir tanks 180. Compressor 64 is connected as a high pressure source to reservoir tanks 180. In this second modification, three jet ports and three flexible tubes 110 are provided. Thus, pressure can be readily controlled by making the length of the individual ductlines the same to make constant the pressure of reservoir tanks 180.

FIGS. 78 to 81 show an eighth embodiment of the invention. As is shown in these Figures, this embodiment of endoscope 2 has elongate insertion unit 6 and operation unit 4, and universal cord 8 connected to external unit 284 is coupled to operation unit 4. Insertion unit 6 has flexible tube portion 10, flexible end portion 12 and end structure 14 connected in the mentioned order from the stem. Flexible end portion 12 can be curved under remote control by operating a curving mechanism provided in operation unit 4 with curving knob 20.

Figure 79:
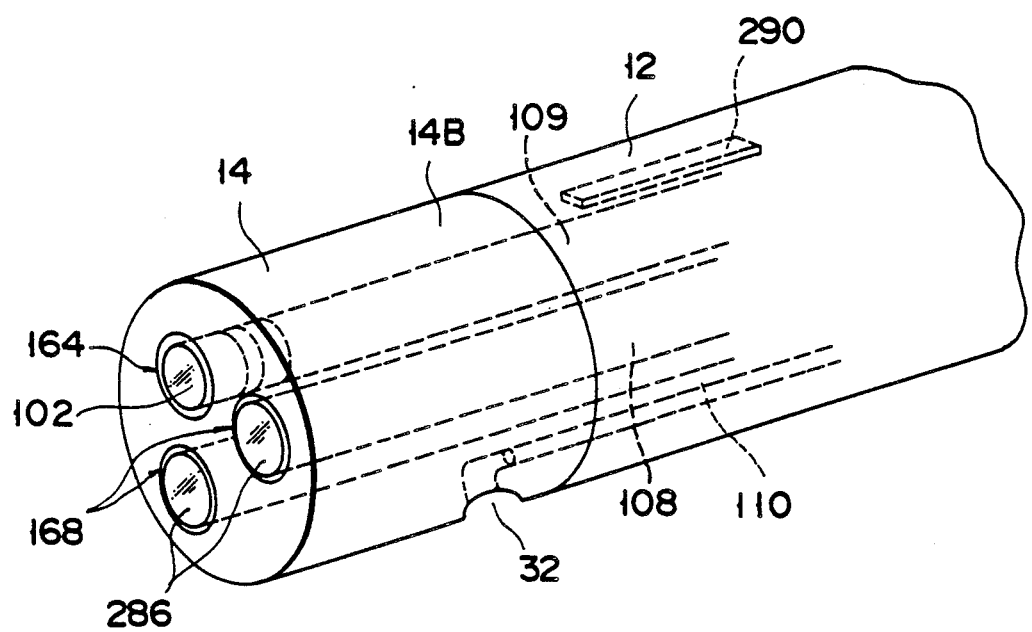
FIG. 79 is a perspective view showing the eighth embodiment of the borescope.

End structure 14 of insertion unit 6, as shown in FIG. 79, includes body 14B, the front end surface of which has illumination windows 168 and observation window 168. Fiber light-guides 108 are coupled to cover glasses 286 of illumination windows 168. Image guide fiber 109 is coupled to optical objective lens system 102 of observation window 164. Fiber light-guides 108 are led through insertion unit 6 and universal cord 8. Fiber light-guides 108 are coupled to an external light source. Image guide fiber 109 is led through insertion unit 6 and coupled to an objective lens system in objective lens section 18 of operation unit 14.

End structure body 14B has jet port 32 provided on the lower surface. Flexible tube 110 extending through insertion unit 6 is connected to jet port 32. High pressure fluid is supplied through flexible tube 110. High pressure fluid is jet from jet port 32 downwardly of end structure body 14B to float up insertion unit 6 with a thrust produced by the jet of high pressure fluid.

In this embodiment of the endoscope, strain gauge 290 as deformation detection means for detecting the extent of deformation of flexible tube 10 is provided in, for instance, flexible tube 10 of insertion unit 6. Strain gauge 290 is connected to external unit 284 through insertion unit 6 and universal cord 8.

Figure 78:
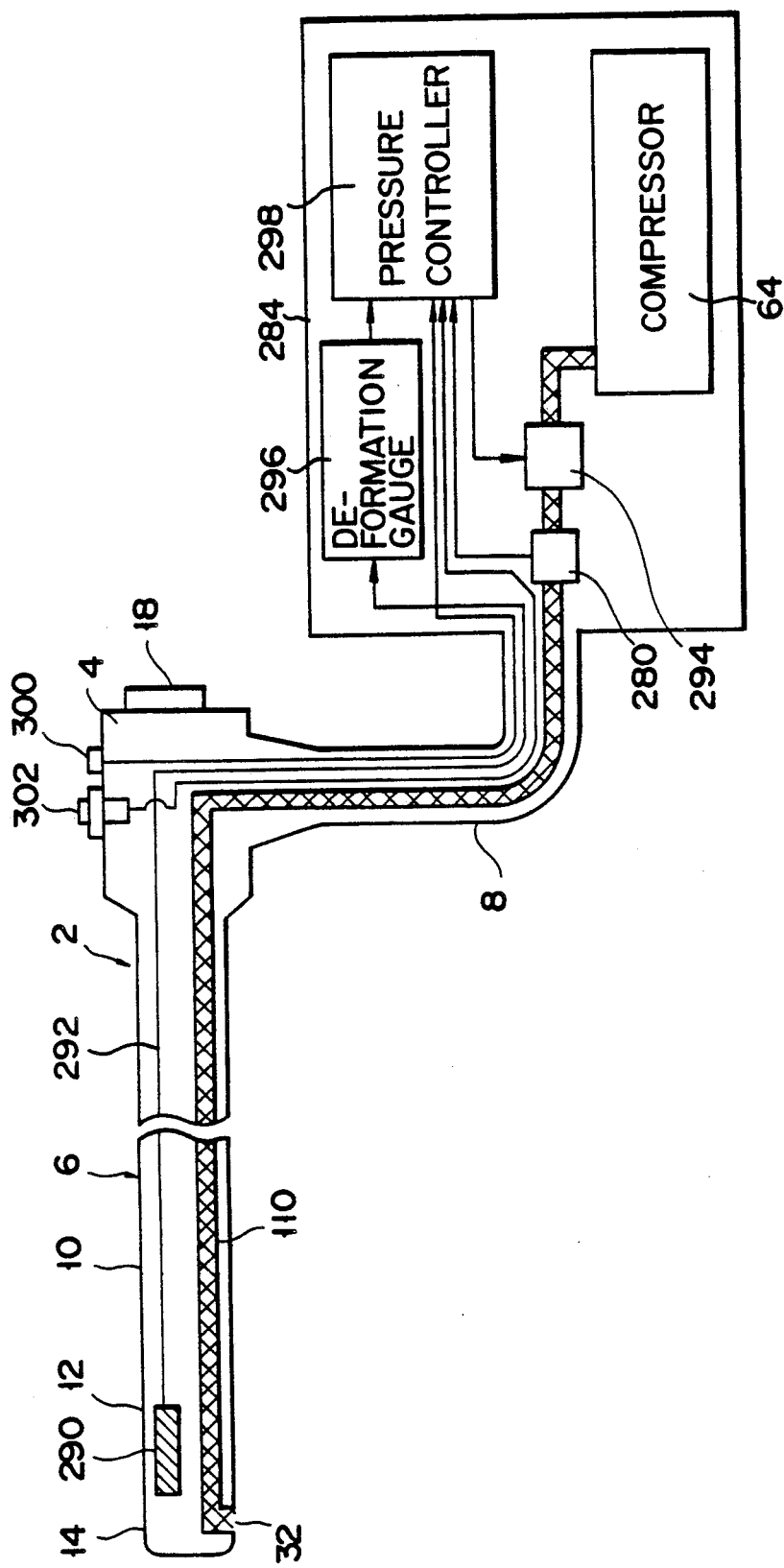
FIG. 78 is a block diagram schematically showing an eighth embodiment of the borescope according to the invention.
Figure 80:
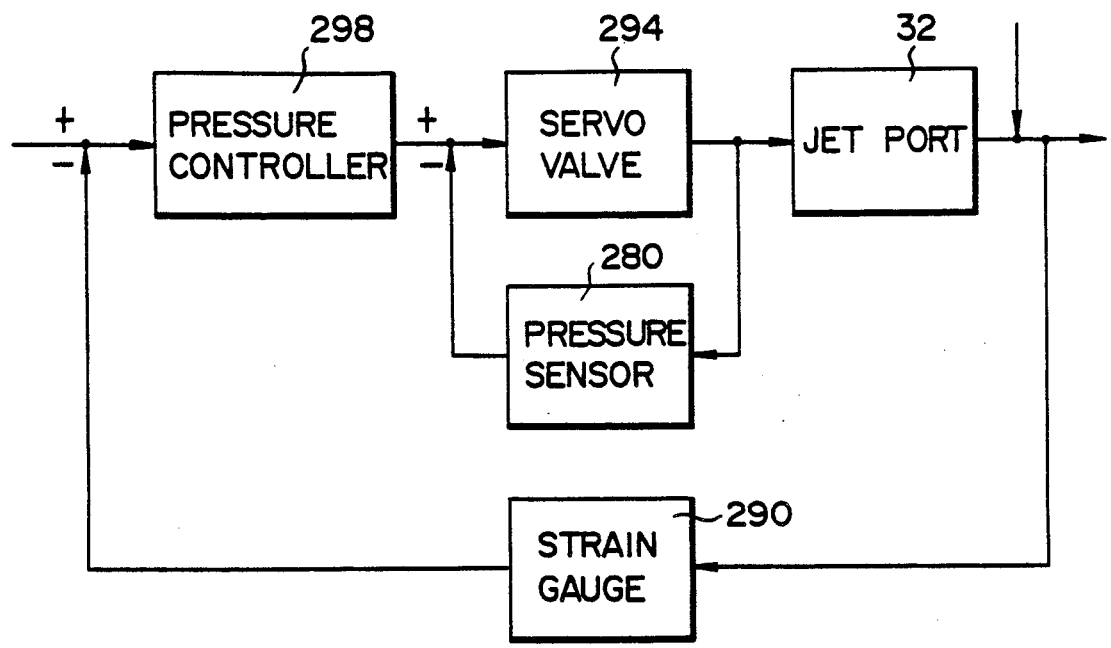
FIG. 80 is a block diagram showing a controller in the eighth embodiment of the borescope.

External unit 284 will now be described. As shown in FIGS. 78 and 80, external unit 284 includes compressor 64 as high pressure fluid source provided with a reservoir tank. Compressor 64 is communicated with servo valve 209 and pressure sensor 280 to flexible tube 110. External unit 284 includes deformation gauge 296, to which strain sensor 290 is connected via signal line 292. Deformation gauge 296 provides a detected deformation signal to pressure controller 298 constituting fluid pressure control means. Detected pressure signal from pressure sensor 280 is also supplied to pressure controller 298. Further, instruction signals are supplied from deformation setting switch 300 and still posture switch 302 provided on operation unit 4. According to these detection signals and instruction signals, pressure controller 298 provides a control signal to servo valve 294.

Now, the function of endoscope 2 will be described. Where there is stepped wall 38 inside subject 40 of observation, the sole curving of flexible end portion 12 is insufficient for the distal end of insertion unit 6 of endoscope 2 to clear stepped wall 38. Accordingly, high pressure air is supplied through flexible tube 110 to be jet from jet port 32 so as to cause insertion unit 6 to float up by a thrust by the jet of high pressure fluid from jet port 32. In this way, it is possible to let the distal end of insertion unit 6 to clear stepped wall 38. Further, the distal end of floated insertion unit 6 may be brought near, for instance, the ceiling of observation subject 40 to obtain sufficient observation.

As shown above, this embodiment of the endoscope has jet port 32 provided in end structure body 14B of insertion unit 6 so that an observation subject can be observed while floating insertion unit 6. The extent of deformation of flexible tube 10 of insertion unit 6 is detected by strain gauge 290. Strain gauge 290 provides a detected deformation signal supplied through signal line 242 to pressure controller 298 of external unit 284. It is thus possible to detect the actual deformation of flexible tube 10 and also detect the pressure of high pressure fluid jet from jet port 32 at this time with pressure sensor 280. Thus, by setting a desired extent of deformation by deformation setting switch 300 provided on operation unit 4, pressure controller 298 supplies an operation signal to servo valve 294 to control the aperture of servo valve 294. While detecting the pressure of high pressure fluid supplied to jet port 32 with pressure sensor 280 the aperture of servo valve 294 is controlled to provide a pressure corresponding to the preset extent of deformation of insertion unit 6. When the preset pressure is reached, the aperture of servo valve 294 is fixed to maintain a predetermined extent of deformation of flexible tube 10 of insertion unit 6. At this time, the extent of deformation of flexible tube 10 of insertion unit 6 is detected by strain gauge 290 at all time and controlled by pressure controller 298 through a feedback loop, so that it is possible to absorb a change in the deformation extent due to external disturbance.

Further, since the extent of deformation is flexible tube 10 of insertion unit 6 is detected by strain gauge 290 and the detected deformation signal is supplied to pressure controller 298, if it is desired to hold insertion unit 6 still as soon as a desired extent of deformation of flexible tube 10 is reached, still posture switch 302 provided on operation unit 4 is operated. As a result, an instruction signal is supplied to pressure controller 298. Pressure controller 298 thus supplies an operation signal to servo valve 294 to fix the aperture of servo valve 294 to hold the prevailing posture of flexible tube 10 of insertion unit 6.

While in the eighth embodiment strain gauge 290 has been used as deformation detection means, it is possible to use conductive rubber or potentiometer as well. Further, it is possible provide a plurality of deformation detection means in insertion unit 6. Further, while pressure sensor 280 has been provided in external unit 284, it may be provided in a portion of insertion unit 6 near jet port 32 as well.

Figure 82:
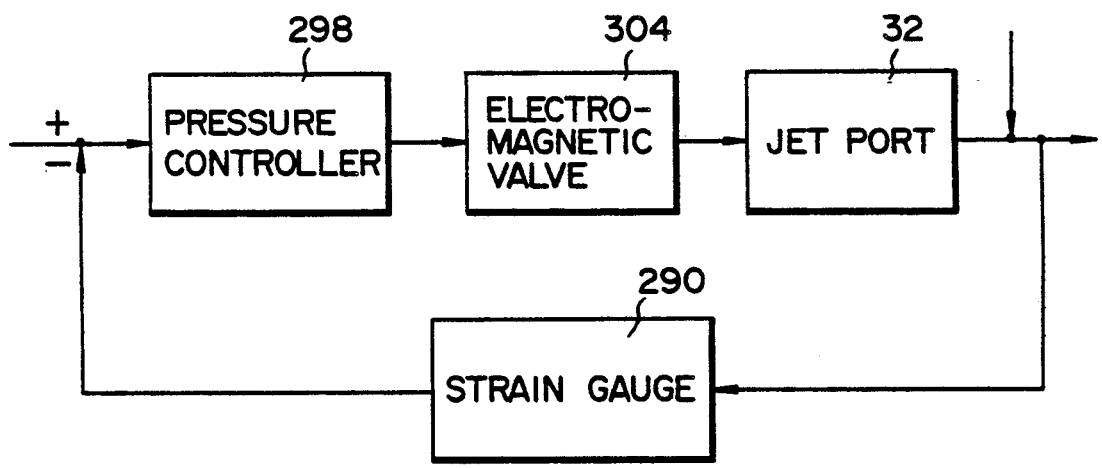
FIG. 82 is a block diagram showing a modification of the controller.

FIG. 82 shows a modification of the external unit of the eighth embodiment. In this modification, electromagnetic valve 304 is used in lieu of servo valve 294 in the eighth embodiment. As in the eighth embodiment the aperture of electromagnetic valve 304 is varied according to an operation signal from pressure controller 298. This modification does not provide for pressure feedback by pressure sensor 280, so that the accuracy is reduced. However, it is possible to reduce cost and simplify the construction compared to the eighth embodiment.

FIGS. 83 to 87 show a ninth embodiment of the invention. This embodiment concerns electronic endoscope 60, which comprises soft insertion unit 6 and operation unit 4. Insertion unit 6 flexible tube portion 10 capable of being bent according to external applied force, flexible end portion 12 coupled to the end of flexible tube portion 10 and end structure 14. Flexible end portion 12 can be forcibly curved under remote control by operating a knob on operation unit 4. Cable 66 is coupled to operation unit 4 of endoscope 60.

End structure 14 of insertion unit 6 has an observation window of an optical observation system and illumination windows of an optical illumination system. The optical observation system has objective lens 102 and solid-state image sensor element 104. It photographs the field through the observation window, and its image signal is transmitted to a peripheral unit connected to cable 66 for display on a TV monitor.

Jet port member 30 is provided between flexible tube portion 10 and flexible end portion 12. Jet port member 30 has downwardly directed jet port 32. Insertion unit 6 can be partly intermittently floated with a fluid, e.g., air, downwardly jet intermittently from jet port 32. Jet port 32 is connected to flexible tube 110 extending through insertion unit 6, operation unit 4 and cable 66. Pressurized fluid from a fluid source provided outside endoscope 60 is supplied intermittently through flexible 110 to jet pet 32.

Figure 84:
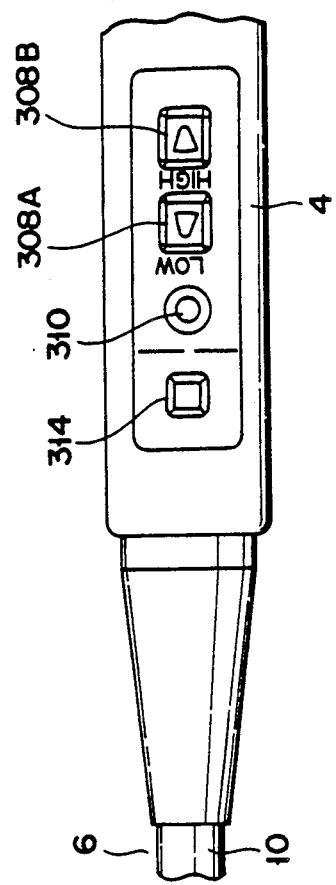
FIG. 84 is a plan view showing an operation section of the borescope shown in FIG. 83.

The fluid source consists of a compressor or a pump, and it includes control means for intermittently supplying fluid and controlling the pressure and rate of flow of fluid and also timing of intermittent supply. The supply pressure and rate of flow are controlled by pressure control switches 308A and 308B provided on operation unit 4 as shown in FIG. 84. Operation unit 4 further has operation switch 310 for selecting the mode of intermittent jetting.

Figure 85:
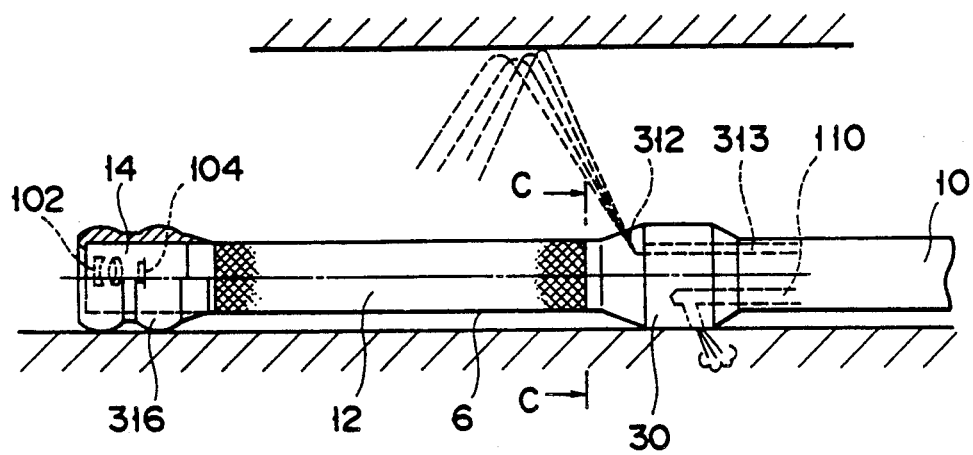
FIG. 85 is a side view showing an insertion unit of the borescope shown in FIG. 83.

As shown in FIG. 85, an upper portion of jet port member 30 is provided with obliquely forwardly directed jet port 312. Jet port 312 is connected to flexible tube 110 extending through insertion unit 6, operation unit 4 and cable 66. Pressurized liquid is supplied from a liquid source provided outside endoscope 60 through flexible tube 110 to be jet obliquely forwardly from jet port 312. The jetting operation is caused by jetting switch 314 provided on operation unit 4 shown in FIG. 84.

Buffering protective cover 316 of rubber or like elastic material is removably mounted on end structure 14 of insertion unit 6. Protective cover 316 has opposite end and intermediate reduced-diameter portions. Alternatively, longitudinal grooves may be formed such that they extend in the axial direction of insertion unit 6.

Operation unit 4 has release frame switch 124 for temporarily storing an image detected by solid-state image sensor element 104 of the optical observation system in a peripheral unit connected to cable 66 to make the image still and release switch 126 for providing an image output to an image printer.

In the use of this embodiment of endoscope 60, elongate insertion unit 6 is pushedly inserted into an observation subject. However, when an intermediate portion of insertion unit 6 meanders progressively and the inserted length exceeds 4 m, for instance, the meandering can no longer be ignored, and a phenomenon of failure of sufficient advancement of insertion unit 6 due to insufficient transmission of pushing force from the stem side to the distal end side becomes pronounced. If the phenomenon is pronounced, the pushing force is absorbed by the meandering portion to further increase the meandering, and the end structure 14 can no longer be advanced.

Figure 86:
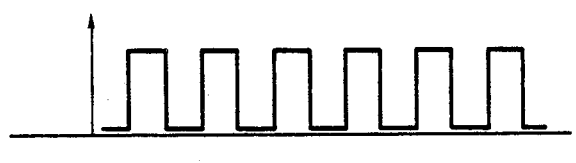
FIG. 86 is a graph showing the relation between time and jetting of fluid.

While fluid is intermittently jet from jet port 32, an optimum jet pressure is set in advance by operating control switches 308A and 308B depending on the status of inner space of the observation subject. Then, fluid is jet intermittently from jet port 32 by operating operation switch 310 of operation unit 4. More specifically, as shown in FIG. 86, fluid is jet intermittently, so that by intermittently receiving a thrust produced by the jet a corresponding portion of insertion unit 6 is floated up intermittently, that is, it is repeatedly floated up and lands. Such vertical meandering is progressively transmitted from the distal end side to the stem side of insertion unit 6. This action has an effect of providing for a regular meandering, so that insertion unit 6 becomes to proceed a substantially straight and shortest path. Thus, the pushing forced applied to the stem can be transmitted without loss to the distal end side, so that insertion unit 6 can be inserted up to a deep position. Further, the meandering has an effect of reducing the frictional resistance, i.e., insertion resistance, offered to insertion unit 6. Thus, insertion unit 6 can be inserted more smoothly and to a deeper position.

Figure 83:
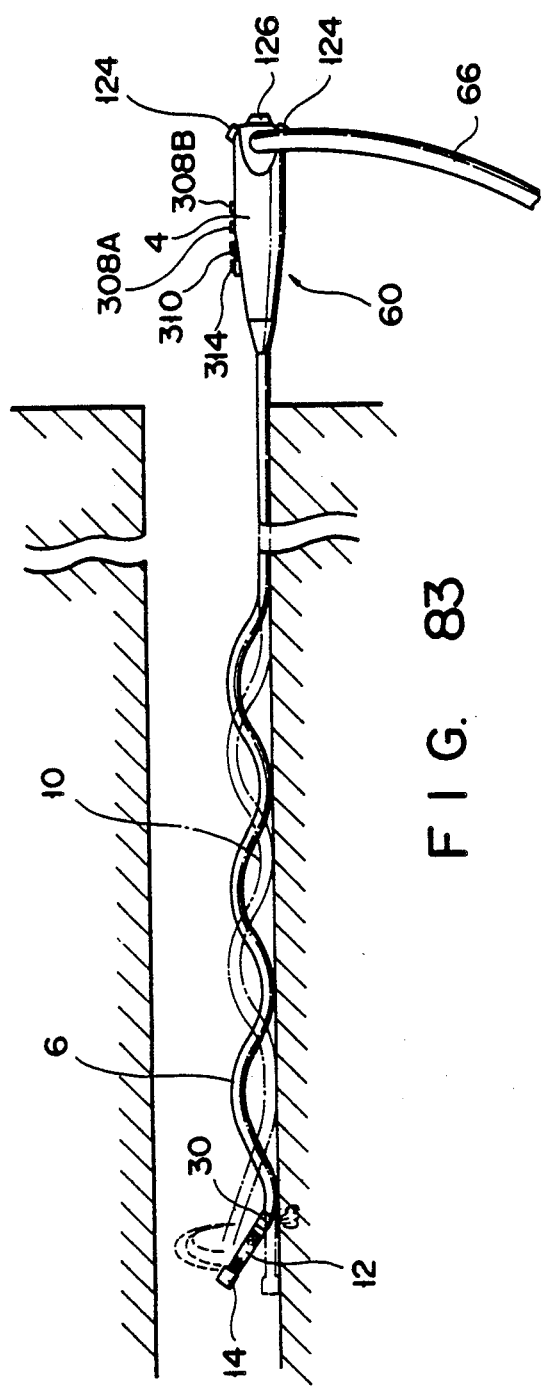
FIG. 83 is a perspective view showing a ninth embodiment of the borescope according to the invention.
Figure 87:
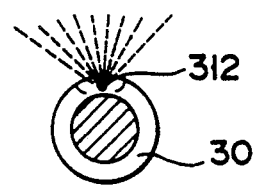
FIG. 87 is a transversal sectional view taken along C—C in FIG. 85.

In case when the status of the inner space of the observation subject is inadequate for observation, e.g., when it is extremely dry or there is accumulated dust, the observation surface is cleaned by jetting a cleaning liquid from jet port 312 by operating jetting switch 314 as shown in FIGS. 85 and 87. Further, when the observation window surface of the optical observation system is contaminated, the contamination may be removed by upwardly curving flexible end portion 12 or to direct it in the jetting direction or direction of falling of the jet fluid as shown in FIG. 83.

Figure 88:
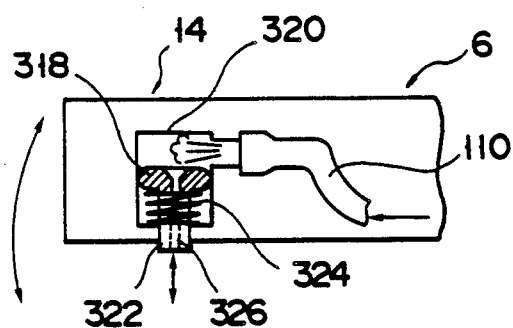
FIG. 88 is a schematic view showing an insertion unit of a first modification of the ninth embodiment.
Figure 89:
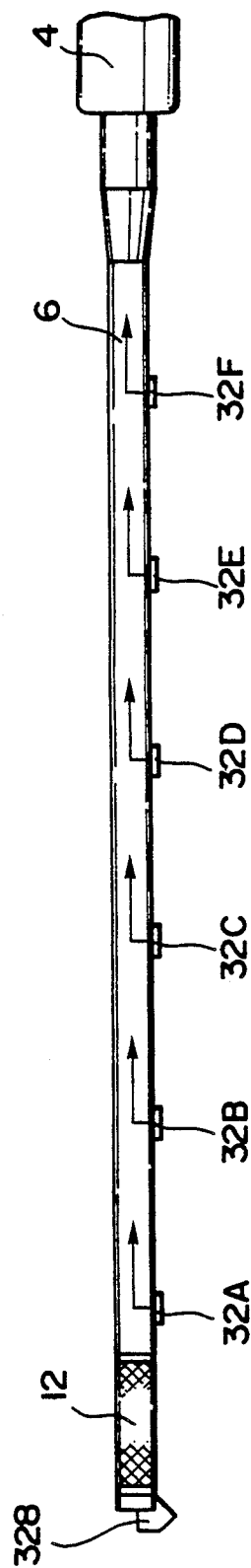
FIG. 89 is a side view showing an insertion unit of a second modification of the ninth embodiment of the borescope.
Figure 90:
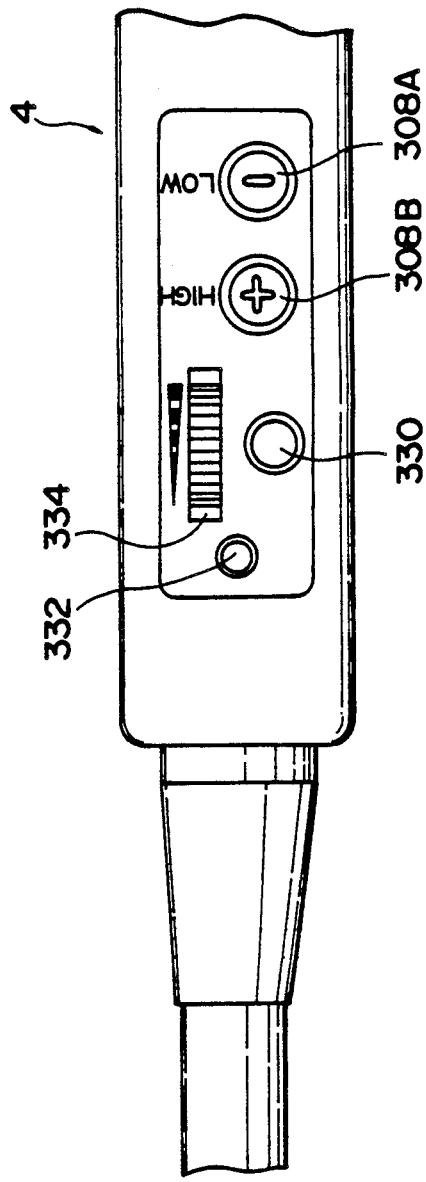
FIG. 90 is a plan view showing an operation unit of the borescope shown in FIG. 89.

FIG. 88 shows a first modification of the nine embodiment of the invention. In this modification, end structure 14 of endoscope 60 is provided with hammer 318, which can intermittently raise insertion unit 6. More particularly, hammer 318 is slidably inserted in cylinder 320 formed inside end structure 14. It has tapping part 322 which can be projected out of and retreated into the outer periphery of end structure 14 with its sliding. Hammer 318 is biased by coil spring 324 in a direction of causing retreat of tapping part 322 from the outer periphery of end structure 14. Narrow discharge port 326 penetrates hammer 318 to communicate the bottom space of cylinder 320 with the outside. Flexible tube 110 are communicated with the bottom space of cylinder 320. As in the ninth embodiment, they extend through insertion unit 6, operation unit 4 and cable 66. They are connected to a fluid source disposed outside endoscope 60, and pressurized fluid from the fluid source is intermittently supplied to the bottom space of cylinder 320. In this case, the fluid source consists of a compressor or a pump, and it includes control means for intermittently supplying fluid and controlling the supply pressure and flow rate and intermittent timing. The supply pressure and rate of flow is controlled by pressure control switches 308A and 308B provided on operator unit 4 as in the ninth embodiment of FIG. 84. Further, the intermittent supply is controlled by intermittent jetting mode control switch 310 of operation unit 4.

Thus, in this first modification by selecting the supply pressure with pressure control switches 308A and 308B and operating intermittent jetting mode control switch 310, the pressurized fluid from the fluid source is supplied intermittently to the bottom space of cylinder 320. When the pressurized fluid is supplied, hammer 318 is pushed against the biasing force of coil spring 324 so that its tapping part 322 is projected to tap the surface, on which end structure 14 rests. As a result, end structure 14 is raised by the reaction force. When the supply of fluid is stopped, fluid continuously escapes through narrow discharge port 326 of hammer 318. Hammer 318 thus is restored by the restoring force of coil spring 324, so that tapping part 322 is retreated from the outer periphery of end structure 14. In this way, by intermittently supplying fluid to cylinder 320 hammer 318 is reciprocated to cause repeated advancement and retreat of tapping part 320 to intermittently tap the surface, thus intermittently floating up end structure 14. End structure 14 thus is repeatedly floated and landed. In this way, the vertical motion of end structure 14 constitutes produces a meandering motion progressively transmitted from the distal end side to stem side of insertion unit 6. With this movement, the meandering of the insertion unit is arranged, so that the insertion unit proceeds along substantially a straight and shortest path in the insertion space. Thus, the pushing force from the stem side can be transmitted without loss to the distal end side, so that insertion unit 6 can be inserted to a deeper position.

Now, a second modification will be described with reference to FIGS. 89 to 94. Insertion unit 6 of the endoscope shown in FIG. 89 has six, first to sixth, jet ports 32A to 32F formed at a interval in the axial direction of insertion unit 6 for causing floating thereof. Flexible end portion 12 has jet port 328 provided at the distal end for propulsion. Further, operation unit 4 has thrust control switches 308A and 308B, switch 330 for controlling a insertion unit-floating mechanism control, pilot lamp 332 which is turned on when the floating mechanism is rendered operative, and interval control switch 334. Thrust control switches 308A and 308B control the rate of jetting from the jet port for propulsion, and the amplitude of floating can be varied through control of the jetting time with an interval controller.

Figure 91:
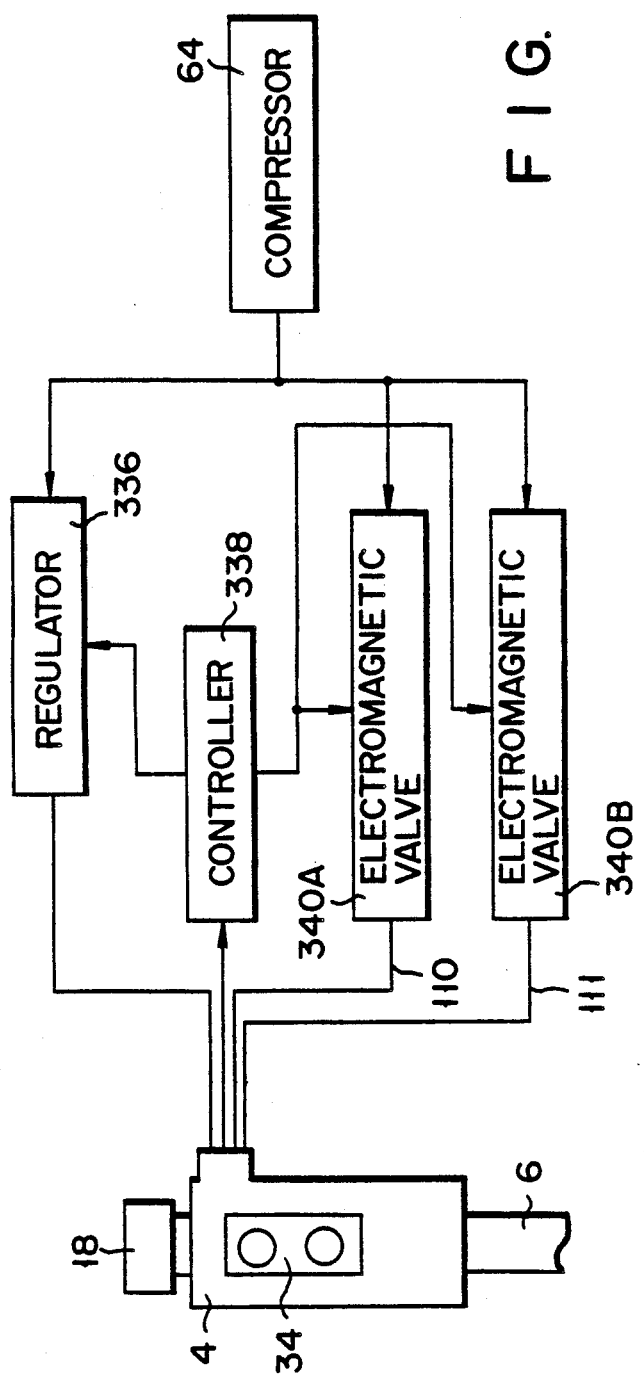
FIG. 91 is a block diagram showing a controller in a second embodiment of the borescope.
Figure 92:
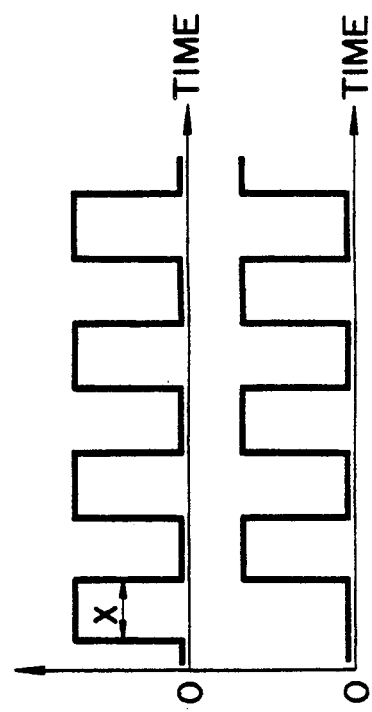
FIG. 92 is a graph showing the relation between time and pressure.

FIG. 91 shows a second modification of the endoscope system. The system includes regulator 336 connected to pressurized fluid source 64, two-port electromagnetic valves 340A and 340B and controller 338 for controlling two-port electromagnetic valves 340A and 340B from a signal from control switch 34. First electromagnetic valve 340A is communicated with first, third and fifth jet ports 32A, 32C and 32B through first flexible tube 110, and second electromagnetic valve 340B is connected to second, fourth and sixth jet ports 32B, 32D and 32F via second flexible tube 111. Thus, when pressure is supplied from pressurized fluid source 64 through electromagnetic valves 340A and 340B to individual group jet ports according to a control signal at timings as shown in FIG. 92, insertion unit 6 is advanced in a meandering fashion as shown in FIG. 93 or 94.

FIGS. 95 and 96 show a third modification. In this instance, 3-port electromagnetic valve 342 is used. In 3-port electromagnetic valve 342, as shown in FIG. 96, pressurized fluid source 64 is connected to a inlet port, first, third and fifth jet ports 32A, 32C and 32E are connected to first outlet port through first flexible tube 110, and second, fourth and sixth jet ports 32B, 32D and 32F are connected to second outlet port through second flexible tube 111.

Now, a tenth embodiment will be described with reference to FIGS. 97 to 102. FIG. 97 schematically shows a distal end portion of the endoscope, FIG. 98 shows the structure of the distal end portion in detail, and FIG. 99 is a sectional view showing the distal end. This embodiment of the endoscope includes insertion unit 6. The distal end of insertion unit 6 has observation window 164 and illumination windows. As shown in FIG. 98, to observation window 164 solid-state image sensor element (CCD) 104 via optical objective lens system 102 as shown in FIG. 98, and the observation image can be picked up through observation window 164. Further, the illumination windows are optically coupled to fiber light-guide 108 through an optical illumination system.

Figure 101:
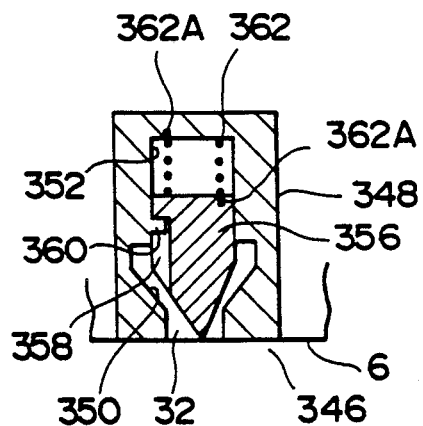
FIGS. 101 and 102 are sectional views for explaining valve operation.
Figure 102:
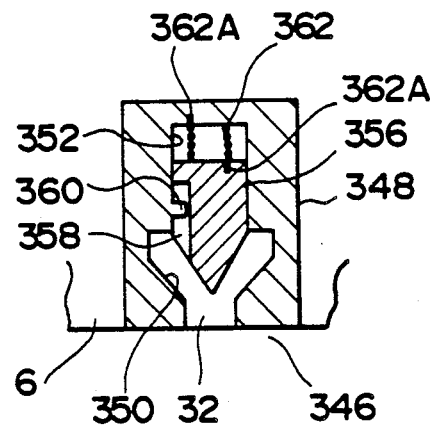

Now, regulation valve 346 mounted in the distal end of the endoscope will be described. Pressure regulation valve 346 includes valve body 348. Valve body 348, as shown in FIGS. 98 and 99, has substantially conical valve on/off chamber 350 and cylindrical valve accommodation chamber 352 therewith. Valve body 348 is buried in the distal end of insertion unit 6 in a direction normal to the axial direction of insertion unit 6 to open an outlet port of valve on/off valve 350 to the outer periphery of insertion unit 6. Jet port 32 noted above, is a small-diameter outlet port open to the outside. Valve body 348 is secured by set screw 354. Valve on/off chamber 350 and high pressure fluid source 64 provided outside the endoscope are connected to each other by flexible supply tube 110 inserted through insertion unit 6, and high pressure fluid under a fixed pressure, e.g., high pressure air, is supplied to high pressure valve 346. Pin-like valve 356 is slidably inserted in valve accommodation chamber 352 with its conical end portion disposed in valve on/off chamber 350, and the aperture of jet port 32 can be varied with the advancement and retreat of valve 356. As shown in FIGS. 101 and 102, the outer periphery of valve 356 has guide groove 358 extending in the axial direction. The inner periphery of valve accommodation chamber 352 is formed with projection 360 fitted in guide groove 358, so that valve 356 can be moved in a predetermined range. Between the rear end surface of valve 356 and inner wall of valve accommodation chamber 352, coil-like shapememorizing alloy piece (SAM coil) 362 is secured by coil securement member 362A. SMA coil 362 uses has such a shape that the coil length is reduced with increasing temperature. As shown in FIG. 100, SMA coil 362 and energization section 364 are connected to each other via lead 366 inserted through insertion unit 6. Controller 370 with a microcomputer is connected to energization section 364. By operating operating section 368, SMA coil 362 can be caused to shrink by self-heat-generation. Thus, valve 356 can be retreated to effect control of the rate of jetting from jet port 32.

Pressure sensor 280 is provided on the periphery of an outlet port near jet port 32 to detect the pressure of high pressure air that is jet. Pressure sensor 280 is connected to controller 370 to feed back the pressure of high pressure air that it jet. SMA coil 362 is interlocked to the feedback pressure signal to provide for a rate of flow preset by operating section 368.

With this embodiment of the endoscope, when floating the distal end of insertion unit 6, high pressure fluid, e.g., high pressure air under a constant pressure, is supplied from high pressure fluid source 64 to jet port 32, and operating section 36 is set to a desired floating capacity. By so doing, the end of insertion unit 6 is floated with generation of a corresponding reaction.

More particularly, when SMA coil 36 is not energized, valve body 356 of regulation valve 346 is located in the lowest position to provide a smallest aperture of jet port 32, as shown in FIG. 101. Since the pressure of high pressure air is fixed, the rate of jetting is minimum, and a small reaction force is exerted to insertion unit 6. The thrust is thus low, and insertion unit 6 is floated with a small angle.

When SMA coil 362 is energized by operating operating section 368, it shrinks with self-heat-generation, and valve body 356 is gradually retreated with temperature rise as shown in FIG. 102. As a result, the aperture of jet port 32 is gradually increased. At this time, controller 370, receiving a signal from pressure sensor 280, holds the pressure of high pressure air jet from jet port 32 at a preset value set in operating section 368, thus maintaining a flow rate corresponding to the operation of operating section 368. Thus, various reaction forces can be exerted according to the distal end of insertion unit 6 according to the operation of operating section 368. A high thrust thus can be obtained according to the operation to cause insertion unit 6 to float up with a large angle. In this embodiment, various thrusts can be obtained without control of high pressure fluid source 64.

Figure 103:
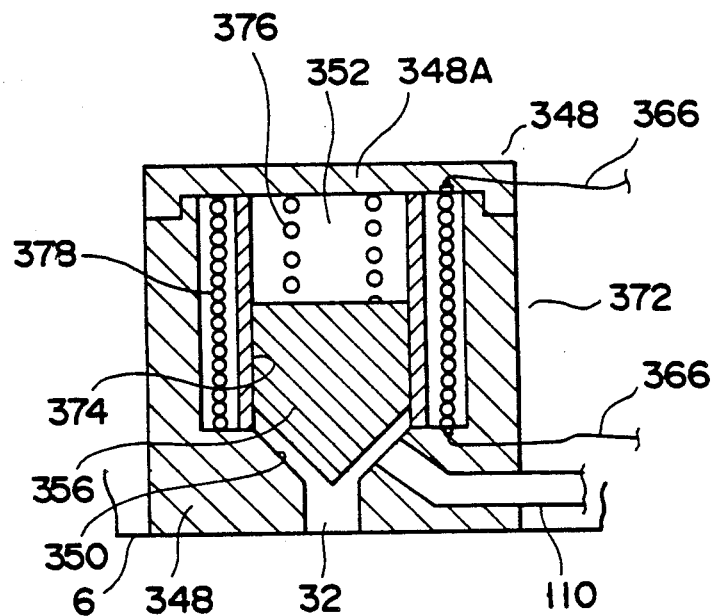
FIG. 103 is a sectional view showing a modification of an operation section.

FIG. 103 shows a modification of a tenth embodiment. In this instance, solenoid 372 is used in lieu of SMA coil 362 as pressure regulation means. Solenoid 372 has a cylindrical member 374 defining valve accommodation chamber 352, and ceramic coil spring 376 is provided between the rear end of valve 356 and valve accommodation chamber end. Valve 356 is normally biased downwards by coil spring 376 so that its end surface closes the opening of supply tube 110 connected to valve on/off chamber 352. Electromagnetic coil 378 is mounted on the outer periphery of cylindrical member 374. By causing current to pass through electromagnetic coil 378 through lead 366, valve 356 is raised against the elasticity of ceramic coil spring 376 to open the opening of supply tube 110.

In this modification, since cylindrical member 374 accommodates ceramic coil spring 376, valve body 348 has a two-part structure consisting of lid 348A and body 348B.

Figures 104, 105, 106:
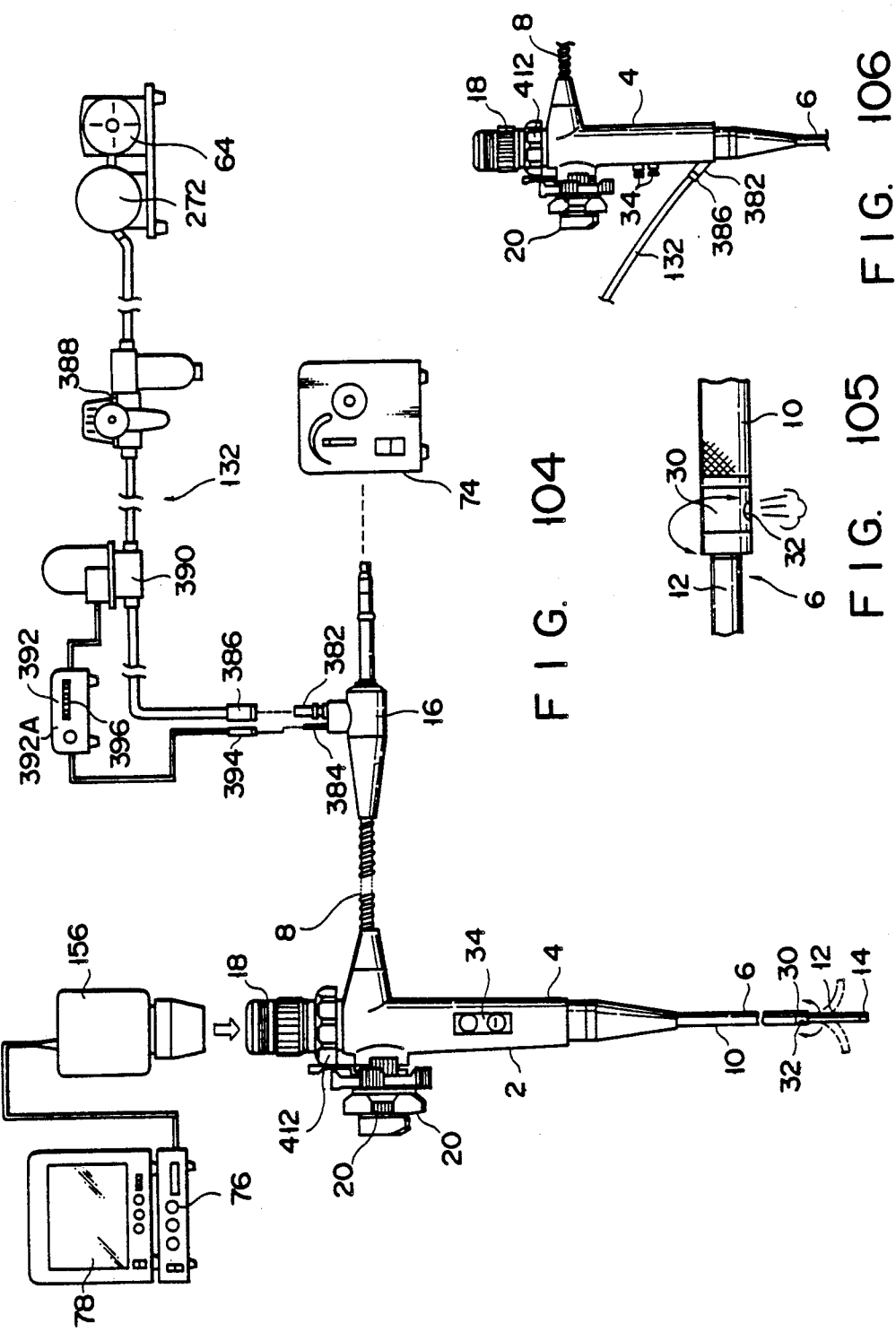
FIG. 104 is a side view showing an eleventh embodiment of the borescope according to the invention.
FIG. 105 is a side view showing an insertion unit shown in FIG. 104.
FIG. 106 is a side view showing a modified operation section shown in FIG. 104.

Now, an eleventh embodiment of the invention will be described with reference to FIGS. 104 to 119. FIG. 104 schematically shows this embodiment of the endoscope system. Insertion unit 6 and universal cord 8 are coupled to operation unit 4 of endoscope 2. Insertion unit 6 has end structure 14 coupled via bending portion 12 to flexible tube portion 10. Bending portion 12 is forcibly curved under remote control by operating knob 20 provided on operation unit 4. The observation image through endoscope 2 can be observed with an eye through objective lens section 18 of operation unit 4, and can be electronically photographed by TV camera 156 with adopter removably mounted on objective lens section 18. TV camera 156 is connected to camera control unit 76. A video signal from TV camera 156 is processed in camera control unit 76 before being transmitted to TV monitor 78 for display of observation image.

Figure 109:
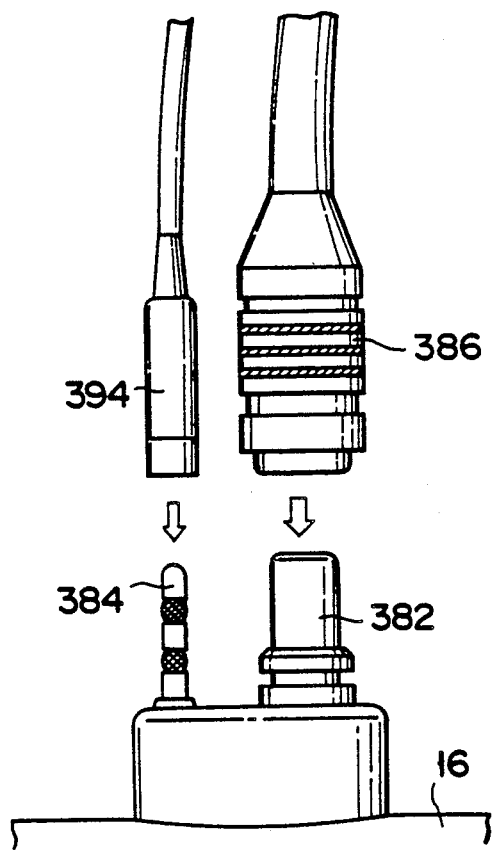
FIG. 109 is a plan view showing a connector in the eleventh embodiment of the borescope.

Connector 16 mounted on the end of universal cord 8 extending from operation unit 4 of endoscope 2 is removably connected to illumination light source unit 74. Connector 16, as shown in FIG. 109, has high pressure fluid terminal 382 and signal terminal 384. As shown in FIG. 104, high pressure fluid supply unit 132 is removably connected by a one-touch system via fluid coupling 386 to high pressure fluid terminal 382. High pressure fluid supply unit 132 has compressor 64 with pressure-smoothing reservoir tank 272, air filter 88 and air regulator 390. Air regulator 390 has an electromagnetic on/off valve and an electromagnetic throttle valve. These valves are controlled by controller 392 for regulator, thereby the supply operation and rate of supply can be controlled. Operation unit 4 of endoscope 2 has operation switch 34, which is connected through a signal cable extending through universal cord 8 to signal terminal of connector 16. Signal terminal 384 can provide an operation instruction to regulator controller 392 through signal connector 394. Like instruction may also be provided from switch 396 provided on body 392A of regulator controller 392.

Figure 110:
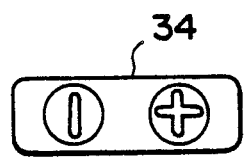
FIGS. 110 to 113 are plan view and side views showing a switch in an operation unit.
Figure 111:
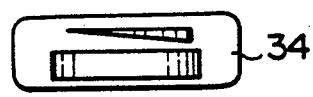
Figure 112:
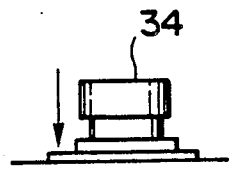
Figure 113:
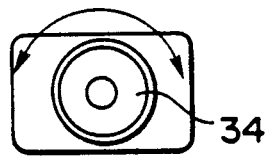

Operation switch 34 provided on operation unit 4 may be of various types as shown, for instance, in FIGS. 110 to 113. The switch shown in FIG. 110 is a push-button switch for flow rate control. The switch shown in FIG. 111 is a dial switch for flow rate control. The switches Shown in FIGS. 112 and 113 can control the flow rate with a combination of dial system and push button system.

Figure 107:
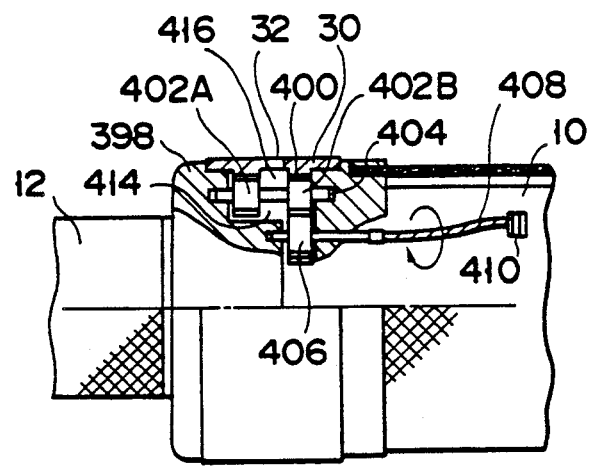
FIG. 107 is a fragmentary sectional view showing an insertion unit of the eleventh embodiment.
Figure 108:
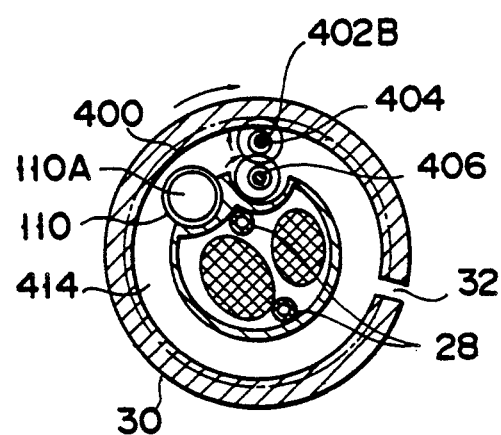
FIG. 108 is a transversal sectional view showing a rotary member shown in FIG. 107.

Insertion unit 6 has jet port member 30 rotatably mounted adjacent to the stem of flexible end portion 12. Jet port member 30, as shown in FIGS. 107 and 108, is cylindrical in shape and rotatably mounted on the outer periphery of member 398 connecting flexible tube portion 10 and flexible end portion 12 of insertion unit 6. Jet port member 30 has inner gear 400, which is meshed with a pair of small gears 402A and 402B mounted on shaft member 398 inside jet port member 30. Small gears 402A and 402B are secured to shaft 404 and rotated in unison with each other. Small gear 402B is in mesh with drive small gear 406 supported on shaft member 398. The gear mechanism including small gears 402A and 402B and small gear 406 provided inside of jet port 30 constitutes drive means for varying the circumferential position of jet port 32. Drive small gear 406 is coupled to transmission wire 408 for transmitting torque, and it is rotated by torque transmitted to transmission wire 408. Transmission wire 408 is guided by guide tube 410 extending through insertion unit 6 and coupled to a drive mechanism (not shown) provided inside operation unit 4. The drive mechanism can be operated by knob 412 provided on operation member 4 shown in FIG. 104 for setting the direction and extent of rotation transmitted transmission wire 408. Thus, jet port member 30 can be rotated under remote control by operating knob 412 in operation unit 4.

The gear mechanism having small gears 402A, 402B and 406 provided inside jet port member 30 is found in sealed space 414 defined inside jet port member 30. The inner periphery of jet port member 30 has central circumferential groove 416. A portion of circumferential groove 416 has jet port 32, from which fluid supplied through sealed space 414 can be jet. Jet port 32 is directed perpendicularly to the axial direction of insertion unit 6 or obliquely with respect to the direction of operation unit 4. Insertion unit 6 can be floated up by jetting high pressure fluid, e.g., air, from jet port 32 in the radial direction of insertion unit 6.

Sealed space 414 communicates with fluid supply passage 110A. Passage 110A consists of tube 110 extending through insertion unit 6, operation unit 4 and universal cord 8 and connected to high pressure fluid terminal 382 of connector 16. While high pressure fluid terminal 382 is provided on connector 16, it may be provided on operation unit 4 as shown in FIG. 106. Operation unit 4 has curving knob 20 for curving flexible end portion 12 via operation wires 28 under remote control.

Now, the function of this embodiment of the endoscope system will now be described. Connector 16 is connected to illumination light source unit 74, and high pressure fluid supply unit 132 is connected to high pressure fluid terminal 382. Further, regulator controller 392 is connected to signal terminal 384. Now, endoscope 2 can be used. For obtaining image display on TV monitor 78, TV camera 156 is mounted on objective lens section 18.

Now, insertion unit 6 of endoscope 2 is inserted into the inner space of subject 418 of observation. If necessary, insertion unit 6 may be guided to a certain depth by using guide tube 420 as shown in FIG. 114.

Figure 114:
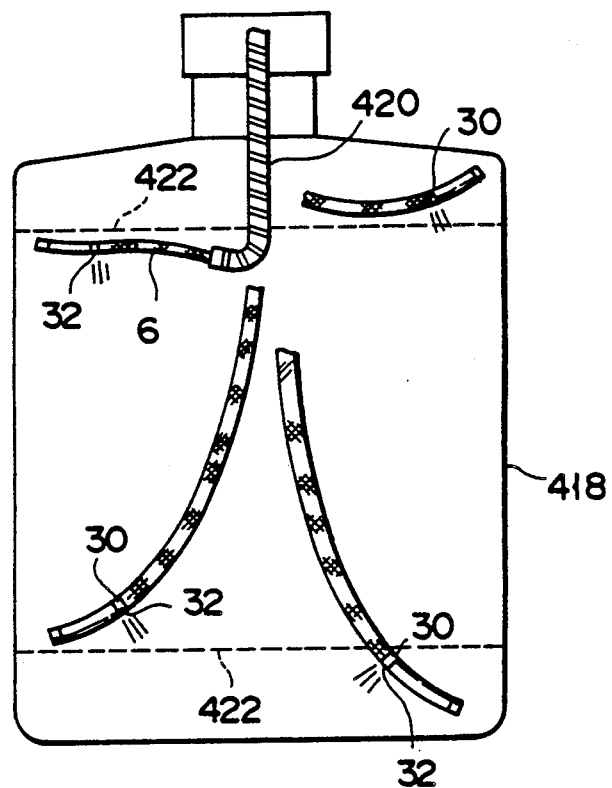
FIGS. 114 to 119 are side views for explaining the eleventh embodiment of the borescope.

In case if it is necessary to cause insertion unit 6 to be floated up after insertion of insertion unit 6 into the inner space of subject 418 of observation in order to observe an intended plate, e.g., welding line 422 on the inner surface of observation subject as shown in FIG. 114, insertion unit 6 is floated up to a desired state by jetting fluid, e.g., air, from jet port 32. That is, the drive mechanism is operated by operating knob 20 on operation unit 4 to transmit torque to the gear mechanism at the distal end via transmission wire 408. This torque is transmitted through drive small gear 406 and a pair of small gears 402A and 402B of the gear mechanism to rotate jet port member 30 according to the number of transmitted rotations. Thus, jet port member 30 is rotated about the axis of insertion unit 6 to change the orientation of jet port 32. Since the orientation of jet port 32 thus can be selected under remote control by operating operation unit 4 at hand, it is possible to select the orientation of jet port 32 according to a desired floating state. The operation is started after selecting the intensity or rate of jetting by operating operation switch 34 of operation unit 4 by taking the floating height as well into considerations. Regulator controller 392 controls air regulator 390 of high pressure fluid supply unit 132 to supply high pressure air from compressor 64 to endoscope 2. High pressure air is supplied through passage 110A in endoscope 2 to sealed space 41 inside jet port member 30 to be jet from jet port 32 of jet port member 30. Since the orientation of jet port 32 is preset to be downwards, insertion unit 6 is floated according to the intensity of jet. When the floating position and direction of insertion unit 6 are different from those required, adjustment like the step described above is done during the inserting operation to change the orientation of jet port 32 and rate of jetting so as to guide insertion unit 6 to a desired floating state. During this time, the orientation of distal end 14 can be changed with reference to the guide position by curving flexible end portion 12.

Figure 115:
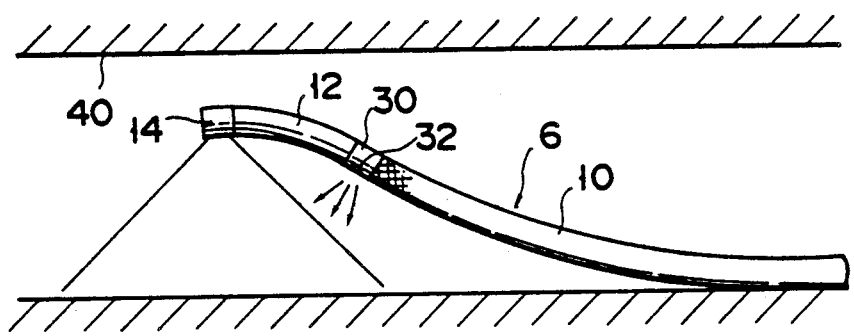
Figure 116:
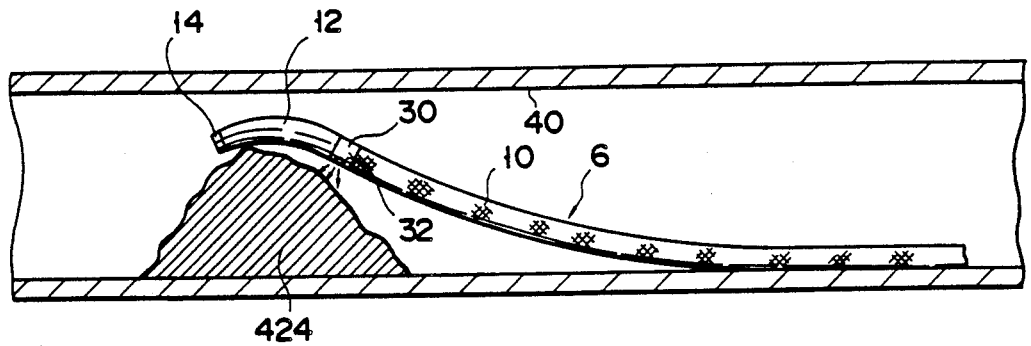
Figure 117:
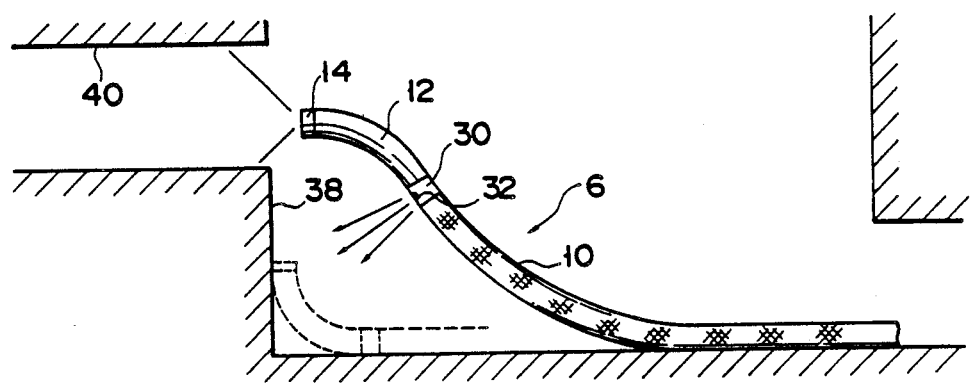
Figure 118:
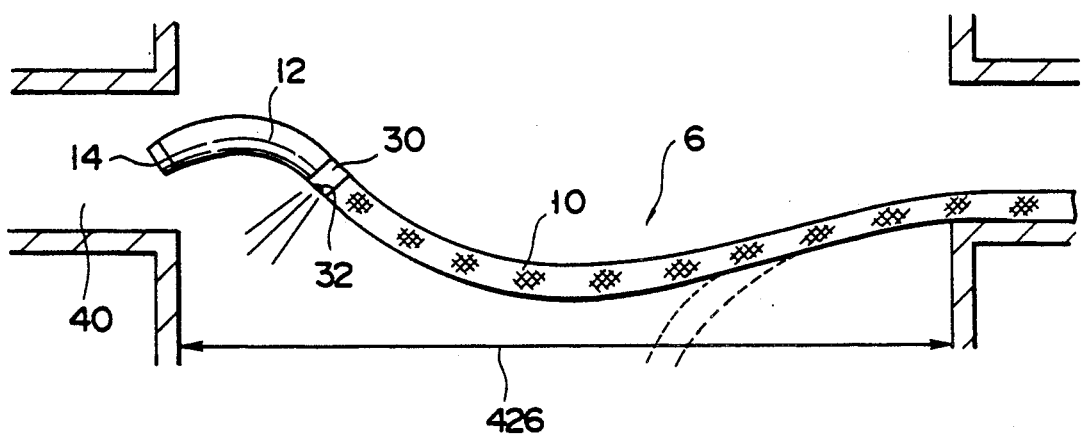
Figure 119:
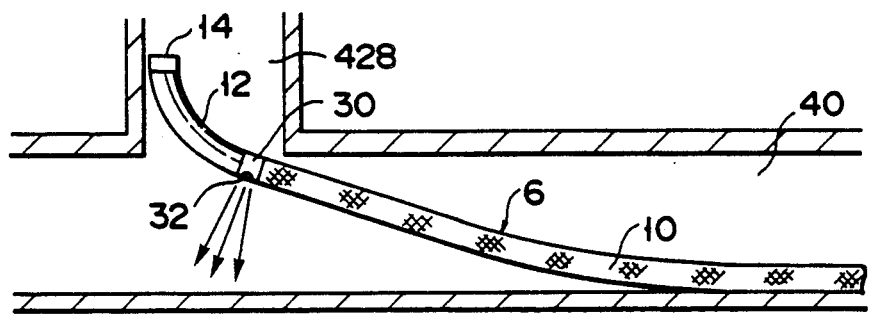

Further, when inspecting the inside of piping 40 as shown in FIG. 115, the rate of jetting or pressure is controlled with jet port 32 directed downwards to let end structure 14 of insertion unit 6 flow float near the center of the inside of piping 40 at all time. Endoscope 2 is of side-viewing type.

Where there is obstacle 424 in piping 40 under inspection as shown in FIG. 116, insertion unit 6 is floated with jet port 32 directed downwards, whereby insertion unit 6 can be inserted beyond the top of obstacle 424. In this case, the obstacle can be cleared without twisting operation unit 4 or insertion unit 6 of endoscope 2.

Where there is stepped wall 38 inside piping 40 under inspection as shown in FIG. 117, insertion unit 6 can be guided to be above stepped wall 38 by causing the floating of insertion unit 6 with jet port 32 directed downwards. Where there is large groove 426 inside piping 40 under inspection as shown in FIG. 118, groove 426 may be cleared by inserting insertion unit 6 in a floating state with jet port 32 directed downwards.

Where the inside of piping 40 has branching piping 428 branching upwards as shown in FIG. 119, it is possible to insert insertion unit 6 into branching piping 428 by causing the floating of insertion unit 6 with jet port 32 directed downwards and upwardly curving flexible end portion 12 with a large radius of curvature.

Figure 120:
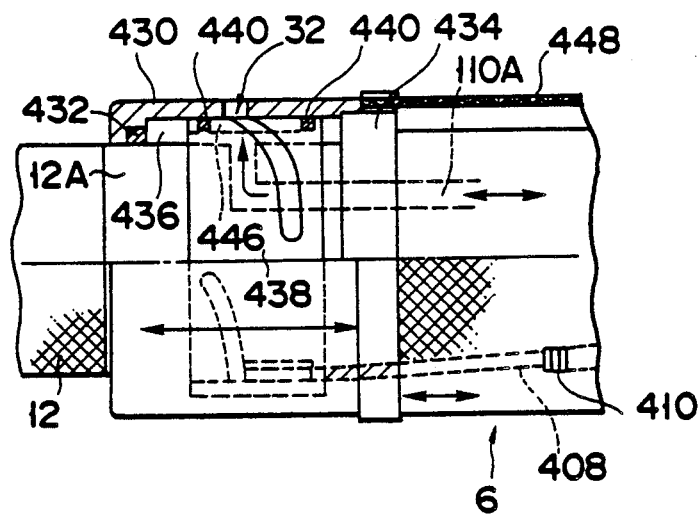
FIG. 120 is a side view showing a drive mechanism in a first modification of the eleventh embodiment of the borescope.
Figure 121:
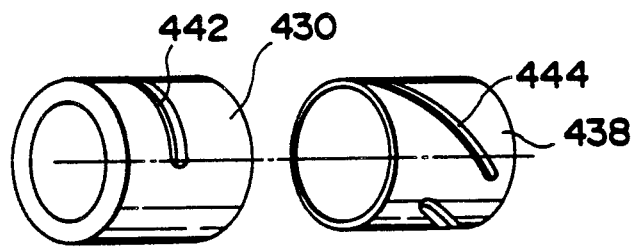
FIG. 121 is a perspective view showing an outer tube of the drive mechanism.
Figure 122:
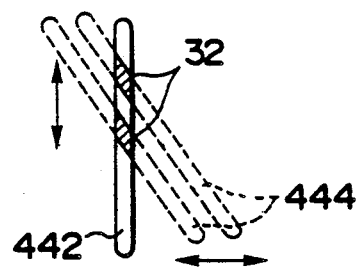
FIG. 122 is a diagram showing grooves of the drive mechanism.

FIGS. 120 to 122 show a first modification of the eleventh embodiment of the invention. This modification concerns the mechanism of moving the position of jet port 32 in the circumferential direction. As is shown, outer ring 430 is fitted on the outer periphery of stem 12A of flexible end portion 12 of insertion unit 6. It is mounted hermetically on the outer periphery of stem 12A. Elastic ring 432 is provided between the inner periphery of the front end of outer ring 430 and the outer periphery of stem 12A. Outer ring 430 has its stem hermetically mounted on large diameter portion 434. Between the inner periphery of outer ring 430 and outer periphery of stem 12A there is formed circumferential groove 436 isolated from the atmosphere. Cylindrical inner ring 438 is fitted in circumferential groove 436 for sliding in the axial direction of insertion unit 6. Sealing elastic ring 440 is mounted on the outer periphery of each end of inner ring 438 such that it is in frictional contact with the inner periphery of outer ring 430.

As shown in FIG. 121, outer ring 430 has jet groove 442 covering substantially one-third of the circumference. Inner ring 438 has spiral groove 444 extending at an angle to the circumferential direction. Jet groove 442 of outer ring 430 and spiral groove 444 of inner ring 438 intersect at one position as shown in FIG. 122, the intersection constituting jet port 32. Jet port 32 communicates with space 446 formed inside inner ring 438. Space 446 communicates with circumferential groove 416. As shown in FIG. 122, by moving inner ring 438 forwards and rearwards, the position of jet port 32 formed as the intersection of jet groove 442 of outer ring 30 and spiral groove 444 of inner ring 438 is moved in the circumferential direction.

Operating wire 408 is coupled to inner ring 438 as shown in FIG. 120, and by pulling operating wire 408 inner ring 438 can be moved in the axial direction of insertion unit 6. Operating wire 408 is guided by guide tube 410 extending through insertion unit 6 and coupled to a push/pull drive mechanism (not shown) provided in operation unit 4. This drive mechanism can be operated by knob provided on operation unit 4 to set a push-/pull extent transmitted to operating wire 4. Thus, the position of jet port 32 in the circumferential direction can be changed under remote control by operating a knob on operation unit 4 of endoscope 2.

Passage 110A for supplying high pressure fluid is connected to space 446 or circumferential groove 436 of outer ring 430 in communication with jet port 32. Passage 110A, as in the eleventh embodiment, is led through insertion unit 6, operation unit 4 and universal cord 8 of endoscope 2 to be connected to high pressure fluid terminal 382 of connector 16. High pressure fluid supply unit 132 outside the endoscope is connected to high pressure fluid terminal 382.

In this modification, by pushing or pulling operating wire 408 by operating the push/pull drive mechanism inside operation unit 4 of endoscope 2 with operating knob 412 on operation unit 4, inner ring 438 is moved with respect to outer ring 430 to cause a circumferential displacement of the position of jet port 32 constituted by the intersection between jet groove 442 and spiral groove 444.

Thus, as in the embodiment of FIG. 11, the floating and floating state of insertion unit 6 can be freely controlled by changing the position of jetting of high pressure fluid supplied form passage 110A.

In this first modification, protective outer blade 448 is detachably fitted on the outer periphery of flexible tube portion 10. Such protective outer blade 448 may be applied to other embodiments of endoscope.

Figure 123:
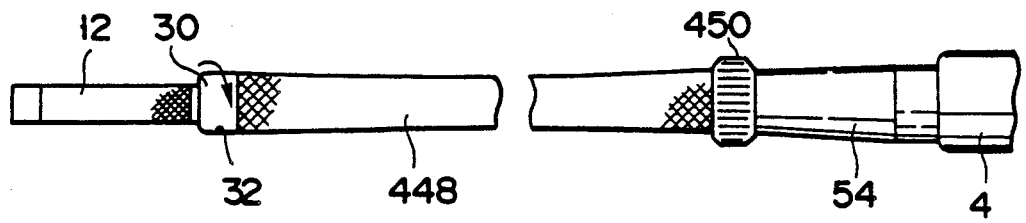
FIGS. 123 to 125 are respectively a side view, a fragmentary sectional view and a transversal sectional view showing an insertion unit in a second modification of the eleventh embodiment.
Figure 124:
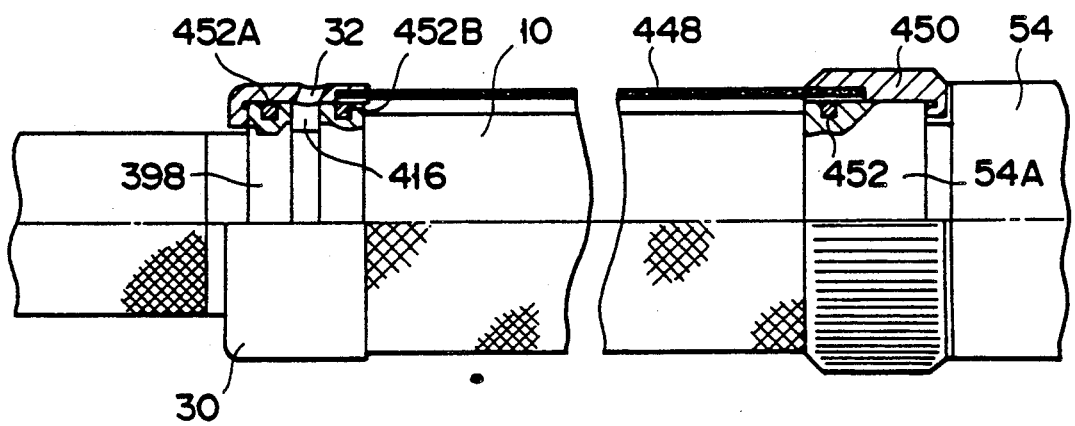
Figure 125:
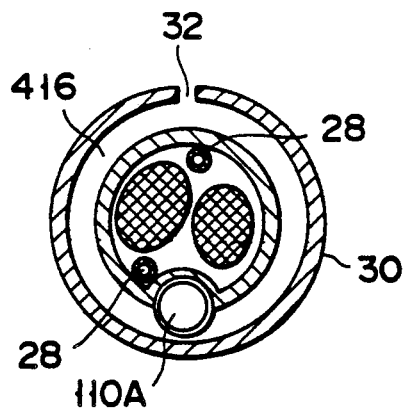

FIGS. 123 to 125 show a second modification. In this instance, like the embodiment of FIG. 11, jet port member 30 with jet port 32 is rotatably mounted on member 398 provided at stem of flexible end portion 12. An end of outer blade 448 fitted on the outer periphery of flexible tube portion 10 is coupled to jet port member 30, and jet port member 30 can be turned with flexible outer blade 448. The stem of outer blade 448 is coupled to operating ring 450 provided in the neighborhood of an end of stop member 54 provided on operation unit 4. Operating ring 450 is rotatably mounted on the outer periphery of end portion 54A of stop member 54. Gas-tight bearing 452 is provided on the outer periphery of end portion 54A. Thus, jet port member 30 can be turned via outer blade 448 by turning operating ring 450 at the stem of endoscope 2. Member 398, on which jet port member 30 is mounted, has its outer periphery formed with circumferential groove 416, and gas-tight bearings 452A and 452B are provided on member 398 on opposite sides of circumferential groove 416. Thus, jet port 32 is in communication with circumferential groove 416 at all time even when jet port member 30 is rotated. Passage 110A, to which high pressure fluid is supplied, communicates with circumferential groove 416. Passage 110A is led through insertion unit 6, operation unit 4 and universal cord 8 of endoscope 2 to be connected to high pressure fluid terminal 382 of connector 16, and high pressure fluid supply unit 132 provided outside the endoscope is connected to high pressure fluid terminal 382.

Thus, in this modification again, by turning operation ring 450 in operation unit 4 of endoscope 2, the torque is transmitted through outer blade 44 to jet port member 30, thus rotating jet port member 30 according to the rotation of operation ring 450. Thus, it is possible to move the position of jet port 32 of jet port member 30 in the circumferential direction.

Figure 126:
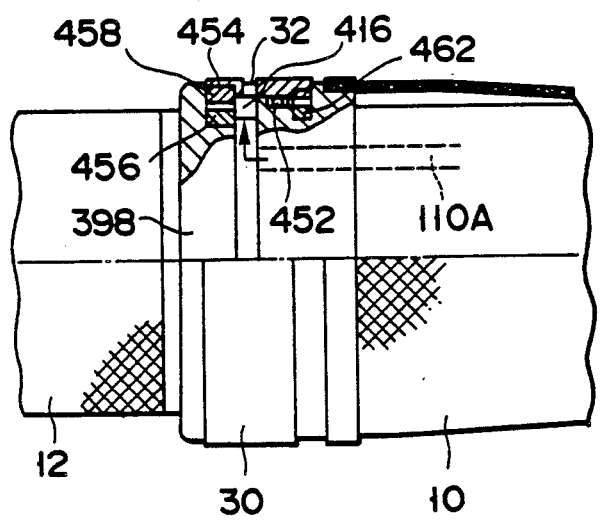
FIG. 126 is a fragmentary sectional view showing in insertion unit in a third modification.
Figure 127:
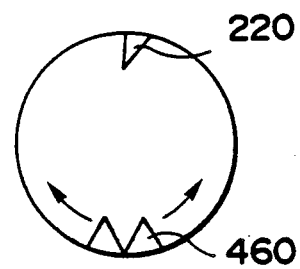
FIG. 127 is a schematic view showing an observation field of the third modification.

FIGS. 126 and 127 show a third modification. In this instance, like the second modification, jet port member 30 with jet port 32 is rotatably mounted on member 398 provided at the stem of flexible end portion 12. Circumferential groove 416 in communication with passage 110A is communicated with jet port 32. Jet port member 30 is supported by gas-tight bearing 425. Ring-like ultrasonic motor 454 is provided near the front end of jet port member 30. It consists of stator 456 and rotor 458, stator 456 being secured to member 398 and rotor 458 being coupled to jet port member 30. A drive signal line (not shown) is connected to ultrasonic motor 454, and it is connected to a drive power source (not shown) provided at the stem of endoscope 2 through insertion unit 6. An operation switch for controlling the drive power source is provided on operation unit 4 of endoscope 2. By operating operation switch, a controller controls the drive power source to drive ultrasonic motor 454 so as to rotate jet port member 30. The direction and extent of rotation of jet port member 30 are controlled to select the position of jet port 32. It is thus possible to move the position of jet port 32 of jet port member 30 in the circumferential direction.

In this embodiment of endoscope 2, as shown in FIG. 127, mark 460 consisting of a LED or liquid crystal indicating the direction of jet is provided in the field. Encoder 462 which detects the rotational position of jet port member 30 detects the orientation of jet port 32 and provides a detected orientation signal to objective lens section 18 of endoscope 2 to cause a movement of mark 460 according to the jetting direction. Further, the observation field is provided with mark 220 indicating the upward direction. Thus, the direction of jetting of fluid can be recognized while observing the field. Further, the direction of jetting of fluid can be displayed as observation image on the screen of TV monitor 78.

Figure 128:
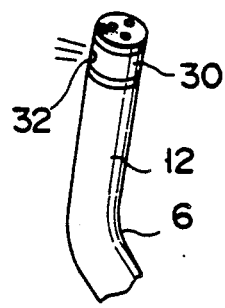
FIGS. 128 to 131 are perspective views and a sectional view showing different modifications of the insertion unit of the eleventh embodiment.

FIG. 128 shows a modification, in which end structure 14 of endoscope 2 is provided with jet port member 30 with jet port 32.

Figure 129:
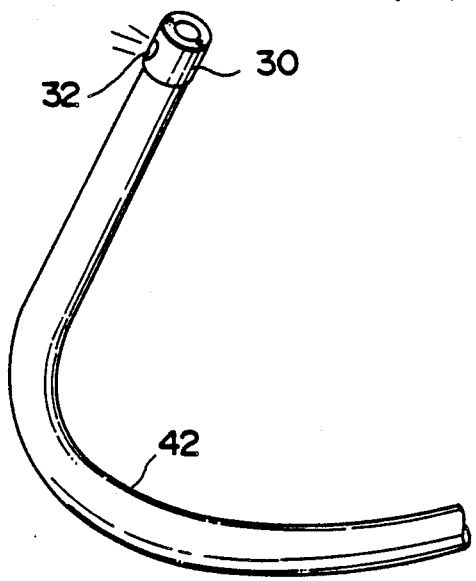

FIG. 129 shows a modification, in which guide tube 42 for guiding the insertion of endoscope has its end provided with jet port member 30 with jet port 32.

Figure 130:
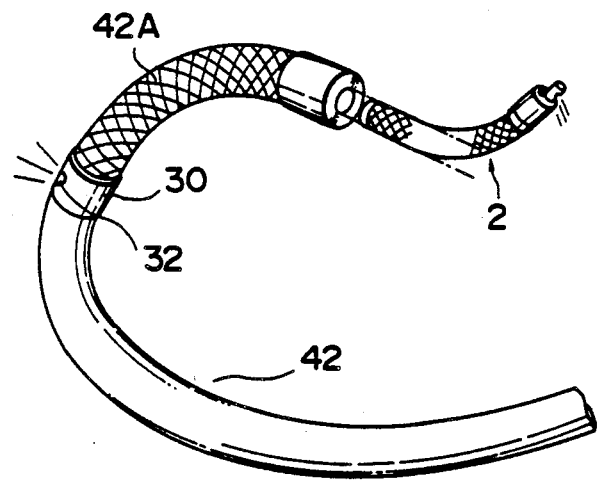

FIG. 130 shows guide tube 42 for guiding the insertion of the endoscope. Guide tube 42 has flexible end portion 42A, and jet port member 30 with jet port 32 is provided at the stem of flexible end portion 42A.

Figure 131:
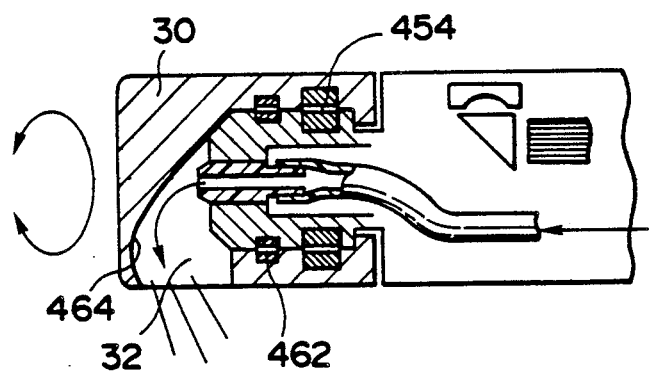

FIG. 131 shows a modification, in which jet port member 30 with jet port 32 is rotatably mounted on the end of side-viewing endoscope 2. Jet port member 30 is driven by ultrasonic motor 454, and the rotational position of ultrasonic motor 454 is detected by encoder 462. The orientation of jet port 32 can be indicated by moving mark 460 in the observation field of objective lens section 60. Further, in this modification jet port member 30 is provided with wind direction control member 464 to direct fluid toward jet port 32.

Figure 132:
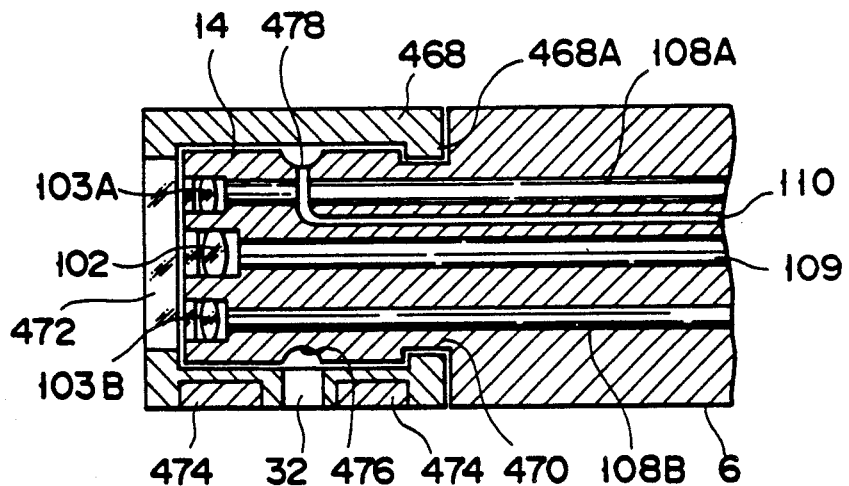
FIG. 132 is a sectional view showing an insertion unit of a twelfth embodiment of the borescope according to the invention.
Figure 133:
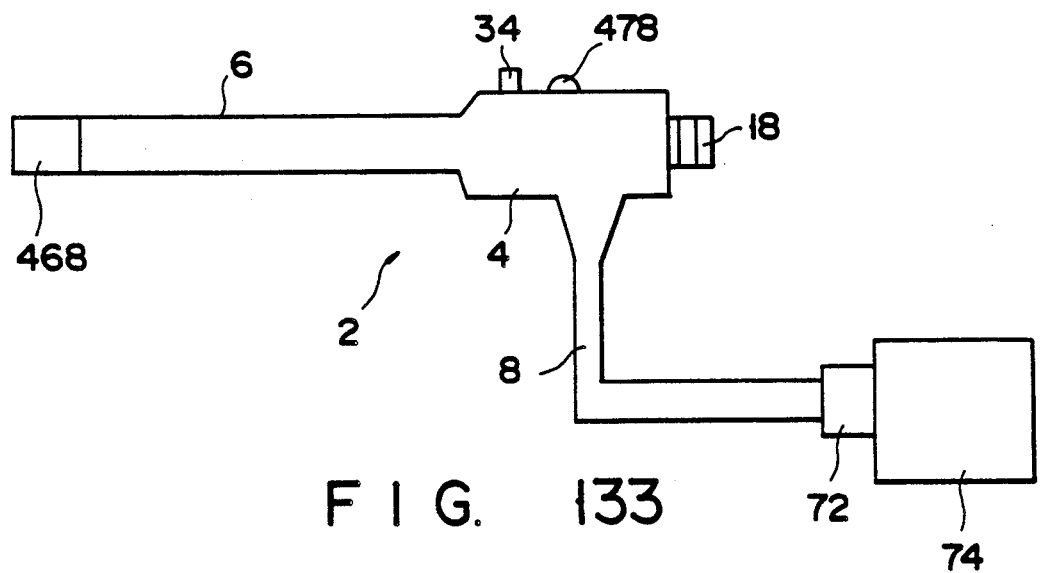
FIGS. 133 and 134 are schematic side views showing the twelfth embodiment of the borescope.

FIGS. 132 to 137 show a twelfth embodiment of the invention. FIG. 133 shows this embodiment of endoscope 2 and light source unit 74. Endoscope 2 has operation unit 4. Elongate flexible insertion unit 6 and universal cord 8 are coupled to operation unit 4. Universal cord 8 has its end provided with connector 72 detachably coupled to light source unit 74.

End structure 14 of insertion unit 6, as shown in FIG. 132, includes objective lens system 102 for observation and two illumination lens systems 103A and 103B. Image guide fiber 109 is optically coupled to objective lens system 102. It is optically coupled to objective lens section 18 of operation unit 4. Illumination lens systems 103A and 103B are optically coupled to fiber lightguide 108, which is led through insertion unit 6, operation unit 4 and universal cord 8 to connector 72 and optically coupled to an illumination light source in light source unit 74 via connector 72.

As shown in FIG. 132, end structure 14 of insertion unit 6 is provided with rotational member 468 rotatable about the axis of insertion unit 6. Rotary member 468 is substantially cylindrical and fitted on the outer periphery of end structure 14 of insertion unit 6. The inner periphery of the stem of rotary member 468 is formed with inward flange 468A. Flange 468A is fitted in annular groove 470 formed in the outer periphery of end structure 14 and supported to permit rotation of rotational member 468 while blocking forward or rearward movement. Light-transmitting cover 472 is mounted on the end of rotary member 468. Cover 472 covers the front surfaces of objective lens system 102 and two illumination lens systems 103A and 103B.

Weight 474 is hurried in a portion of the side surface of rotary member 468. With the provision of weight 474, the center of gravity of member 468 is deviated form the center of rotation. That is, rotary member 468 is automatically rotated due to the centroil deviation to a position, at which the centroid is on the lower side. Rotary member 468 has jet port 32 provided on a centroil side periphery portion. Thus, rotary member 468 is automatically rotated by the action of weight 474 to a position, at which weight 474 is on the lower side, whereby jet port 32 is automatically directed downwards.

The outer periphery of end structure 14 has annular groove 476 corresponding to jet port 32. Thus, jet port 32 is in communication with annular groove 476 irrespective of the rotational position of rotary member 468. Further, end structure 14 has supply port 478 in communication with circumferential groove 476. Tube 110 for supplying high pressure fluid is communicated with supply port 478. Tube 110 is led through insertion unit 6, operation unit 4 and universal cord 8 to connector 72 and connected to a reservoir tank and a pump of a high pressure fluid source provided in light source unit 74 via connector 72. On the supply passage, a variable throttle valve for controlling the supply pressure or rate of supply is provided, thus permitting the control of supply pressure or rate of supply. Alternatively, the pump output may be varied.

The supply rate and pressure of high pressure fluid supplied by high pressure fluid supply unit are controlled by control means. More specifically, operation unit 4 includes operation switch 34 and flow control switch 479, and each operation signal is led through a signal line (not shown) extending through universal cord 8 to a control circuit provided in light source unit 74. The control circuit controls the high pressure fluid supply unit pump output or variable throttle valve according to an instruction signal.

Now, the function of this embodiment of endoscope 2 will be described. Insertion unit 6 is gradually inserted into a piping while observing the observation field of the endoscope. At this time, rotary member 468 provided on end structure 14 of insertion unit 6 is held with its lower portion with weight 474 directed downwards due to weight 474. That is, rotary member 468 is automatically rotated to bring the weight to the lower side due to deviation in centroid. Since rotary member 468 has jet port 32 formed in the periphery on the side of the weight, jet port 32 is held such that it is directed downwards.

Figure 134:
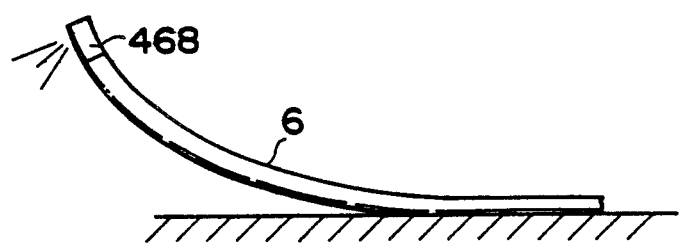
Figure 135:
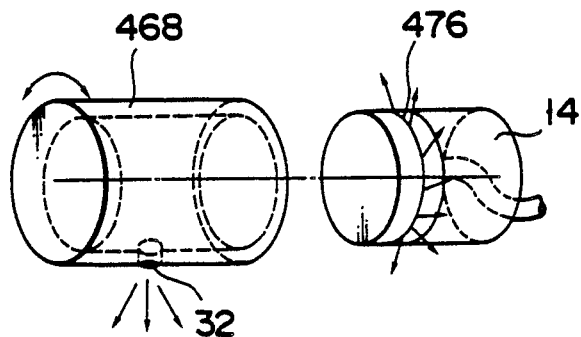
FIGS. 135 to 137 are respectively a perspective view, a transversal sectional view and a longitudinal sectional view showing an end structure of an insertion unit.
Figure 136:
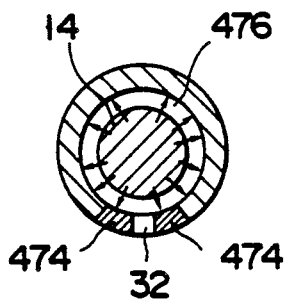
Figure 137:
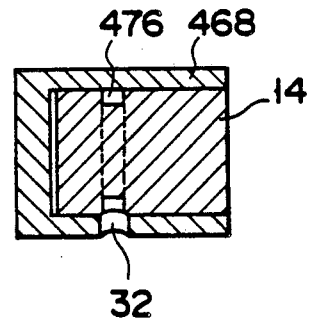

Jet port 32 communicates with the annular groove 476 of flexible end portion wherever it is located. Annular groove 476 is connected to the pump of the high-pressure fluid source incorporated within light source unit 74 by means of supply port 478 and tube 110. Therefore, when the pump is driven, a high-pressure fluid, e.g., air, is jetted from jet port 32. Due to the reaction of the high-pressure fluid, the distal end portion of insertion unit 6 is bent upward as is shown in FIG. 134. As a result, end structure 14 is turned up. Thus, the friction between insertion unit 6 and the bottom is reduced, whereby unit 6 can be easily inserted deeper into a duct.

The level to which end structure 14 is raised can be controlled by operating flowrate-adjusting switch 479. When structure 14 is raised to a predetermined level by operating switch 479, insertion unit 6 can be moved forward over a stepped portion or a bending portion, if any.

In most cases, jet port 32 faces downward while insertion unit 6 is being inserted deeper into a body cavity. Hence, it is unnecessary to made several jet ports in unit 6, spaced apart from one another in the circumferential direction of unit 6 so that the high-pressure fluid is jetted through the port which happens to face downward. Even if insertion unit 6 is twisted or bent at several portions, jet port 32 is automatically moved to face downward. Hence, in order to raise insertion unit 6, it suffices to jet the high-pressure fluid through port 32. The endoscope apparatus according to the present invention has great operability. In other words, with this apparatus it is easy to bend the insertion unit while guiding it deeper to a desired position in a duct.

Figure 138:
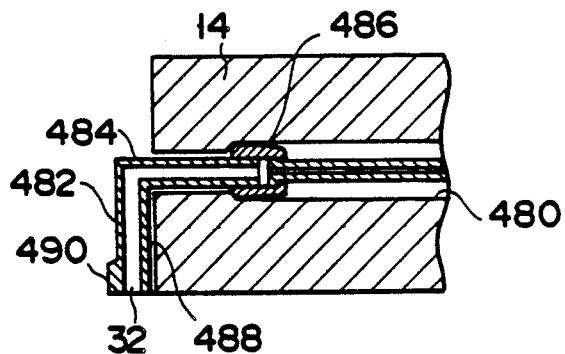
FIG. 138 is a longitudinal sectional view showing an end structure of an insertion unit in a first embodiment of the twelfth embodiment.

FIG. 138 shows a first modification of the twelfth embodiment of the present invention. As is shown in this figure, channel 480 is formed in insertion unit 6. Channel 480 extends in the axial direction of unit 6 and opens at the forward end of end structure 14. Pipe 484 is inserted in channel 480, and its proximal end is connected to a compressor (not shown in FIG. 138).

Nozzle 482 is attached to the distal end of pipe 484. More precisely, rotary ring 486 is attached to the distal end of pipe 484, and nozzle 482 is in screw engagement with this ring 486. Hence, nozzle 482 can be rotated freely and can also be detached from ring 486. As is shown in FIG. 138, the distal end portion 488 of nozzle 482 is bend at right angles to the remaining portion which is coaxial with pipe 484. Distal end portion 488 has jet port 32 in its tip. Weight 490 is attached to the tip of distal end portion 488. Due to weight 490, jet port 32 always extends vertically whenever end structure 14 is rotated through any angle. The modification provided with end structure 14 shown in FIG. 138 has, therefore, the same advantages as the twelfth embodiment.

Figure 139:
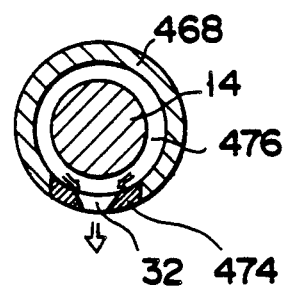
FIG. 139 is a transveresal sectional view showing an end structure of an insertion unit in a second modification of the twelfth embodiment.

FIG. 139 shows a second modification of the twelfth embodiment of the present invention. As is shown in this figure, jet port 32 has a converging cross section. Since port 32 is so shaped, the direction in which the high-pressure fluid is jetted can be changed by rotating rotary member 468. To change this direction, it suffices to stop the jetting of the fluid for some time, thus allowing rotary member 468 to rotated by its own weight.

FIGS. 140, 141 and 142 illustrate a third modification of the twelfth embodiment. The third modification is characterized in two respects. First, bending portion 12 is connected to the distal end of flexible tube 10. Secondly, end structure 14 having rotary member 468 is attached to the distal end of flexible end portion 12.

Figure 143:
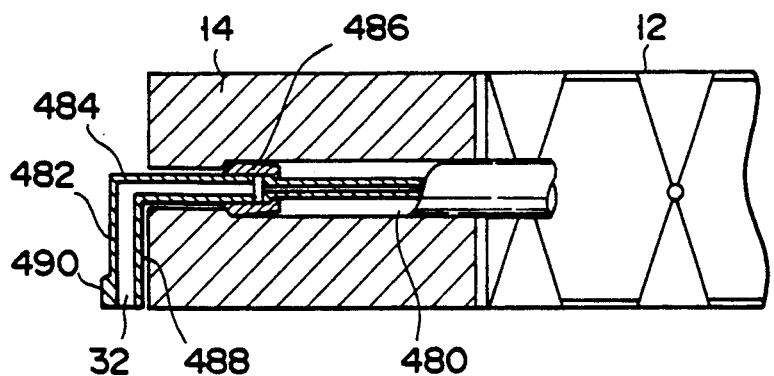
FIG. 143 is a schematic longitudinal view showing an insertion unit in a fourth modification.

FIG. 143 shows a forth modification of the twelfth embodiment. This modification is characterized in two respects. First, bending portion 12 is connected to the distal end of flexible tube 10. Secondly, end structure 14 having rotatable nozzle 482 is attached to the distal end of bending portion 12.

Figure 144:
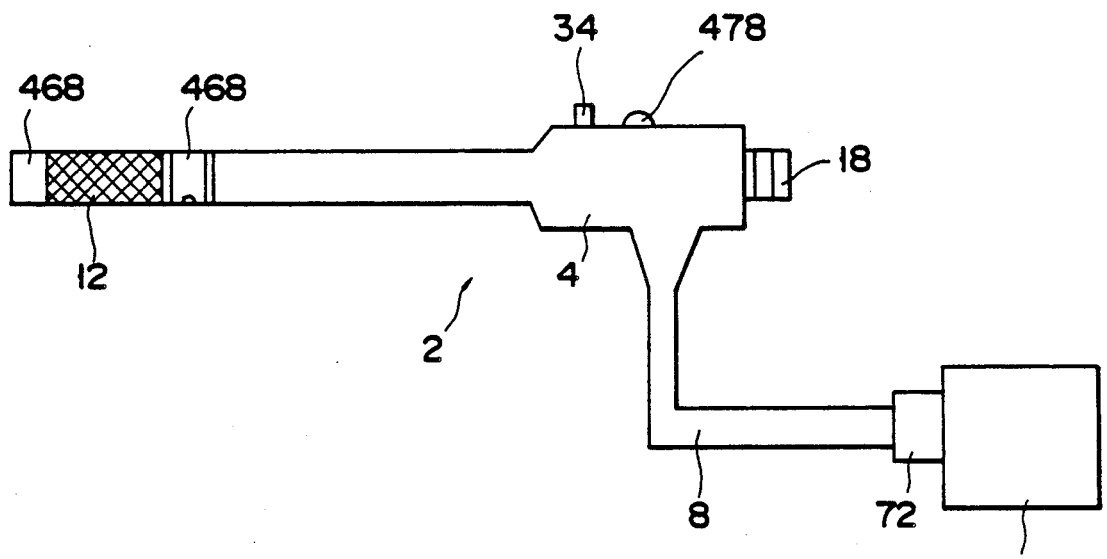
FIG. 144 is a schematic side view showing a fifth modification of the borescope.
Figure 145:
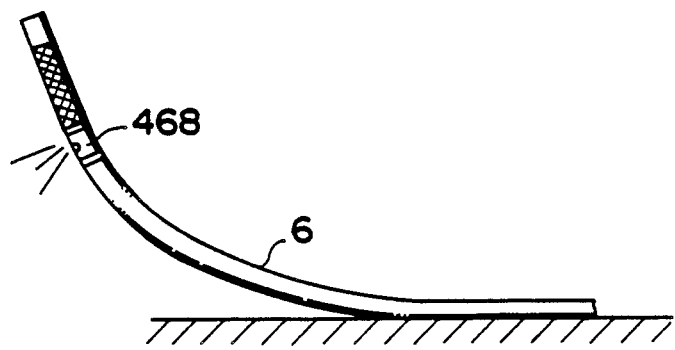
FIGS. 145 and 146 are respectively a side view and a longitudinal sectional view showing an insertion unit of the fifth modification.
Figure 146:
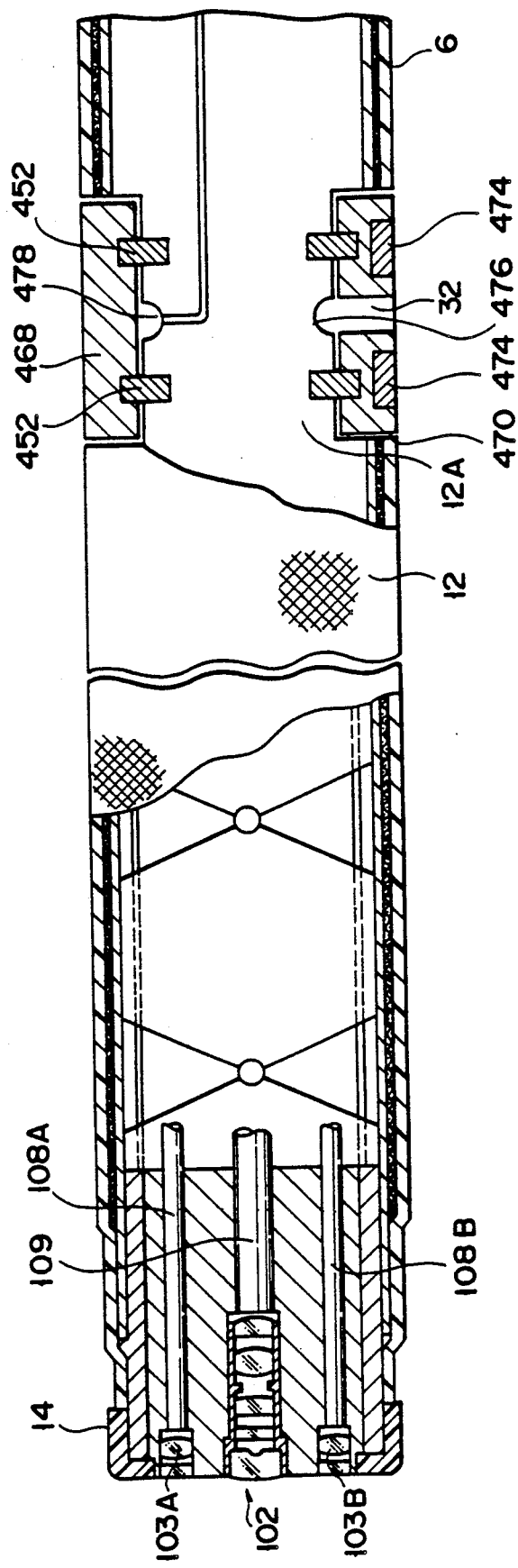

FIGS. 144, 145 and 146 illustrate a fifth modification of the twelfth embodiment of the present invention. The fifth modification is characterized in two respects. First, flexible end portion 12 is connected to the distal end of flexible tube 10. Secondly, rotary member 468 is attached to the proximal end of flexible end portion 12.

The second modification (FIG. 139), the third modification (FIGS. 140 to 142), the fourth modification (FIG. 143), and the fifth modification (FIGS. 144 to 146) have the same advantage as the twelfth embodiment in that rotary member 468 is always positioned with its opening facing downward.

Figure 147:
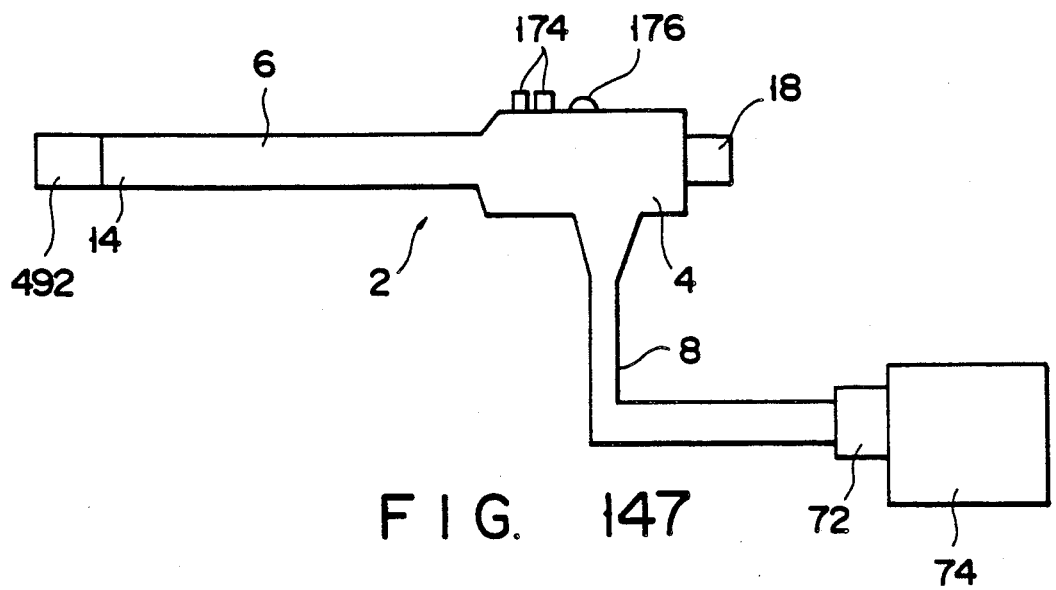
FIG. 147 is a schematic view showing a thirteenth embodiment of the borescope according to the invention.

FIGS. 147 to 150 show a thirteenth embodiment of the present invention. FIG. 147 illustrates endoscope 2 and light source unit 74. Endoscope 2 is provided with operation unit 4. Insertion unit 6, which is long and flexible, and universal cord 8 are connected to operation unit 4. Unit 6 has end structure 14. Plug 72, which is detachably coupled to light source unit 74, is fastened to the distal end of universal cord 8.

Figure 148:
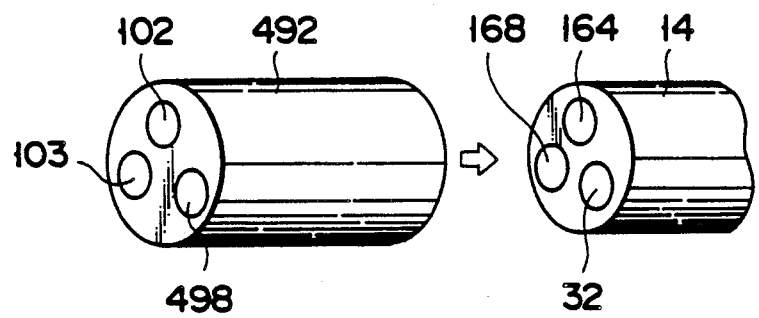
FIG. 148 is a perspective view showing an end of an borescope and an adopter.

As is shown in FIG. 148, observation window 164, illumination window 168, and jet port 32 are provided at the distal end of end structure 14. Jet port 32 is a hole made in the distal end of structure 14. Thus, this endoscope 2 is of a so-called "direct-view type." Observation window 164 is optically connected to the eyepiece lens system of eyepiece unit 18 incorporated in operation unit 4 by means of an objective lens system (not shown) and an image guide (not shown, either). Illumination window 168 is optically connected to a light guide (not shown). The light guide extends through insertion unit 6, operation unit 4, and universal cord 8, and is coupled to plug 72. Thus, the light guide is optically coupled to the illumination light source provided within light source unit 74.

As is illustrated in FIGS. 148 to 151, various adapters 492, 494 and 496 can be detachably connected to end structure 14 of insertion unit 6. Adapter 492 shown in FIG. 147 has objective lens system 102 and illumination system 103. System 102 is optically coupled to observation window 164, whereas illumination system 103 is optically coupled to illumination window 168. Adapter 492 also has jet port 498 which communicates with jet port 32 and extends forward. Thus, when this adapter 492 is attached to end structure 14, the endoscope will function as a direct-view type one, and a fluid can be jetted forward through jet port 498.

Figure 149:
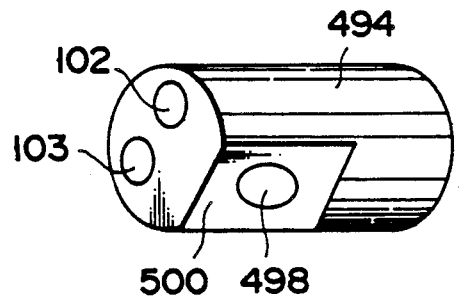
FIGS. 149 and 151 are perspective views showing other adopters.

Adapter 294 shown in FIG. 149 also has objective lens system 102 optically coupled to observation window 164, and illumination system 103 is optically coupled to illumination window 168. Adapter 494 also has jet port 498 which communicates with jet port 32 and opens in the lower surface 500. Hence, when adapter 294 is attached to end structure 14, the endoscope will function as a direct-view type one, and a fluid can be jetted downward through jet port 498.

Figure 151:
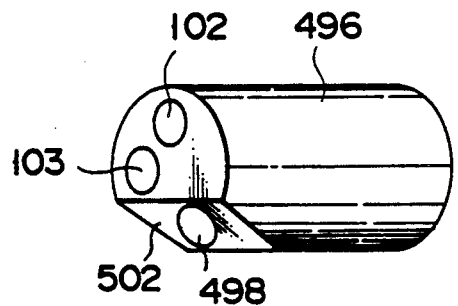

Adapter 496 illustrated in FIG. 151 also has objective lens system 102 optically coupled to observation window 164, and illumination system 103 is optically coupled to illumination window 168. Adapter 494 has a inclined, lower surface 502, and jet jet port 498 opening in this surface 502 and communicating with jet port 32. Therefore, when adapter 296 is attached to end structure 14, the endoscope will function as a direct-view type one, and a fluid can be jetted downward and forward through jet port 498.

The channel, which defines jet port 32 of insertion unit 6, communicates with plug 72 through unit 6, operation unit 4, and universal cord 8. In other words, plug 72 connects jet port with the compressor provided within light source unit 74. The fluid source has a motor-driven pump, which is connected in the fluid supply passage connecting the fluid tank and plug 72. A valve is also connected in this passage. Thus, the pressure and flow rate of the fluid can be changed by controlling the pump and by changing the opening of the valve. It is desirable that a reservoir be connected to the pump, thereby to moderate the pulsative changes in the output pressure of the pump.

As is illustrated in FIG. 147, operation unit 4 has fluid-jetting switch 174 and flow rate-adjusting switch 176. When either switch is operated, an electric signal is supplied to from the switch to the control circuit (not shown) incorporated in light source unit 74, via the signal line (not shown) which is contained in universal cord 8 and connects the switch to the control circuit. The control circuit controls the pump and the valve in accordance with the signals, thereby to adjust the pressure and flow rate at which the high-pressure fluid is supplied to jet port 32.

It will now be explained how endoscope 2 according to the thirteenth embodiment is operated. First, the operator gradually inserts insertion unit 6 into a duct, while looking at the view field of the endoscope. When adapter 492 (FIG. 148) is attached to unit 6, and the high-pressure fluid is jetted through jet port 498 of this adapter, the fluid is applied forward, thus removing dust from observation window 164. As a result, window 164 is cleaned, ensuring a good observation of the interior of the duct. In this case, to set end structure 14 in a different direction, it suffices to jet the high-pressure fluid through port 498 while facing adapter 492 downward, thereby bending the distal end portion of insertion unit 6 upward by virtue of the reaction of the fluid.

Figure 150:
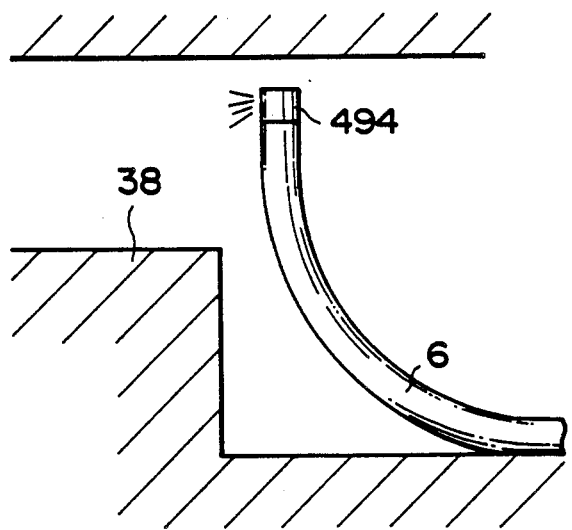
FIG. 150 is a side view showing an operating state of an insertion unit.

When adapter 494 shown in FIG. 149 is attached to insertion unit 6, and the high-pressure fluid is jetted via port 498 of this adapter, the fluid is applied downward. Due to the reaction of the fluid, the distal end portion of unit 6 is bent upward. When the fluid is jetted most strongly, the distal end portion of unit 6 will be bent as is shown in FIG. 150. If this case, the distal end portion of unit 6 reaches a level higher than stepped portion 38 existing in the duct. Therefore, insertion unit 6 can be inserted forward over stepped portion 38.

When adapter 496 shown in FIG. 151 is attached to insertion unit 6, and the high-pressure fluid is jetted via port 498 of this adapter, the fluid is applied downward and forward. The fluid can remove dust from observation window 164, and also its reaction bends the distal end portion of unit 6 upward. Hence, not only a good observation of the interior of the duct is achieved, but also insertion unit 6 can be inserted forward over a stepped portion which is not so high.

When the distal end portion of insertion unit 6 is raised away from the inner periphery of the duct by virtue of the reaction of the high-pressure fluid being jetted, the friction between unit 6 and the inner periphery of the duct is reduced. The decerase in this friction renders it easy for the operator to insert unit 6 deeper into the duct.

Figure 152:
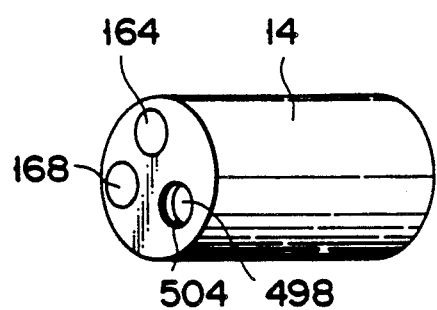
FIG. 152 is a perspective view showing an end structure of a first modification of the thirteenth embodiment.
Figure 153:
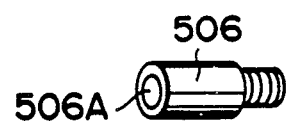
FIGS. 153 to 155 are perspective views and a sectional view showing various jet port members.
Figure 154:
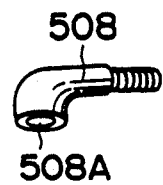

FIG. 152 illustrates a first modification of the thirteenth embodiment of the present invention. This modification is characterized in two respects. First, jet port 32 has threaded portion 504. Secondly, use is made of nozzles 506 and 508 of different structures, shown in FIGS. 153 and 154, respectively. As is shown in FIG. 153, nozzle 506 is straight, has jet port 506A facing forward. The proximal end of nozzle 506 is threaded and can be set in screw engagement with the threaded portion 504 of jet port 32. As is shown in FIG. 154, nozzle 508 is bent in the form of letter L, with its jet port 508A facing downward. The proximal end of nozzle 608 is threaded and can, thus, be set in screw engagement with the threaded portion 504 of jet port 32. Either Nozzle 506 or nozzle 508 is attached to end structure 14 of insertion unit 6 thereby to jet the high-pressure fluid forward or downward, in accordance with the condition in which endoscope 2 is used.

Either nozzle 506 (FIG. 153) or nozzle (FIG. 154) can be connected with jet port 498 of adapter 492, 494 or 496, not with the end structure 14 of insertion unit 6. If this is the case, jet port 498 is threaded so that nozzle 506 or 508 is fitted in this port 498.

Figure 155:
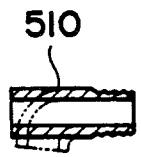

FIG. 155 shows a second modification of the thirteenth embodiment. This modification is characterized in that semiflexible nozzle 510 is used. Nozzle 510 has a distal end portion which is flexible, and a proximal end portion which is threaded. In use, the threaded portion of nozzle 510 is fitted in the jet port of adapter 492, 494 or 496. Since flexible portion of nozzle 510 can be bent plastically by the operator at any desired angle, the high-pressure fluid can be jetted in any desired direction through nozzle 510.

FIGS. 156 and 157 illustrate a third modification of the thirteenth embodiment. In the third modification, flexible end portion 12 is connected to the distal end of insertion unit 6, and adapter 494 is attached to the distal end of portion 14.

Figure 160:
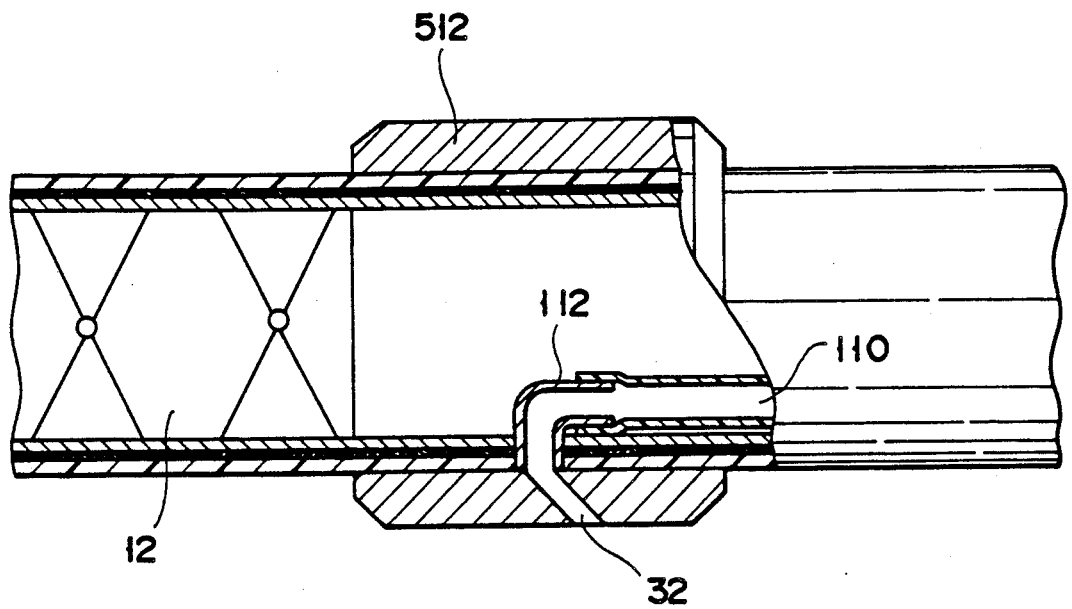
FIGS. 160 and 161 are sectional views showing an intermediate adopter in the third modification.
Figure 161:
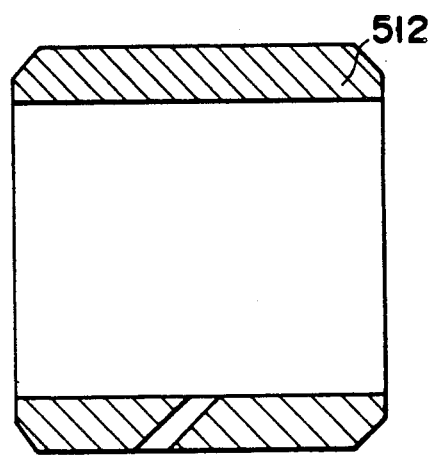

FIGS. 158 to 161 show a fourth modification of the thirteenth embodiment. As is shown in FIG. 158, flexible end portion 12 is coupled to the distal end of insertion unit 6, adapter 152 is connected between the proximal end of end portion 12 and the remaining portion of unit 6. As is shown in FIG. 161, adapter 512 is mounted on the outer periphery of insertion unit 6, and has jet port 32 communicating with connector tube 112 connected to air supply tube 110. Jet port 32 extends downward and rear-ward as shown in FIG. 160.

Figure 162:
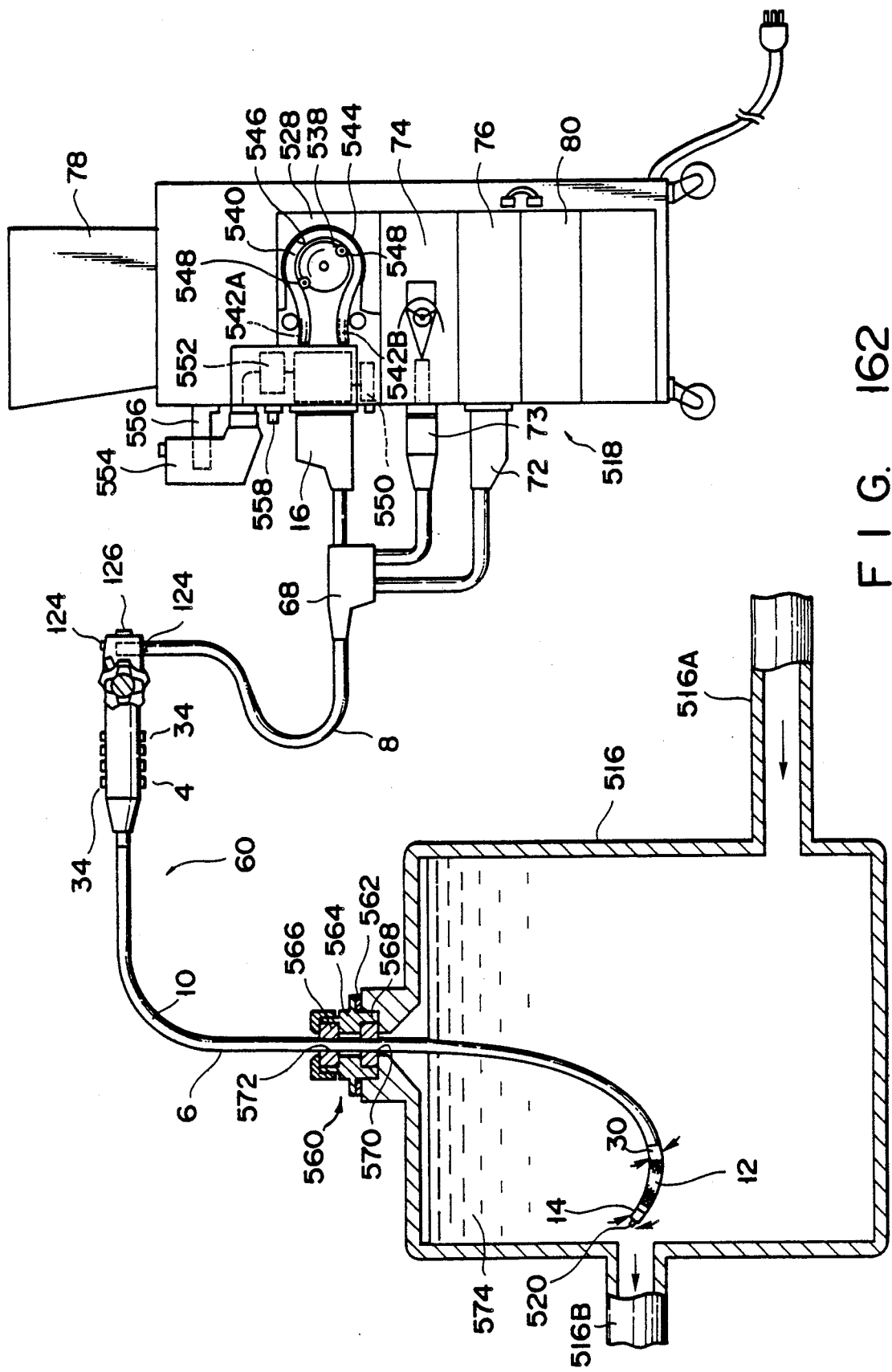
FIG. 162 is a side view showing a fourteenth embodiment of the borescope according to the invention.
Figure 163:
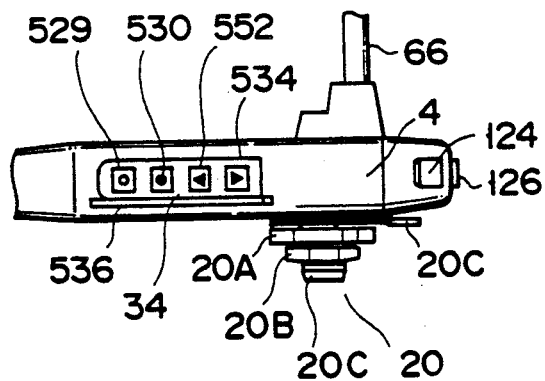
FIG. 163 is a plan view showing an operation unit of the fourteenth embodiment of the borescope.

FIGS. 162 to 165 illustrate a fourteenth embodiment of the present invention. FIG. 162 schematically shows the condition in which a system including so-called electronic endoscope 60 is used or operated. The endoscope system has device 518 which includes an electric system, a light source, and the like. Endoscope 60 comprises insertion unit 6, operation unit 4, and cable 66. Insertion section 6 consists of flexible tube 10, i.e., the proximal portion, flexible end portion 12 connected to tube 10, and end structure 14 connected to portion 12. As is shown in FIG. 163, operation section 20 is mounted on unit 4. Section 20 has knobs 20A, 20B and 20C. When knobs 20A and 20B are rotated, flexible end portion 12 is bent. When knob 20C is rotated to a first position, portion 12 is held in a bent state. When knob 20C is rotated to a second position, portion 2 will be released from the bent state. Connector 16 is connected to the distal end of cable 8. This connector is detachably coupled to device 518.

Figure 164:
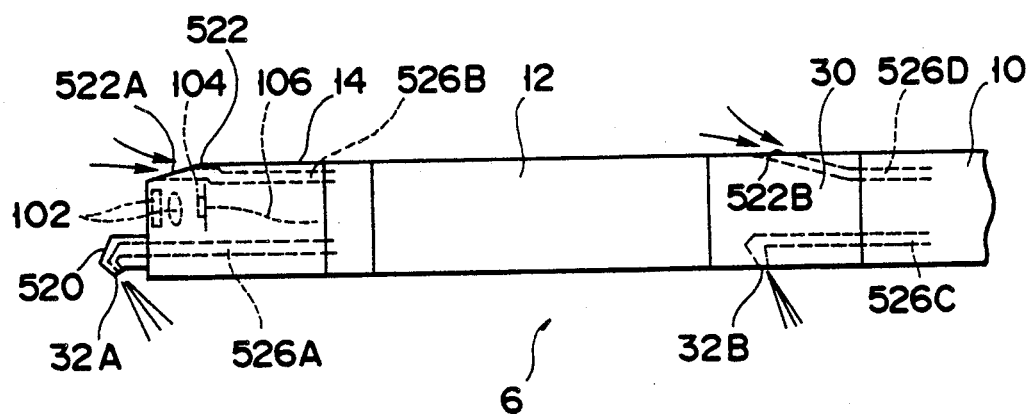
Figure 165:
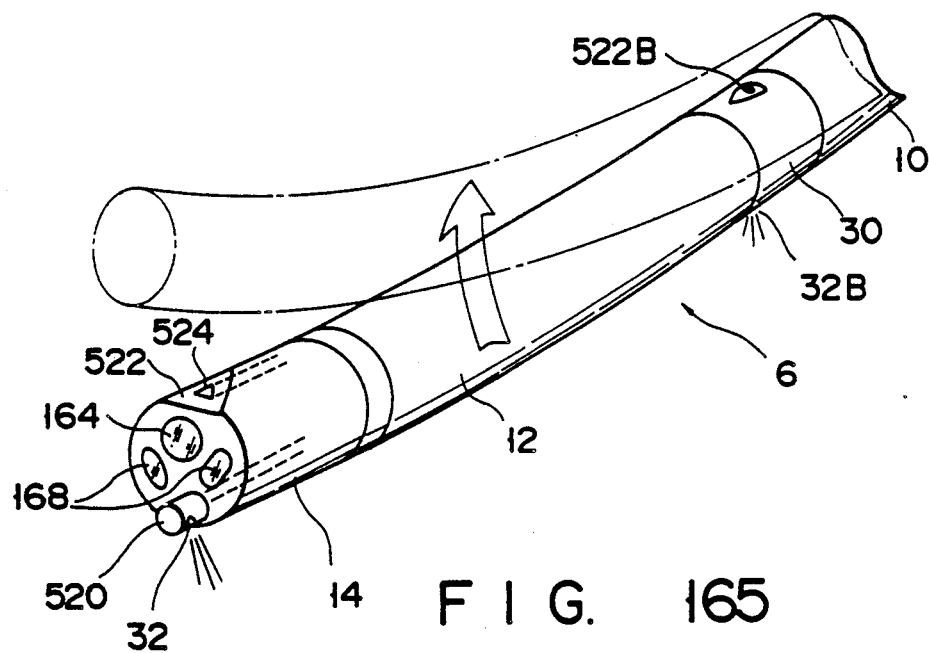

As is illustrated in FIG. 165, observation window 164 and two illumination windows 168 are provided on the distal end of end structure 14. Endoscope 60 is, therefore, a direct-view type one. Observation window 164 is located above both illumination windows 168. Illumination windows 168 are are spaced apart from each other in the horizontal direction. Nozzle 520 projects from the distal end of end structure 14 and is located below illumination windows 168. Nozzle 520 has jet port 32 which extends slantwise and rearward as is shown FIG. 164. End structure 14 has an inclined surface 522 at its distal end. Suction port 522A is cut in this surface 522 and opens upward. As is shown in FIG. 164, two channels 526A and 526B are connected to jet port 32A and suction port 522A, respectively. Both channels 526A and 526B extends through insertion unit 6, operation unit 4 and cable 8, and are connected to connector 16. They are coupled to rotary pump 528 incorporated device 518 when connector 16 is coupled to device 518.

Other jet port 32B and suction port 522B are formed in jet port member 30 which connects flexible end portion 12 to flexible tube 10 and opens at the lower portion of member 30. Jet port 32B extends slandwise and downward. Suction port 522B extends slandwise and upward and opens at the upper portion of member 30. Channels 526C and 256D, which are similar to channels 526A and 526B, are connected to jet port 32B and suction port 522B, respectively. These channels 526C and 526D extends through insertion unit 6, operation unit 4 and cable 8, and are connected to connector 16. They are coupled to another rotary pump (not shown) incorporated device 518 when connector 16 is coupled to device 518.

As is illustrated in FIG. 165, objective lens 102 and solid-state image sensor element 104 are provided within end structure 14. Both lens 102 and element 104 are located behind observation window 164. Image signal cord 106 extends through insertion unit 6, operation unit 4 and cable 8. It further exerted from branching portion 68 and is connected to plug 72. Thus, cord 106 is coupled to camera control unit 76 incorporated within device 518 when plug plug 72 is connected to device 518. VCR 80, TV monitor 78, and the like are also incorporated in device 518.

A light guide (not shown) is connected to illumination window 168 of end structure 14. This light guide extends through insertion unit 6, operation unit 4 and connector 66. The light guide further exerted from branching portion 68 and is connected to plug 72. Thus, it is coupled to light source unit 74 incorporated within device 518 when plug plug 72 is connected to device 518.

As is shown in FIG. 163, control switch section 34 is provided on one side of operation unit 4. Section 34 has suction button 529, start button 530, flow rate-reducing button 532, and flow rate-increasing increase button 534. These buttons 529, 530, 532 and 534 are arranged in a line, thus forming an array. Rib 536 extends parallel to this array, and function as a guard for preventing erroneous depression of the buttons. Buttons 529, 530, 532 and 534 can be replaced by flat buttons each of of which is seldom depressed along with any other. If flat buttons are used, rib 532 is unnecessary. Another control switch section (not shown), which is identical to the other section 34, is provided on the other side of operation unit 4. Hence, any person whether right-handed or left-handed, can easily operate operation unit 4. Further, operation unit 4 has freeze button 124 and release button 126, both are operated to photographing the interior of a duct.

As is shown in FIG. 162, rotary pump 528 comprises rotor 538 and flexible tube 540 looped around rotor 538. The ends of tube 540 are connected to connecting tubes 542A and 542B, which in turn are connected to channels 526A and 526B, respectively. The middle portion of flexible tube 540 contacts inner periphery 546 of base 544 which is concentric with rotor 538. Rotor 538 has a plurality of rollers 548 which contact the middle portion of flexible tube 540. When rotor 538 rotates in the direction of the arrow shown in FIG. 162, rollers 548 collapse tube 540, thereby supplying the fluid from channel 524A to channel 524B. Reservoir tank 550 is coupled at least one connecting tube, either tube 542A or 542B. Thus, the fluid can be stored in tank 550 in such an amount that no troubles occur in the endoscope system or the duct. The portion of the fluid stored in tank 550 can be extracted for analyzing its composition. cartridge tank 554 is connected at least one connecting tubes, either 542A or 542B, by means of electromagnetic valve 552. As is illustrated in FIG. 162, cartridge tank 554 is loosely held in tank holder 556 and positioned vertically. Tank 554 can be replaced by another in accordance with the use of the endoscope system. Electromagnetic valve 552 is opened when electromagnetic switch 558 is turned one, thus supplying the fluid from cartridge tank 554 to connecting tubes 542A and 542B.

Tank 516, which is being examined by means of the endoscope system, has opening 560. Cap 564 seals this opening 560, with assistance of packing 562. Cap 564 has two seals 566 and 568. Seals 566 and 568 have holes 570 and 572, respectively. These holes 570 and 572 connect tank 516 with insertion unit 6 of endoscope 60. Cap 564 can have more seals. The greater the difference between the pressures inside and outside tank 516, the more seals. Preferably, the seals have different hardnesses; each seal being harder than the immediately preceding or following one, with respect to the axis of tank 516.

It will now be explained how to use or operate endoscope 60. First, as is shown in FIG. 162, the operator connects connectors 16, plug 72, and plug 73 to device 518. Then, he or she inserts insertion unit 6 into tank 516 in airtight fashion, first through cap 564, then through first seal 566, and finally through second seal 568. Tank 516 contains, for example, gasoline 574. Since gasoline is a transparent liquid, the interior of tank 516 can be observed through endoscope 60.

In order to guide insertion unit 6 to the desired position within tank 516, the operator pushes start button 530 of control switch section 34, thereby starting rotary pump 528. As a result, the pressurized fluid is supplied to jet ports 32A and 32B through channels 526A and 526C, respectively. Simultaneously, the same amount of a fluid is sucked into suction ports 522A and 522B and supplied back into rotary pump 528 through channels 526B and 526D. Therefore, the fluid circulates in the loop consisting of pump 528, channel 526A and channel 526B, and also in the loope consisting of pump 528, channel 526C and channel 526D, as long as rotary pump 528 is driven. Hence the high-pressure fluid is jetted downward through jet ports 32A and 32B, whereby insertion unit 6 rises due to the reaction of the jets of the fluid. In the meantime, the pressure exerted on the upper portion of unit 6 is lower than the pressure exerted on the lower portion of unit 6, since the fluid is being sucked into unit 6 through suction ports 522A and 522B. This promote the rising of unit 6.

Thereafter, the operator operates flow rate-reducing button 532 or flow rate-increasing button 534, thus driving rotary pump 528 at a speed lower or higher than before, whereby the flow rate of the fluid, thus locating the distal end of unit 6 at a desired level. If necessary, the operator rotates knob 20, thus bending flexible end portion 12 and subsequently guiding portion 12 to a desired position within tank 516. If the positions of jet port 32A and suction port 522A are interchanged, and also the positions of jet port 32B and 522B are interchanged, the thrust acting on flexible end tube 12 is altered, and tube 12 can be bent.

End end structure 14 of insertion section 6 held at a desired position and in a desired orientation. The image of the interior of tank 516 or the images of the interior of ducts 516A and 516B connected to tank 516 are displayed on TV monitor 78. Looking at these images, the operator can examine the interior of tank 516 or the interior of either duct. To still these images, it suffices to push freeze button 126 of operation unit 4. To record the images, it suffices to depress release button 126 of operation unit 4.

In some cases it may be required that gas such as air be prevented from flowing into tank 516 or duct 612A or 612B. If this is the case, electromagnetic switch 558 is operated prior to the use of endoscope 60, thereby opening electromagnetic valve 552. Hence, the fluid flows from cartridge tank 554 into the channels of endoscope 60, thus filling these channels with the fluid.

Physiologial salt solution may flow through channels 526A and 526B and also though the tubes provided within rotary pump 528. This solution causes no troubles if it flows into tank 516 or duct 612A or 612B. An anesthetic may be supplied from cartridge tank 554. There are various methods which can be used to fill the channels with the fluid. One of these may be to suck the fluid into the channels via suction ports 522A and 522B of insertion unit 6, then stop rotary motor 528 when the channels are filled up, next insert unit 6 into the object, and finally drive rotary pump 528 again. Once the channels within insertion unit 6 have been thus filled with the fluid, no other fluid, such as air, cannot flow into the channels or cannot mix with the fluid filled in the channels. Therefore, dangers, e.g., explosion of another fluid within the channels, is prevented.

In the fourteenth embodiment, insertion unit 6 has two jet ports 32A and 32B and two suction ports 522A and 522. Nonetheless, unit 6 may have one jet port and one suction port. Alternatively, more than two jet ports and more than two suction ports can be provided. Further, jet ports 32A and 32B can be connected to one same channel coupled to a rotary pump, and suction ports 522A and 522B can be connected to one channel coupled to the rotary pump. If this is the case, the rotary pump can circulate the fluid in endoscope 60.

Figure 166:
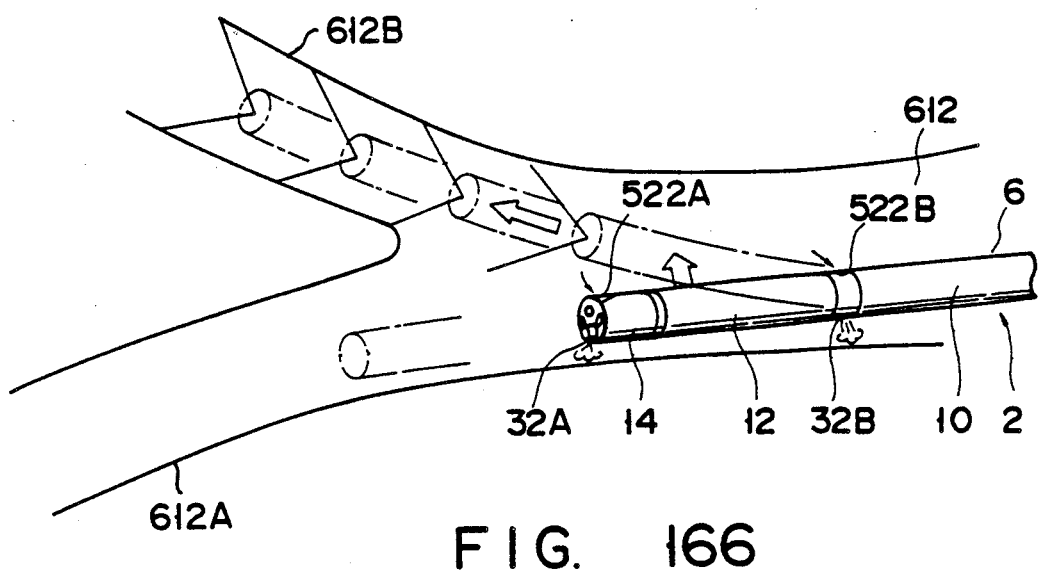
Figures 167, 168:
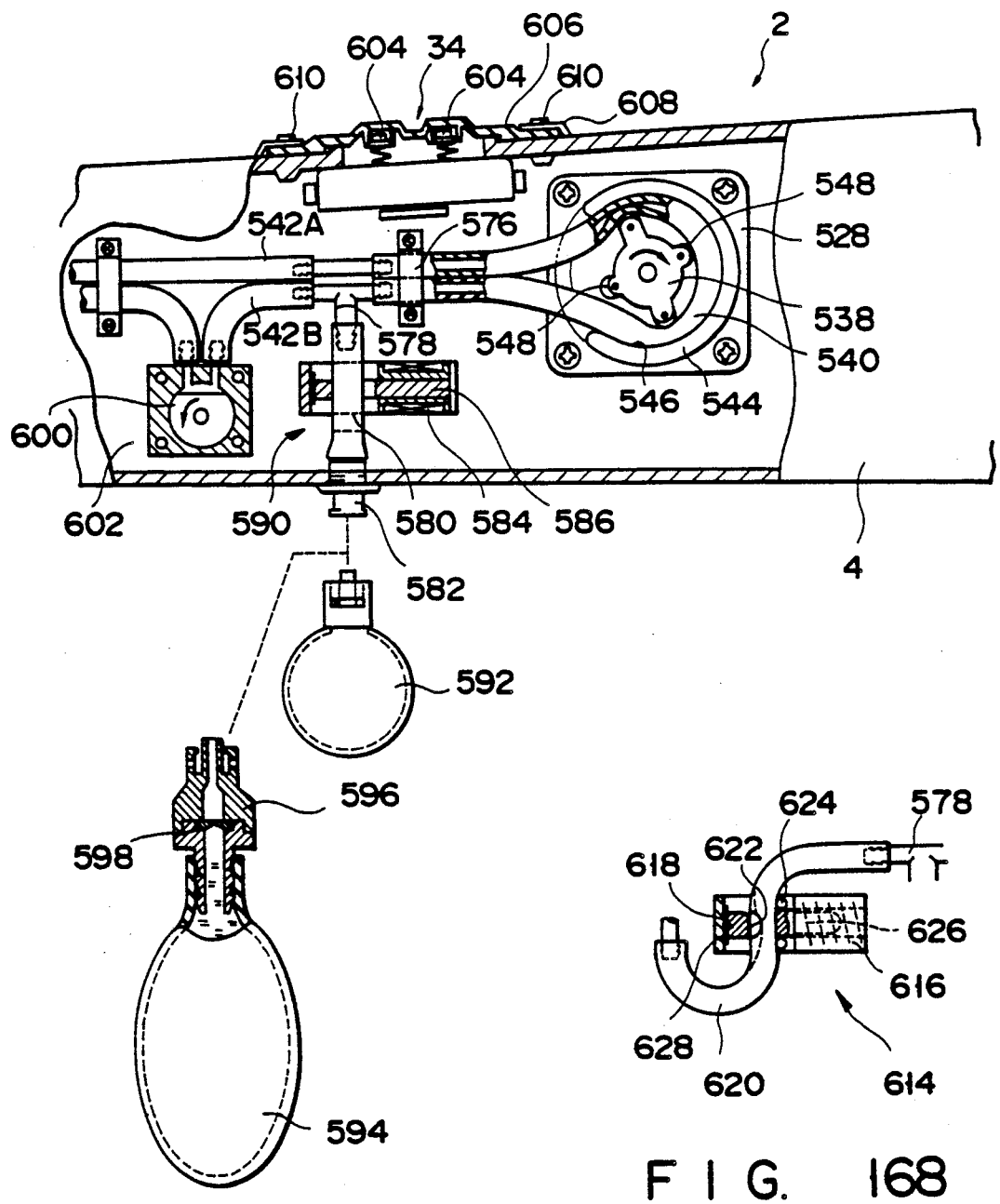

FIGS. 166 and 167 illustrates a first modification of the fourteenth embodiment of the present invention. This modification applies to endoscope 2 for examining the interior of blood vessels. Endoscope has operation unit 4. As is shown in FIG. 167, rotary pump 528 is incorporated in operation unit 4. Like the rotary pump used in the fourteenth embodiment, rotary pump 528 comprises rotor 528 and flexible tube 540 made of silicone rubber and looped around rotor 528. The ends of flexible tube 540 are held by fastener 576 and connected to channels 526A and 526B by mean of connecting tubes 542A and 542B, respectively. The middle portion of flexible tube 540 contact the inner periphery 546 of cylindrical base 544 which is concentric with rotor 538. A plurality of rollers 548 are mounted on the circumference of rotor 538. When rotor 538 is rotated in the direction of the arrow shown in FIG. 167, rollers 548 collapse tube 540, thereby supplying the fluid from channel 524A to channel 524B. T-shaped coupler 578 connects flexible tube 540 and connecting tube 542B located on the outlet side. Flexible tube 580 is connected at one end to T-shaped coupler 578, and at the other end to connecting cap 582. This tube 580 can be collapsed by plunger 586 which is driven by solenoid 584. That is, tube 580, solenoid 584, and plunger 596 constitute solenoid valve 590. Small flask 592 made of transparent glass or plastics is attached to connecting cap 582. Flask 592 is used to determine the condition of sucking the fluid. Alternatively, rubber balloon 594 can be connected to cap 582. Balloon 594 is filled with a transparent liquid such as physiological salt solution, a liquid medicine, or a nutritious solution. When necessary, balloon 594 is squeezed, thus supplying the transparent liquid into channels 52A and 526B. The transparent liquid, such as physiological salt solution, is eventually jetted through jet ports 32A and 32B, ensuring a good view of the interior of the blood vessels. One-way valve 598 is attached to cap 596 of rubber balloon 594. Since this valve 589 contains a rubber seal, the fluid cannot flow back into balloon 594. Balloon 594 can be made of transparent or semitransparent sythetic rubber elastomer, its the contents can be seen from outside.

Rotary valve 602 is connected in connecting tube 542B (outlet side). Valve 602 has rotor 600 rotated by a rotary solenoid (not shown). Another rotary valve, which is identical to valve 602, can be used in place of solenoid valve 590. All tubes used in the system, but those incorporated in rotary pump 528 and solenoid valve 590, can be made of relatively hard material.

Rubber cover 606 covers button switches 604 of control witch section 34, which are mounted on the upper portion of operation unit 4. Frame 608 holds the edge of rubber cover 606, and tapping pins 610 fasten cover 606 to operation unit 4. Another set of button switches can be provided on the lower portion of unit 4, diametrically opposed to the first set of switches 604.

It will now be explained how the first modification of the fourteenth embodiment is operated. First, the operator fills the fluid-circulating loop with physiological salt solution, and inserts insertion unit 6 into blood vessel 612 of the patient as is shown in FIG. 166. Then, he or she operates control switch section 34 of operation unit 4, thus turning rotary pump 528 on and off. As a result, the physiological salt solution is jetted via both jet ports 32A and 32B into blood vessel 612. Thus, end structure 14 of insertion section 6 is thrust in the direction opposite to the direction of the jet streams of the solution. Hence, and structure 14 is guided into one of the branches 612A and 612B of the blood vessel 612 At the same time the solution is thus jetted into blood vessel 612, the blood is sucked into the fluid circulating loop through both suction ports 522A and 522B, and is eventually circulated in this loop. Therefore, no harm is imposed on the patient from a physiological point of view.

FIG. 168 illustrates a modification of the solenoid valve. This modification has solenoid valve 614 which is used in place of rotary value 602. This solenoid value 614 has solenoid 616 and movable core 618. Solenoid 616 is used to drives core 6. Core 6 has through hole 622, in which connecting tube 620 made of silicone rubber passes. Tube 620 is held by tube holder 624. Movable core 618 is biased by spring 626 away from tube holder 624. When an electric current is supplied to solenoid 616, solenoid 616 moves core 618 toward tube holder 624, against the force of spring 626. Core 618 therefore collapses connecting tube 620, thus closing the fluid-circulating loop.

Buffer plate 628 made of rubber is attached to movable core 618, for absorbing the shock which core 618 causes when it is pushed back by spring 626 as solenoid 616 is turned off. Spring 626 can be dispensed with, if tube 620 is elastic enough to push back core 618 when solenoid 616 is turned off.

Figure 169:
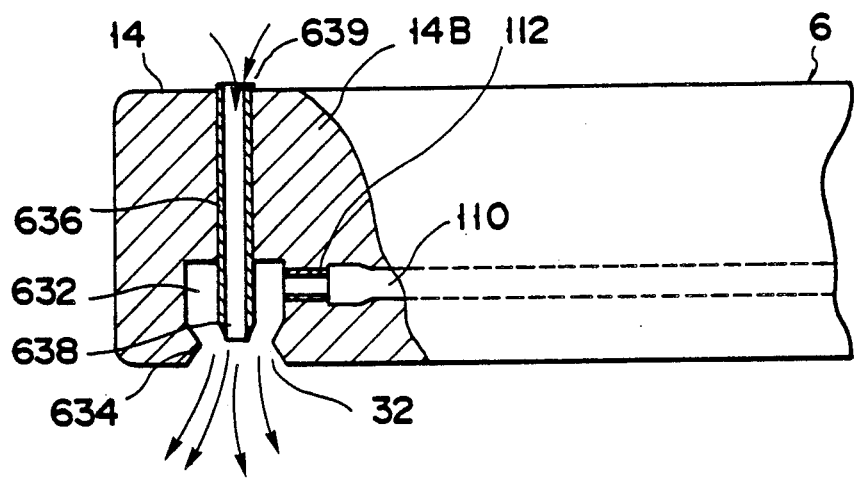
Figure 170:
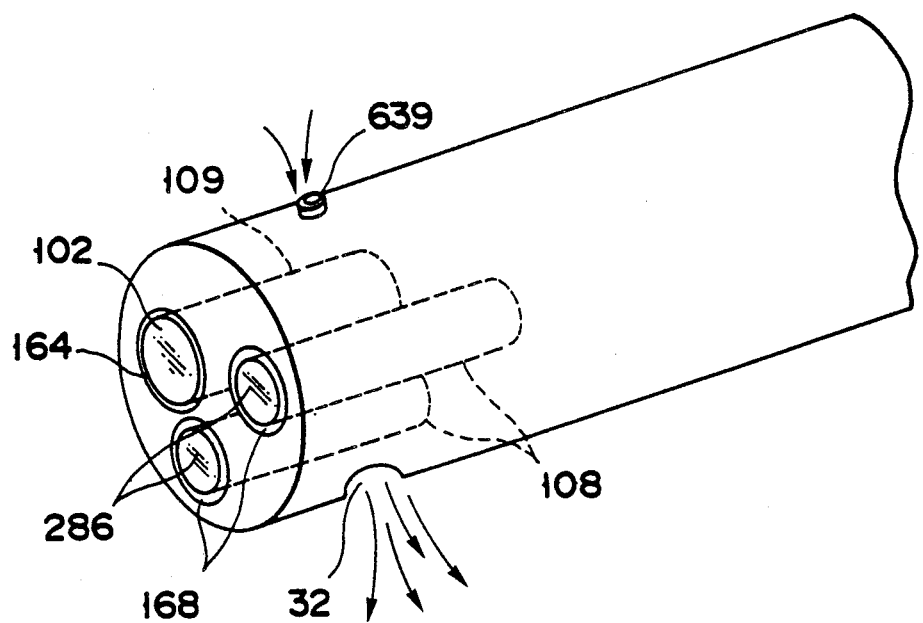
Figure 171:
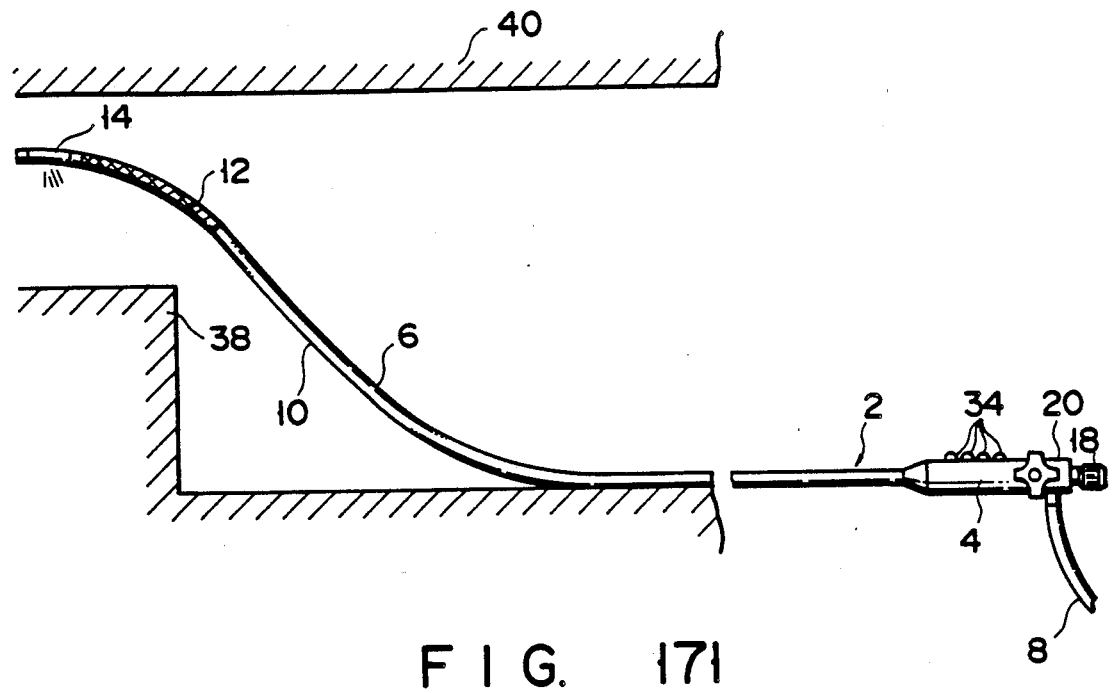

FIGS. 169 to 171 show a fifteenth embodiment of the present invention. As is illustrated in FIG. 171, endoscope 2 used in this embodiment comprises operation unit 4 and log insertion unit 6. Operation unit 4 is connected to an external apparatus (not shown) by means of cable 8. Insertion unit 6 comprises flexible tube 10 connected to unit 4, flexible and portion 12 coupled to tube 10, and end structure 14 connected to end portion 12. End portion 12 can be remote-controlled and bent by rotating knob 20 attached to operation unit 4.

End structure 14 of insertion unit 6 has the structure shown in FIGS. 169 and 170. As these figures show, end structure 14 has observation window 164 and illumination window 168 in the distal end portion 14B. Glass cover 285 of illumination window 168 is connected to light guide 108 (i.e., an optical fiber). Observation window 164 is optically coupled to objective lens system 102, which in turn is connected to image guide 109 (i.e., an optical fiber). Light guide 108 is extends via insertion unit 6, operation unit 4, and cable 6, and is coupled to the light source built in the external apparatus. Image guide fiber 109 extends through insertion unit 6 and is connected to the eyepiece lens system of eyepiece unit 18 incorporated in operation unit 4.

As is shown in FIGS. 169 and 170, jet port 32 is made in the lower portion of end portion 14B. This port 32 communicates with chamber 632 which is a recess formed in portion 14B. Throttle 634 is located between port 32 and chamber 632. Connecting tube 112 is embedded in portion 14B, opening to chamber 632. Tube 112 is connected to flexible tube 110 for supplying air. Flexible tube 110 extends through insertion unit 6, operation unit 4, and cable 6, and is connected to the compressor provided within the external apparatus. The high-pressure air supplied from the compressor can, therefore, be supplied through tube 112 into chamber 632. Suction tube 636 extends through distal end portion 14B in the direction at right angles to the axis of end structure 14. One end of tube 636 is located in jet port 32 and functions as outlet port 638A, and the other end thereof opens at the upper portion of end structure 14 and functions as inlet port 639 tube 110 into chamber 632, the air swirls within this camber 632 and then flows downward through jet port 32 from distal end portion 14B. Insertion unit 6 is raised by the thrust resulting from the reaction of the high-pressure air. As the air flows downward via jet port 32, a negative pressure is generated in inlet port 639 of suction tube 636. Because of this negative pressure, air flows into inlet 639 into tube 636, and is jetted from port 32, along with the high-pressure air.

The supply of the high-pressure air from the compressor to chamber 632 through tube 11 is performed by operating control switch section 34 of operation unit 4. Alternately, the supply of the high-pressure air can be carried out by operating the operation unit (not shown) provided on the external apparatus.

It will now be described how endoscope 2 according to the fifteenth embodiment is operated, with reference to FIG. 171. When stepped portion 3u exists within object 40 which is to be examined by means of endoscope 2 as is shown in FIG. 171, end structure 14 must pass over this portion 38, so as to be guided deeper into object 40. Stepped portion 38 is too high for the distal end portion of unit 6 to pass over, if flexible tube 12 is bend by operating operation unit 4. In this case, the high-pressure air is supplied from the compressor via tube 110 and jetted downward from the distal end portion 14B through jet port 32. As a result, insertion unit 4 is raised by virtue of the thrust generated by the jet stream of the high-pressure air. As the high-pressure air is jetted in this way, a negative pressure is created in inlet port 639. Due to this negative pressure, air is sucked into suction tube 636 and subsequently jetted downward through jet port 32, along with the high-pressure air. Hence, insertion unit 6 is more effectively raised than in the case where only the high-pressure air works to thrust unit 6 upward.

The thrust (F) generated by the jet stream of a high-pressure fluid is given as follows:

$$F = \rho Wv + (P1 - P0)A$$

where:
$\rho$: density of the fluid
Q: flow rate of the fluid
$v$: relative speed of the fluid
P0: atmospheric pressure
P1: pressure in the jet port
A: cross-sectional area of the jet port As can be understood from the above equation, the thrust (F) is believed to increase in proportion to the flow rate (Q) of the fluid.

Since jet port 32 and suction port 538 are arranged symmetrically with each other with respect to the axis of end structure 14, the air flows steadily along the diameter of distal end portion 14B. Hence, insertion unit 6 is raised, without vibrating. Unit 6 can thus be easily guided into object 40, and the image can be prevented from moving in the observation view field. Hence, end structure 14 can be raised above stepped portion 38 and guided over this portion 38, as is shown in FIG. 171. Further, distal end portion 14B of structure 14 can be raised to touch the ceiling of object 40, if necessary, so that the ceiling.

Since jet port 32 is made in the distal end portion 14B of end structure 14, not projecting therefrom, insertion unit 6 is comparatively thin.

Figure 172:
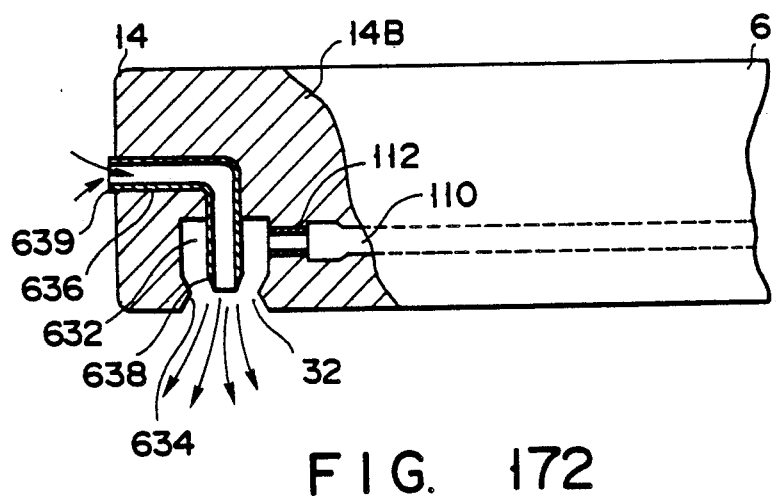

FIG. 172 illustrates a fist modification of the fifteenth embodiment of the present invention. Suction tube 636 is bend in the form of letter L, consisting of a horizontal portion and a vertical portion. The horizontal portion opens at the distal-end surface of structure 14, and the vertical portion opens in jet port 32. Thus, air is sucked into tube 636 from the distal-end surface of structure 14 when the high-pressure air is jetted downward through jet port 32.

Figure 175:
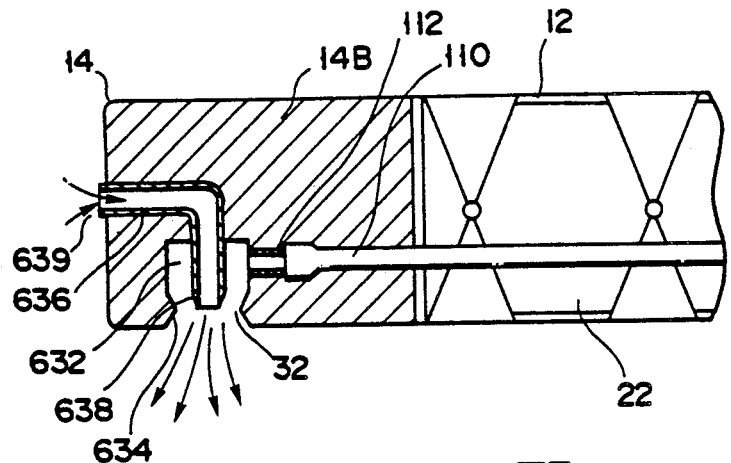

FIG. 173 through FIG. 176 show a second modification of the fifteenth embodiment. This modification is characterized in two respects. First, end structure 14 is coupled to the distal end of flexible end portion 12. Secondly, suction tube 636, either straight as is shown in FIG. 173 or bent as is shown in FIG. 175, is provided in end structure 14.

Figure 176:
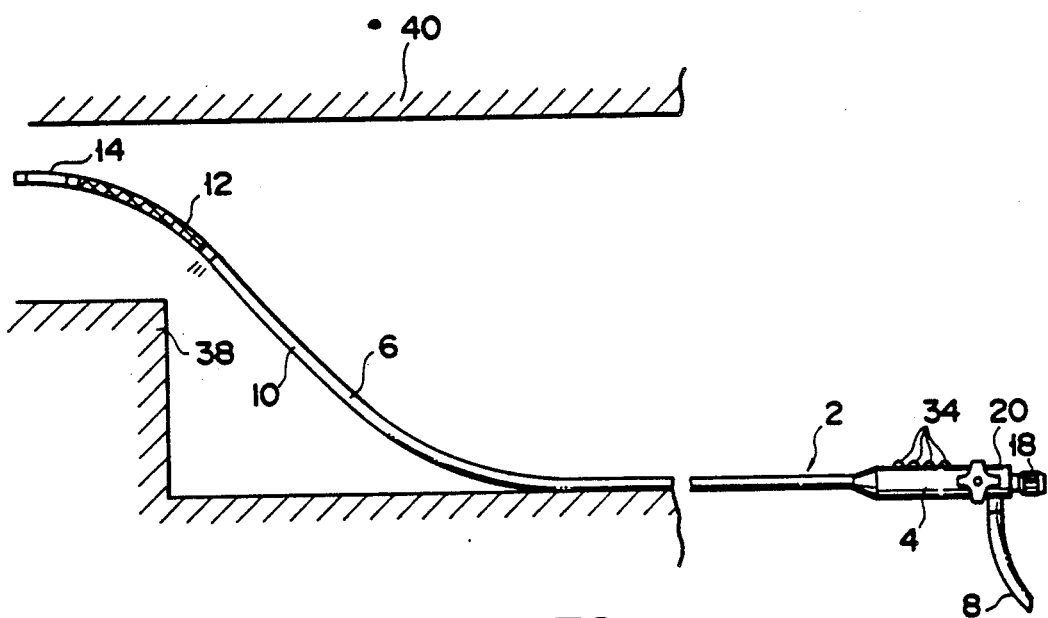
Figure 177:
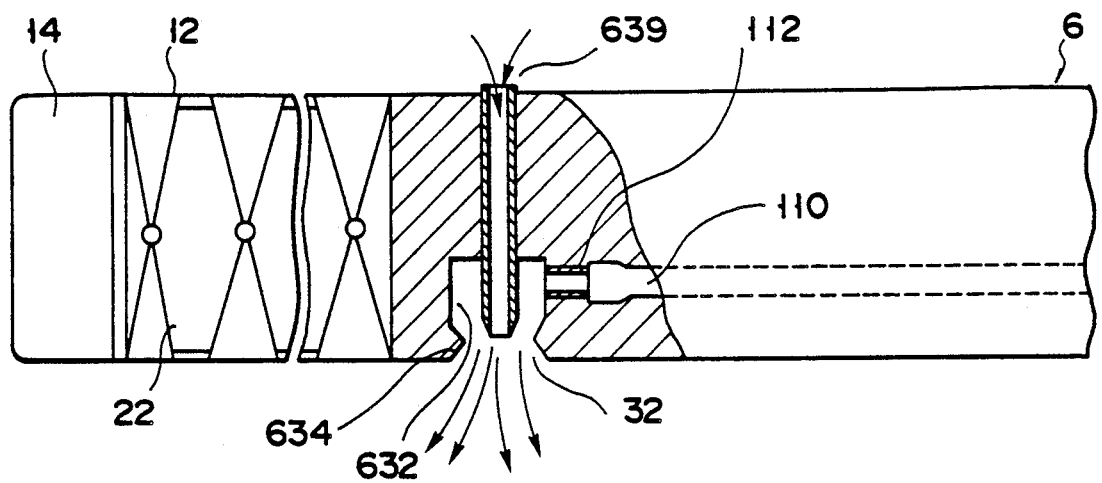
Figure 178:
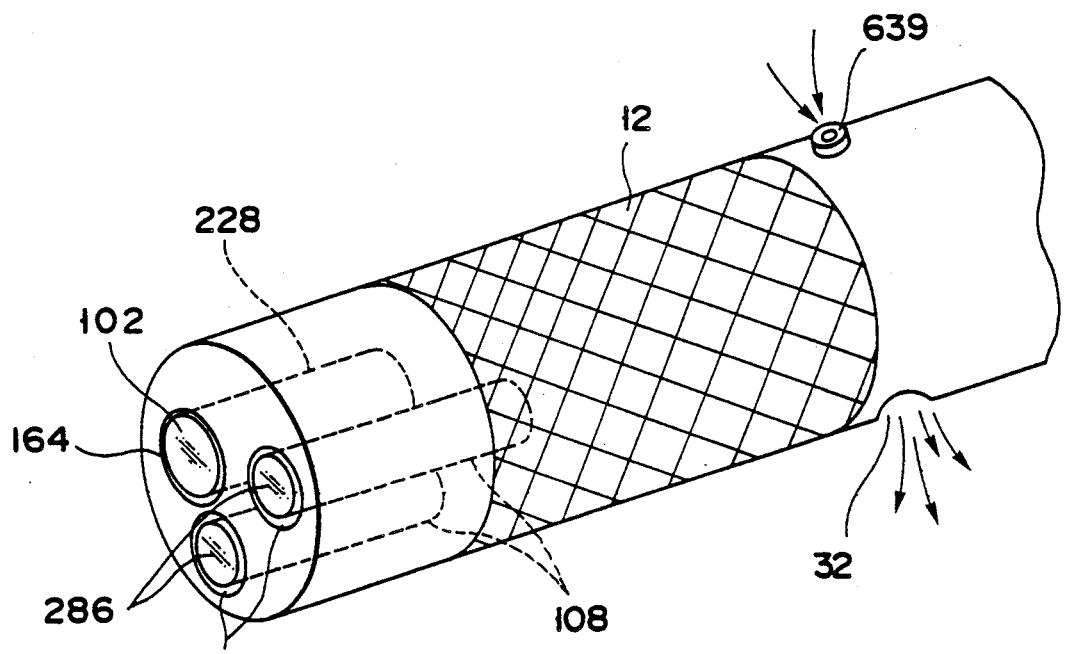

FIG. 176 through FIG. 179 show a third modification of the fifteenth embodiment. The third modification is characterized in that straight suction tube 636 extends through that portion of end structure 14 which is connected to the distal end of flexible and portion 12. Due to this specific position of suction tube 638, end structure 14 can be easily passed over the stepped portion 38 existing in duct 40, as is illustrated in FIG. 176. The third modification can, therefore, accomplish the same advantages as the fifteenth embodiment.

FIGS. 179, 180 and 181 illustrate a sixteenth embodiment of the present invention. FIG. 179 shows the end structure 14 of insertion unit 6. insertion unit 6 is flexible, except for end structure 14. Objective lens system 102 and solid-state image sensor element 104 are incorporated in end structure 14. System 102 has an objective lens which focuses, on the light-receiving surface of element 104, the image seen in the view field of observation window 164. As is shown in FIG. 180, illumination window 168 is provided on the distal-end surface of structure 14. A lamp is located behind illumination window 168, or a light guide is optically connected to illumination window 168.

As is shown in FIG. 179, connector tube 112 extends through end structure 14. The inner end of this tube 112 is coupled to flexible tube 110. Flexible tube 110 extends through an insertion unit 6 and an operation unit 4. It is coupled to a pressurized fluid supply means provided outside endoscope, such as a compressor or a pump. The pressurized fluid supply means can be remote-controlled by the operation switches mounted on the operation unit.

Nozzle 642 is attached to connector tube 112. As is shown in FIG. 180, nozzle 642 is eccentric to insertion unit 6, and located below observation window 164. Nozzle 626 is a hollow cylinder closed at the distal end. The proximal end of nozzle 626 is fitted in tube 112 in screw engagement. The interior of nozzle 626 communicates with channel 110A. The distal end portion of nozzle 262 projects from the distal end of end structure 14, as is illustrated in FIG. 179. Two jet ports 32 and 644 are made in this distal end portion. Jet port 32 has a relatively large diameter, and extends slantwise and rearward. Second jet port 644 has a relatively small diameter, is positioned symmetrically to first jet port 32 with respect to the axis of end structure 14, and extends slantwise and toward observation window 164. The high-pressure fluid supplied via tubes 110 and 112 is jetted through both jet ports 32 and 644.

Further, guide 646 protrudes from the outlet of port 32, in the axial direction of jet port 32. The high-pressure fluid jetted from port 32 is guided along the surface 646A of guide 646, and thus in the axial direction of jet port 32.

It will now be explained how the endoscope system according to sixteenth embodiment is operated. First, the operator inserts insertion unit 6 into an object in order to examine the interior of this object. Then, he or she operates the control switches mounted on the operation unit, thus remote-controlling the pressurized fluid supply means. As a result of this, the high-pressure fluid, such as air, is supplied form the fluid supply means to nozzle 642 via tubes 110 and 112. Hence, as is shown in FIGS. 179 and 181, the fluid is jetted through both jet ports 32 and 644. The thrust resulting from the jet stream via first jet port 32 raises the distal end portion of insertion unit 6. The jet stream though second jet port 644, which has a small diameter, is not strong enough to cause a noticeable reduction of the thrust generated by the jet stream through first jet port 32. Thereafter, the operator adjusts the flow rate of the fluid, thus further raising insertion unit 6 and bending unit 6, and guiding the distal end of unit 6 to a desired position within object. Guide 646 prevents the jet stream from port 32 from diverging and weakening. Also, guide 646 guides the jet stream such that the stream has a cross section of a specific shape, such as a semicircular shape. Therefore, insertion unit 6 less swings than when the stream has a circular cross section. In other words, unit 6 is stably held within the object, and the image of the interior of the object, which is seen in the view field of the endoscope, does not move. Since the distal end portion of insertion section 6 is reliably orientated, it is easy for the operator to guide the distal end of unit 6 to a desired position within the object.

The weak jet stream from second jet port 644 is applied to observation window 164 which is exposed outside, thereby removing dust from window 164. Since observation window 644 is cleaned this way, the interior of the object can be photographed to provide a clear image thereof.

FIG. 182 shows a modification of the sixteenth embodiment of the invention. This modification is characterized by antenna guide 48 which extends forward from the distal end of nozzle 642. Antenna guide 48 is a densely wound coil, and can be elastically bent. Ball 648 is loosely fitted in the distal end of guide 48 and can thus roll. Guide antenna 48 guides insertion unit 6 smoothly into a duct or the like, which is meandering. The modification is also characterized in that image guide 109 is used in place of solid-state image sensor element.

FIGS. 183 and 184 illustrates a seventeenth embodiment of the present invention. Endoscope 60 according to this embodiment compresses insertion unit 6. Unit 6 has flexible tube 10, flexible end portion 12, and end structure 14. flexible tube 10 is bent when an external force is applied to it. A number of segments, are coupled together, are provided in flexible end portion 12. Wires (not shown) are connected, at one end, to the segments, and at the other end, to the operation unit (not shown) of endoscope 60. When the operation unit is operated, thereby pulling some of these wires, leaving the other worse slackened, flexible end portion 12 is bent. As is shown in FIG. 184, observation window 164 and illumination window 168 are formed on the distal-end surface 14A of end structure 14. Window 164 is optically coupled to an observation optical system (not shown), and window 168 is optically connected to an illumination optical system (not shown, either). The observation optical system has an image guide or a solid-state image sensor element. The image in the view field of window 164 can be seen by means of the observation optical system. The illumination optical system has a lamp or a light guide, and applies light from window 160 to illuminate the view field of endoscope 60.

Four jet ports 32 are made in the circumference of end structure 14. Ports 32 are slits extending parallel to the axis of insertion unit 6 and spaced apart at angle intervals of 90° in the circumferential direction of structure 14. Jet ports 32 are connected to four fluid-supply passages 110, respectively. These passages 110 extends through insertion unit 6 and are connected to a fluid source provided outside endoscope 60. Operation buttons are provided on the operation unit (not shown). When these buttons are operated, the fluid is supplied from the fluid source to at least two jet ports 32 and jetted from end structure 14 through these jet ports.

Four jet ports 33 are formed in jet port member 30 which connects flexible tube 10 and flexible end portion 12. These ports 33 are also slits extending parallel to the axis of insertion unit 6. The fluid can be jetted through ports 33 in jet streams having a thin rectangular cross section. Jet ports 33 are connected to fluid-supply passages 110, respectively. Jet ports 33 are spaced apart from one another at angle intervals of 90° in the circumferential direction of unit 6. Also, jet ports 33 are displaced from jet ports 32 by 45°. the fluid is supplied to any of these ports 33 at any desired flow rate, in accordance with the operation of the operation unit.

It will now be explained how endoscope 60 is used. The operator inserts insertion unit 6 into an object, while operating the operation unit of endoscope 60, thereby jetting the fluid such as air through jet ports 32 and 33. Due to the reaction of the jet streams of the fluid, insertion unit 6 is moved upward. For example, as is shown in FIGS. 183 and 184, the fluid is jetted out via two lower ports 32 made in end structure 14 and also via the lowerest port 33 made in jet port member 30. In other words, three jet streams a, b and c are applied in different directions, as is illustrated in FIG. 184. Hence, insertion unit 6 is moved upward in the direction of arrow U showing the sum of the three reactionary forces of the three jet streams a, b and c, and which is opposite to the direction of arrow F representing the sum of the forces of jet streams a, b and c. By virtue of three jet streams, insertion unit 6 rises stably.

When the jet streams from ports 32 are strong enough to raise insertion unit 6, the fluid need not be jetted through ports 33 made in jet port member 30. The fluid can be jetted through two of the four ports 33, thereby to twist jet port member 30 by 45° with respect to end structure 14.

Since jet ports 32 and 33 are elongated slits, the jet stream ejected through them have a thin rectangular cross section. Unlike slender jet streams having a circular cross section, they create a stable thrust to insertion unit 6. Due to the stable thrust, insertion unit 6 is stably raised without swinging sideways. Unit 6 can therefore be busily guided deeper into an object.

When insertion unit 6 is bent by operating the operation unit, while it is being raised by virtue of the jet streams, end structure 14 can be guided more easily.

In the seventeenth embodiment, jet ports 33 made in jet port member 33 can be aligned with ports 32 made in end structure in the axial direction of insertion unit 6, not displaced in the circumferential direction of insertion unit 6. Moreover, ports 32 and 33 can be formed in any other portions of insertion unit 6. Still further, these ports, which are slits, may extend, for example, the circumferential direction of unit 6, instead of the axial direction thereof.

What is claimed is:

1. A borescope apparatus comprising:
   (A) a borescope including:
      a. an operation unit;
      b. an insertion unit having a bending tube portion being bent by operating the operation unit, a jet port member connected to a proximal end of the bending tube portion and having a jet port for ejecting a fluid, and a flexible tube portion connected to the jet port member and being bent by fluid jet from the jet port, independently of the bending tube portion; and
   (B) pressurized fluid supply means for supplying a pressurized fluid to the jet port of said jet port member.

2. The borescope apparatus according to claim 1, further comprising control means for controlling the pressurized fluid being supplied to said jet port and remote-controlling said insertion unit.

3. The borescope apparatus according to claim 1, wherein said jet port member has a plurality of jet ports.

4. The borescope apparatus according to claim 3, further comprising control means for controlling the pressurized fluid being supplied to said jet ports and remote-controlling said insertion unit.

5. The borescope apparatus according to claim 4, wherein said control means has angle-adjusting means for controlling the pressurized fluid, adjusting the flow rate of the fluid being ejected through said jet ports, thereby to bend said insertion unit to a desired degree in a predetermined direction.

6. The borescope apparatus according to claim 4, further comprising detector means for detecting the direction in which said fluid applies a thrust to said insertion unit, and display means for displaying the direction detected by said detector means, in a view field of the borescope or in the vicinity thereof.

7. The borescope apparatus according to claim 2, wherein said control means comprises:
   detector means for detecting the pressure of the pressurized fluid being supplied to said jet port, and generating a signal representing this pressure; and
   pressure-adjusting means for controlling the pressurized fluid in accordance with the signal supplied from said detector means, thereby to maintain the pressure of the fluid being ejected through said jet port, at a constant value.

8. The borescope apparatus according to claim 2, wherein said control means comprises:
   detector means for detecting the degree of bending of said insertion unit, and generating a signal representing the degree of bending; and
   pressure-adjusting means for controlling the pressurized fluid in accordance with the signal supplied from said detector means, thereby to maintain the pressure of the fluid being ejected through said jet port.

9. The borescope apparatus according to claim 2, wherein said control means comprises means for intermittently ejecting the pressurized fluid through said jet port.

10. The borescope apparatus according to claim 2, wherein said control means comprises fluid-adjusting means provided in said jet port, for adjusting the stream of the fluid being ejected through said jet port.

11. The borescope apparatus according to claim 10, wherein said fluid-adjusting means includes pressure-adjusting means for adjusting the pressure of the fluid being ejected through said jet port.

12. The borescope apparatus according to claim 10, wherein said fluid-adjusting means includes flow rate-adjusting means for adjusting the flow rate of the fluid being ejected through said jet port.

13. The borescope apparatus according to claim 2, wherein said control means comprises direction-changing means for changing the direction in which the fluid is being ejected through said jet port.

14. The borescope apparatus according to claim 13, wherein said control means is incorporated in said operation unit and comprises means for operating said direction-changing means.

15. The borescope apparatus according to claim 13, wherein said direction-changing means has a member rotatably attached to the distal end of said insertion unit and having a center of rotation and a center of gravity displaced from the center of rotation.

16. The borescope apparatus according to claim 13, wherein said direction-changing means has an adapter detachably coupled to the distal end of said insertion unit and having a jet port for ejecting the fluid in a specified direction.

17. The borescope apparatus according to claim 1, further comprising a suction tube having two ends, the first end projecting into said jet port, and the second end opening at the outer surface of said insertion unit.

18. The borescope apparatus according to claim 1, further comprising guide means for guiding the fluid from said jet port in a specified direction.

19. The borescope apparatus according to claim 1, wherein said jet port is in the form of an elongated slit.

20. A borescope apparatus, comprising:
an operation unit;
an insertion unit having a jet port for ejecting a fluid;
pressurized fluid supply means for supplying a pressurized fluid to said jet port;
control means provided in said operation unit, for regulating the pressured fluid and for remote-controlling said insertion unit;
wherein said insertion unit has a plurality of jet ports; and
detector means for detecting a direction in which said fluid applies a thrust to said insertion unit, and display means for displaying the direction detected by said detector means, in a view field of the borescope or in the vicinity thereof.

21. A borescope apparatus, comprising:
an operation unit;
an insertion unit having a jet port for ejecting a fluid;
pressurized fluid supply means for supplying a pressurized fluid to said jet port; and
control means provided in said operation unit, for regulating the pressurized fluid and for remote-controlling said insertion unit;
wherein said control means comprises:
detector means for detecting a pressure of the pressurized fluid being supplied to said jet port, and for generating a signal representing the pressure; and
pressure-adjusting means for controlling the pressurized fluid in accordance with the signal supplied from said detector means, and for maintaining the pressure of the fluid being ejected through said jet port, at a constant value.

22. A borescope apparatus, comprising:
an operation unit;
an insertion unit having a jet port for ejecting a fluid;
pressurized fluid supply means for supplying a pressurized fluid to said jet port; and
control means provided in said operation unit, for regulating the pressurized fluid and for remote-controlling said insertion unit;
wherein said control means comprises
detector means for detecting a degree of bending of said insertion unit; and for generating a signal representing the degree of bending; and
pressure-adjusting means for controlling the pressurized fluid in accordance with the signal supplied from said detector means, and for maintaining the pressure of the fluid being ejected through said jet port, at a desired value.

23. A borescope apparatus, comprising:
an operation unit;
an insertion unit having a jet port for ejecting a fluid;
pressurized fluid supply means for supplying a pressurized fluid to said jet port; and
control means provided in said operation unit, for regulating the pressurized fluid and for remote-controlling said insertion unit;
wherein said control means comprises means for intermittently ejecting the pressurized fluid through said jet port.

24. A borescope apparatus, comprising:
(A) an insertion unit having a rear end portion and a jet port for ejecting a fluid;
(B) an operation unit connected to the rear end portion of the insertion unit;
(C) pressurized fluid supply means for supplying a pressurized fluid to the jet port; and
(D) control means, provided in the operation unit, for controlling the pressurized fluid being supplied to the jet port and for remote-controlling the insertion unit, said control means including,
(a) adjusting means for adjusting the fluid being ejected from the jet port,
(b) angle-adjusting means for controlling the pressurized fluid, adjusting the flow rate of the fluid being ejected through the jet ports, and for bending the insertion unit to a desired degree in a predetermined direction, said angle-adjusting means having,
angle knob means for setting the curve angle of the floated insertion unit,
encoder means for outputting a signal to the control unit in accordance with the angle of rotation and the direction of rotation of the angle knob, and
control unit means for controlling a regulator, upon receiving a signal from the encoder.

25. A borescope apparatus, comprising:
an insertion unit having a plurality of jet ports for ejecting a fluid;
an operation unit connected to the insertion unit;
pressurized fluid supply means for supplying a pressurized fluid to the jet ports; and
control means for controlling the pressurized fluid being supplied to the jet ports and for remote-controlling the insertion unit, said control means including:
adjusting means for adjusting the flow rate of the fluid being ejected through the jet ports; and
angle-adjusting means for controlling the pressurized fluid, for adjusting the flow rate of the fluid being ejected through the jet ports, and for bending the insertion unit to a desired degree in a predetermined direction; and said angle-adjusting means including:
floating curve angle setting means for setting a curve angle of the insertion unit being floated;
control unit means for controlling a regulator, upon receiving a signal from the floating curve angle setting means; and regulator means for controlling the flow rate of the fluid being ejected through the jet ports on the basis of a signal supplied from the control unit means.

26. The apparatus according to claim 25, wherein said floating curve angle setting means includes:
rotatable angle knob means for setting the curve angle of the insertion unit being floated; and
encoder means for outputting a signal to the control unit in accordance with the angle of rotation and the direction of rotation of the angle knob means.

27. The apparatus according to claim 25, wherein said floating curve angle setting means includes pressure control switch means for outputting to the control unit means a signal representing the curve angle of the floated insertion unit.

28. The apparatus according to claim 25, wherein said pressurized fluid supply means has a pressurized fluid source, and a pipe connecting the pressurized fluid source and the jet ports, and said regulator means has variable valve means for controlling compressed air fed from the pressurized fluid source to the jet ports, on the basis of a signal from the control unit means.

* * * * *

UNITED STATES PATENT AND TRADEMARK OFFICE
CERTIFICATE OF CORRECTION

PATENT NO. : 4,991,957
DATED : February 12, 1991
INVENTOR(S) : SAKAMOTO et al

It is certified that error appears in the above-identified patent and that said Letters Patent is hereby corrected as shown below:

Title page,

Section [75] Inventors: Change

"Morihide Tojo" to --Yoshikazu Tojo--;

"toshiaki Nishikiori" to --Toshiaki Nishikiori--.

Section [30] Foreign Application Priority Data:

Change "63-537612" to --63-53761--.

Signed and Sealed this

Tenth Day of November, 1992

*Attest:*

DOUGLAS B. COMER

*Attesting Officer*    *Acting Commissioner of Patents and Trademarks*